US007300932B2

(12) United States Patent
Fox et al.

(10) Patent No.: US 7,300,932 B2
(45) Date of Patent: Nov. 27, 2007

(54) PYRROLO[1,2-B]PYRIDAZINE DERIVATIVES

(75) Inventors: Brian M. Fox, San Mateo, CA (US); Kiyosei Iio, Takatsuki (JP); Takashi Inaba, Takatsuki (JP); Frank Kayser, San Francisco, CA (US); Kexue Li, Palo Alto, CA (US); Shoichi Sagawa, Takatsuki (JP); Masahiro Tanaka, Takatsuki (JP); Atsuhito Yoshida, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 263 days.

(21) Appl. No.: 10/913,307

(22) Filed: Aug. 6, 2004

(65) Prior Publication Data

US 2005/0070545 A1    Mar. 31, 2005

Related U.S. Application Data

(60) Provisional application No. 60/493,997, filed on Aug. 7, 2003.

(51) Int. Cl.
C07D 487/04 (2006.01)
A61K 31/5025 (2006.01)

(52) U.S. Cl. ...................... 514/248; 544/235
(58) Field of Classification Search ................ 544/235; 514/248
See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 6,069,143 A | 5/2000 | Ali et al. | |
| 6,472,389 B1 | 10/2002 | Ohtani et al. | |
| 6,512,099 B2 | 1/2003 | Omura et al. | |
| 2004/0209871 A1 | 10/2004 | Fox et al. | |

FOREIGN PATENT DOCUMENTS

| | | |
|---|---|---|
| EP | 1 431 267 A1 | 6/2004 |
| JP | 05-213985 A | 8/1993 |
| JP | 2002-284741 A | 10/2002 |
| JP | 2004-067635 A | 3/2004 |
| KR | 2003-045230 A | 6/2003 |
| WO | WO 01/32632 A2 | 5/2001 |
| WO | WO 01/32632 A3 | 5/2001 |
| WO | WO 03/016254 A1 | 2/2003 |
| WO | WO 03/018536 A1 | 3/2003 |
| WO | WO 2005/072740 A2 | 8/2005 |

OTHER PUBLICATIONS

Cecil Textbook of Medicine, edited by Bennet, J.C., and Plum F., 20th edition,vol. 1, 1004-1010, 1996.*
Chen et al., Trends in Cardiovascular Medicine 10: 188-192, 2000.*
Chen et al. Arterioscler. Vasc. Biol. 25 (3): 482-486, 2005 (abstract two pages).*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Moore et al. J. Org. Chem., vol. 37, No. 24, 1972.*
Bagdade, *Diabetes Reviews*, 5(4): 392-409 (1997).
Bast et al., "Imunostimulants", Chapter 60, Section 16, pp. 790-799, in *Cancer Medicine*, 5th ed: (Hamilton, Ontario, CA: B.C. Decker, 2000).
Berge et al., *Journal of Pharmaceutical Sciences*, 66(1): 1-19 (Jan. 1977).
Buhman et al., *Journal of Biological Chemistry*, 277(28): 25474-25479 (Jul. 12, 2002).
Cases et al., *Journal of Biological Chemistry*, 276(42): 38870-38876 (Oct. 19, 2001).
Cases et al., *Proc. Natl. Acad. Sci. USA*, 95: 13018-13023 (Oct. 1998).
Chen et al., *Diabetes Reviews*, 5(4): 331-342 (1997).
Chen et al., *Journal of Clinical Investigation*, 109(8): 1049-1055 (Apr. 2002).
Chen et al., *Trends Cardiovasc. Med.*, 10(5): 188-192 (2000).
Chiasson et al., *Annals of Internal Medicine*, 121(12): 928-935 (Dec. 15, 1994).
Clemmons, *Diabetes Reviews*, 5(4): 353-364 (1997).
Coniff et al., *American Journal of Medicine*, 98: 443-451 (May 1995).
Coniff et al., *Clinical Therapeutics* 19(1): 16-26 (1997).
Dean et al., *Journal of Organic Chemistry*, 58: 7916-7917 (1993).
Farese et al., *Curr. Opin. Lipidol.*, 11:229-234 (2000).
Garg et al., *Diabetes Reviews*, 5(4): 425-433 (1997).
Haffner, *Diabetes Care*, 21(1): 160-178 (Jan. 1998).
Hsueh et al., *Diabetes Reviews*, 5(4): 343-352 (1997).
Iwamoto et al., *Diabetic Medicine*, 13(4): 365-370 (Apr. 1996).
Jokl et al., *Diabetes Reviews*, 5(4): 316-330 (1997).
Kwiterovich, *The American Journal of Cardiology*, 82(12A): 3U-17U (Dec. 17, 1998).
Laakso et al., *Diabetes Reviews*, 5(4): 294-315 (1997).
Lewis et al., *Endocrine Reviews*, 23(2): 201-229 (Apr. 2002).
Lopes-Virella et al., *Diabetes Reviews*, 5(4): 410-424 (1997).
Lyons et al., *Diabetes Reviews*, 5(4): 365-391 (1997).
Mahler et al., *Journal of Clinical Endocrinology & Metabolism*, 84(4): 1165-1171 (Apr. 1999).
Malloy et al., "Chapter 4: A Risk Factor for Atherosclerosis: Triglyceride-rich Lipoproteins," *Advances in Internal Medicine*, 47: 111-136 (Mosby, Inc., 2001).
March, *Advanced Organic Chemistry*, 4th ed: 1091-1092 (New York: John Wiley & Sons, 1992).
Newcomb et al., *Journal of Organic Chemistry*, 45: 1707-1708 (1980).

(Continued)

*Primary Examiner*—Kahsay Habte
(74) *Attorney, Agent, or Firm*—Leydig, Voit & Mayer, Ltd.

(57) ABSTRACT

Compounds, pharmaceutical compositions and methods that are useful in the treatment or prevention of metabolic and cell proliferative diseases or conditions are provided herein. In particular, the invention provides compounds which modulate the activity of proteins involved in lipid metabolism and cell proliferation.

17 Claims, No Drawings

OTHER PUBLICATIONS

Oelkers et al., *Journal of Biological Chemistry*, 273(41): 26765-26771 (Oct. 9, 1998).
Purnell et al., *Diabetes Reviews*, 5(4): 434-444 (1997).
Samaritoni, *Organic Preparations and Procedures International (OPPI)*, 20(2): 117-121 (Apr. 1988).
Smith et al., *Nature Genetics*, 25: 87-90 (May 2000).
Turner et al., "Insulin resistance, impaired glucose tolerance and non-insulin-dependent diabetes, pathologic mechanisms and treatment: Current status and therapeutic possibilities," *Progress in Drug Research*, 51: 33-94 (Basel, Switzerland: Birkhäuser Verlag, 1998).
United Kingdom Prospective Diabetes Study (UKPDS) Group, *Diabetes Care*, 21(1): 87-92 (Jan. 1998).
Wermuth (ed.), "Molecular Variations Based on Isosteric Replacements," *The Practice of Medicinal Chemistry*, 13: 203-237 (London: Academic Press Limited, 1996).
Barone, *Journal of Medicinal Chemistry*, 6: 39-42 (Jan. 1963).
Chen et al., *Diabetes*, 51: 3189-3195 (2002).
Chen et al., *Journal of Clinical Investigation*, 111: 1715-1722 (2003).
Chen et al., *Diabetes*, 54(12): 3379-3386 (2005).
Chung et al., *Planta Med.*, 70: 256-258 (2004).
Gaziano et al., *Circulation*, 96: 2520-2525 (1997).
Kim et al., *J. Medicinal Chemistry*, 17(3): 369-371 (1974).
Ko et al., *Archives of Pharmacal Research*, 25(4): 446-448 (2002).
Landauer et al., *Journal of Chemical Society*: 3721-3722 (1953).
Lee et al., *Planta Med*, 70: 197-200 (2004).
Nahm et al., *Tetrahedron Letters*, 22(39): 3815-3818 (1981).
Oikawa, "Medicine for 21st Century: New Perspectives for Diagnosis and Treatment of Arteriosclerosis," 51-56 (2000).
Robbins et al., "Blood Vessels" in *Pathologic Basis of Disease*, 6th ed., W. B. Saunders Company: Philadelphia, 498-510 (1999).
Rustan et al., *Journal of Lipid Research*, 29: 1417-1426 (1988).
Subauste et al., *Curr. Drug Targets Immune Endocr. Metabol. Disord.*, 3(4): 263-270 (2003).
Tomoda et al., *The Journal of Antibiotics*, 48(9): 937-941 (Sep. 1995).
Tomoda et al., *The Journal of Antibiotics*, 52(8): 689-694 (Aug. 1999).
Turkish et al., *J. Biol. Chem.*, 280(15): 14755-14764 (2005).
Vaziri et al., *Kidney Int.*, 66(1): 262-267 (2004).
Yu et al., *Hepatology*, 42(2): 362-371 (2005).

* cited by examiner

PYRROLO[1,2-B]PYRIDAZINE DERIVATIVES

CROSSED-REFERENCE TO RELATED APPLICATION

This application claims the benefit of Provisional Patent Application Ser. No. 60/493,997, filed Aug. 7, 2003, the content of which is incorporated by reference.

BACKGROUND OF THE INVENTION

Triglycerides represent the major form of energy stored in eukaryotes. Disorders or imbalances in triglyceride metabolism are implicated in the pathogenesis of and increased risk for obesity, insulin resistance syndrome and type II diabetes, nonalcoholic fatty liver disease and coronary heart disease (see, Lewis, et al, *Endocrine Reviews* (2002) 23:201 and Malloy and Kane, *Adv Intern Med* (2001) 47:111). Additionally, hypertriglyceridemia is often an adverse consequence of cancer therapy (see, Bast, et al. *Cancer Medicine*, 5th Ed., (2000) B. C. Decker, Hamilton, Ontario, Calif.).

A key enzyme in the synthesis of triglycerides is acyl CoA:diacylglycerol acyltransferase, or DGAT. DGAT is a microsomal enzyme that is widely expressed in mammalian tissues and that catalyzes the joining of 1,2-diacylglycerol and fatty acyl CoA to form triglycerides at the endoplasmic reticulum (reviewed in Chen and Farese, *Trends Cardiovasc Med* (2000) 10:188 and Farese, et al, *Curr Opin Lipidol* (2000) 11:229). It was originally thought that DGAT uniquely controlled the catalysis of the final step of acylation of diacylglycerol to triglyceride in the two major pathways for triglyceride synthesis, the glycerol phosphate and monoacylglycerol pathways. Because triglycerides are considered essential for survival, and their synthesis was thought to occur through a single mechanism, inhibition of triglyceride synthesis through inhibiting the activity of DGAT has been largely unexplored.

Genes encoding mouse DGAT1 and the related human homologs ARGP1 and ARGP2 now have been cloned and characterized (Cases, et al, *Proc Natl Acad Sci* (1998) 95:13018; Oelkers, et al, *J Biol Chem* (1998) 273:26765). The gene for mouse DGAT1 has been used to create DGAT knock-out mice to better elucidate the function of the DGAT gene. Unexpectedly, mice unable to express a functional DGAT enzyme (Dgat−/− mice) are viable and still able to synthesize triglycerides, indicating that multiple catalytic mechanisms contribute to triglyceride synthesis (Smith, et al, *Nature Genetics* (2000) 25:87). Other enzymes that catalyze triglyceride synthesis, for example, DGAT2 and diacylglycerol transacylase, also have been identified (Buhman, *J Biol Chem*, supra and Cases, et al, *J Biol Chem* (2001) 276:38870).

Significantly, Dgat−/− mice are resistant to diet-induced obesity and remain lean. Even when fed a high fat diet (21% fat) Dgat−/− mice maintain weights comparable to mice fed a regular diet (4% fat) and have lower total body triglyceride levels. The obesity resistance in Dgat−/− mice is not due to deceased caloric intake, but the result of increased energy expenditure and decreased resistance to insulin and leptin (Smith, et al, *Nature Genetics*, supra; Chen and Farese, *Trends Cardiovasc Med*, supra; and Chen, et al, *J Clin Invest* (2002) 109:1049). Additionally, Dgat−/− mice have reduced rates of triglyceride absorption (Buhman, et al, *J Biol Chem* (2002) 277:25474). In addition to improved triglyceride metabolism, Dgat−/− mice also have improved glucose metabolism, with lower glucose and insulin levels following a glucose load, in comparison to wild-type mice (Chen and Farese, *Trends Cardiovasc Med*, supra).

The finding that multiple enzymes contribute to catalyzing the synthesis of triglyceride from diacylglycerol is significant, because it presents the opportunity to modulate one catalytic mechanism of this biochemical reaction to achieve therapeutic results in an individual with minimal adverse side effects. Compounds that inhibit the conversion of diacylglycerol to triglyceride, for instance by specifically inhibiting the activity of the human homolog of DGAT1, will find use in lowering corporeal concentrations and absorption of triglycerides to therapeutically counteract the pathogenic effects caused by abnormal metabolism of triglycerides in obesity, insulin resistance syndrome and overt type II diabetes, congestive heart failure and atherosclerosis, and as a consequence of cancer therapy.

Because of the ever increasing prevalence of obesity, type II diabetes, heart disease and cancer in societies throughout the world, there is a pressing need in developing new therapies to effectively treat and prevent these diseases. Therefore there is an interest in developing compounds that can potently and specifically modulate a single catalytic mechanism of the enzymatic conversion of diacylglycerol to triglyceride. Of particular promise are compounds that specifically inhibit the catalytic activity of DGAT1 and its other mammalian homologs.

BRIEF SUMMARY OF THE INVENTION

The present invention provides fused bicyclic nitrogen-containing heterocyclic compounds that are useful for treating or preventing conditions and disorders associated with DGAT in animals, particularly humans.

In general, the compounds of the present invention are represented by the formula (I):

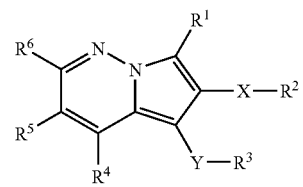

Turning first to the moieties pendant from five-membered ring in formula I, the letters X and Y represent divalent linkages independently selected from a single bond, $(C_1-C_4)$ alkylene, hetero$(C_2-C_4)$alkylene, —O—, —$CO_2$—, —$S(O)_k$—, —C(O)—, —$NR^7$—, —$C(O)NR^7$—, —$N(R^8)$ $C(O)NR^7$—, —$N(R^7)CO_2$—, —$SO_2NR^7$— and —$N(R^8)$ $SO_2NR^7$—, wherein the subscript k is an integer of from 0 to 2 and $R^7$ and $R^8$ are independently selected from H, $(C_1-C_8)$alkyl, aryl and aryl$(C_1-C_4)$alkyl.

The symbol $R^1$ represents H, halogen, $(C_1-C_8)$alkyl, $(C_2-C_8)$alkenyl, $(C_2-C_8)$alkynyl, fluoro$(C_1-C_8)$alkyl, cyclo$(C_3-C_8)$alkyl, hetero$(C_2-C_8)$alkyl, heterocyclo$(C_3-C_8)$alkyl, aryl, aryl$(C_1-C_4)$alkyl, heteroaryl, $OR^a$, $SR^a$, $C(O)R^a$, $CO_2R^a$, $C(O)NR^aR^b$, $SO_2R^a$, $SO_2NR^aR^b$, $NO_2$ or CN. The symbol $R^2$ represents a member selected from $(C_1-C_8)$alkyl, aryl$(C_1-C_4)$alkyl, $OR^a$, halogen, $NO_2$, $NR^aR^b$, CN and $W^1$, wherein $W^1$ is selected from

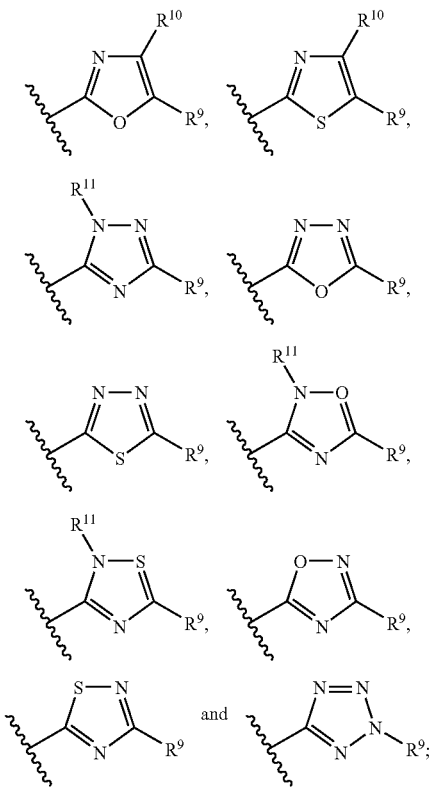

and optionally, R¹ and R² may be combined to form a 5-, 6- or 7-membered fused ring having 0 heteroatoms or 1 heteroatom selected from N, O and S. The symbol R³ represents H, $(C_1-C_8)$alkyl, aryl$(C_1-C_4)$alkyl, OR$^a$, halogen, NO$_2$, NR$^a$R$^b$, CN or W², wherein W² is selected from

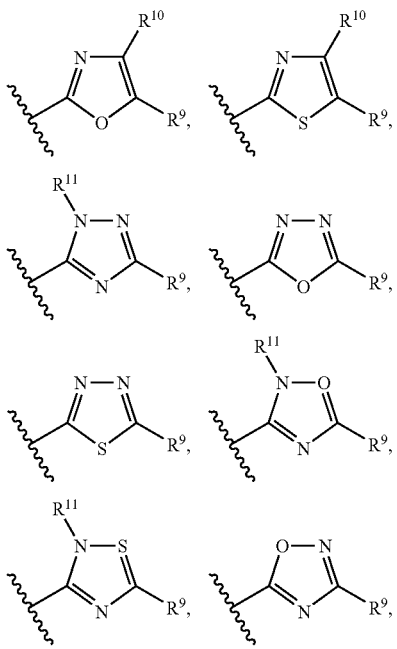

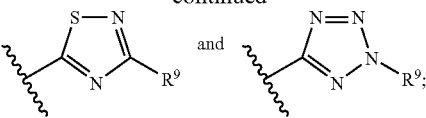

and optionally, R² and R³ may be combined to form a 5-, 6- or 7-membered fused ring having 0 heteroatoms or 1 heteroatom selected from N, O and S. However, R² and R³ are not both H.

The heterocyclic groups provided above have one or more R groups attached as shown. For compounds in which R² is W¹ and R³ is W², the attached R groups (R⁹, R¹⁰ and R¹¹) are each independent of one another and selected as follows: each R⁹ and R¹⁰ is independently selected from H, $(C_1-C_8)$alkyl, $(C_2-C_8)$alkenyl, $(C_2-C_8)$alkynyl, fluoro$(C_1-C_8)$alkyl, aryl and aryl$(C_1-C_4)$alkyl; or optionally, R⁹ and R¹⁰ may be combined to form a 5-, 6- or 7-membered fused ring containing 0, 1, 2 or 3 heteroatoms independently selected from N, O and S; and each R¹¹ is independently selected from H, $(C_1-C_8)$alkyl, aryl and aryl$(C_1-C_4)$alkyl.

Turning next to the groups pendant from the six-membered ring, the symbol R⁴ represents a member selected from $(C_1-C_8)$alkyl, $(C_2-C_8)$alkenyl, $(C_2-C_8)$alkynyl, fluoro$(C_1-C_4)$alkyl, hetero$(C_2-C_8)$alkyl, cyclo$(C_3-C_8)$alkyl, heterocyclo$(C_3-C_8)$alkyl, aryl, aryl$(C_1-C_4)$alkyl, heteroaryl, OR$^a$, SR$^a$, NR$^a$R$^b$, C(O)R$^a$, CO$_2$R$^a$, C(O)NR$^a$R$^b$, SO$_2$R$^a$ and SO$_2$NR$^a$R$^b$. The symbol R⁵ represents a member selected from H, $(C_1-C_8)$alkyl, fluoro$(C_1-C_8)$alkyl, cyclo$(C_3-C_8)$alkyl, hetero$(C_2-C_8)$alkyl, heterocyclo$(C_3-C_8)$alkyl, aryl, aryl$(C_1-C_4)$alkyl, heteroaryl, halogen, OR$^a$, NR$^a$R$^b$, CN, C(O)R$^a$, CO$_2$R$^a$, C(O)NR$^a$R$^b$, OC(O)R$^a$, OCO$_2$R$^c$, OC(O)NR$^a$R$^b$, NR$^a$C(O)R$^b$, NR$^a$CO$_2$R$^c$ and NR$^a$C(O)NR$^b$R$^a$. The symbol R⁶ represents a member selected from OR$^d$, NR$^d$R$^e$ and S(O)$_m$R$^d$ wherein the subscript m is an integer of from 0 to 2.

In the various groups provided above, the symbols R$^a$ and R$^b$ each independently represent in each occurrence H, $(C_1-C_8)$alkyl, cyclo$(C_3-C_8)$alkyl, aryl or aryl$(C_1-C_4)$alkyl. The symbol R$^c$ represents, in each occurrence, a member selected from $(C_1-C_8)$alkyl, cyclo$(C_3-C_8)$alkyl, aryl or aryl$(C_1-C_4)$alkyl. The symbols R$^d$ and R$^e$ are independently selected from H, $(C_1-C_8)$alkyl, $(C_2-C_8)$alkenyl, $(C_2-C_8)$alkynyl, fluoro$(C_1-C_8)$alkyl, C(O)R$^f$, aryl and aryl$(C_1-C_4)$alkyl; and optionally, R$^d$ and R$^e$ are combined to form a 4-, 5-, 6- or 7-membered ring with the nitrogen atom to which they are attached and 0, 1 or 2 additional heteroatoms independently selected from N, O and S. The symbol R$^f$ represents a member selected from H, $(C_1-C_8)$alkyl, amino, $(C_1-C_4)$alkylamino, $(C_1-C_4)$dialkylamino, aryl$(C_1-C_4)$alkyl and $(C_1-C_8)$alkoxy.

Unless otherwise indicated, the compounds provided in the above formula are meant to include all pharmaceutically acceptable salts, prodrugs or stereoisomers thereof.

The present invention also provides pharmaceutical compositions comprising a compound of the invention and a pharmaceutically acceptable carrier or excipient.

The present invention also provides methods for treating a disease or condition selected from the group consisting of obesity, diabetes, anorexia nervosa, bulimia, cachexia, syndrome X, insulin resistance, hyperglycemia, hyperuricemia, hyperinsulinemia, hypercholesterolemia, hyperlipidemia, dyslipidemia, mixed dyslipidemia, hypertriglyceridemia, nonalcoholic fatty liver disease, atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, vascular stenosis, solid tumors, skin cancer, melanoma, lymphoma, breast cancer, lung cancer, colorectal cancer, stomach cancer, esophageal cancer, pancreatic cancer, prostate cancer, kidney cancer, liver cancer, bladder cancer, cervical cancer, uterine cancer, testicular cancer and ovarian cancer, comprising administering to a subject in need thereof a therapeutically effective amount of a compound of the invention.

The present invention also provides methods for treating a disease or condition responsive to DGAT modulation, comprising administering to a subject in need thereof a therapeutically effective amount of a compound of the invention.

The present invention further provides methods for treating a DGAT-mediated condition or disease, comprising administering to a subject in need thereof a therapeutically effective amount of a compound of the invention.

The present invention further provides methods for modulating DGAT comprising contacting a cell with a compound of the invention.

BRIEF DESCRIPTION OF THE DRAWINGS

Not Applicable

DETAILED DESCRIPTION OF THE INVENTION

Abbreviations and Definitions

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

As used herein, "diabetes" refers to type I diabetes mellitus juvenile onset diabetes, insulin dependent-diabetes mellitus or IDDM) or type II diabetes mellitus (non-insulin-dependent diabetes mellitus or NIDDM), preferably, type II diabetes.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

As used herein, the term "obesity" refers to the excessive accumulation of body fat. Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Metabolic disorders, such as hyperlidemia and diabetes, and cardiovascular disorders, such as hypertension and coronary artery disease, are commonly associated with obesity.

The term "modulate" refers to the ability of a compound to increase or decrease the function, or activity, of DGAT. "Modulation", as used herein in its various forms, is intended to encompass antagonism, agonism, partial antagonism and/or partial agonism of the activity associated with DGAT. DGAT inhibitors are compounds that, e.g., bind to, partially or totally block stimulation, decrease, prevent, delay activation, inactivate, desensitize, or down regulate signal transduction. DGAT activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "DGAT" refers to the acyl CoA:diacylglycerol acyltransferase or a variant thereof, unless otherwise stated. DGAT variants include proteins substantially homologous to native DGAT, i.e., proteins having one or more naturally or non-naturally occurring amino acid deletions, insertions or substitutions (e.g., DGAT derivatives, homologs and fragments). The amino acid sequence of a DGAT variant preferably is at least about 80% identical to a native DGAT, more preferably at least about 90% identical, and most preferably at least about 95% identical.

As used herein, the term "DGAT-associated condition or disorder" refers to a condition or disorder associated with inappropriate, e.g., less than or greater than normal, DGAT activity and at least partially responsive to or affected by DGAT modulation (e.g., a DGAT inhibitor or antagonist results in some improvement in patient well-being in at least some patients). Inappropriate DGAT functional activity might arise as the result of DGAT expression in cells which normally do not express DGAT decreased DGAT expression or increased DGAT expression. A DGAT-associated condition or disorder may include a DGAT-mediated condition or disorder.

As used herein, the term "DGAT-mediated condition or disorder" and the like refers to a condition or disorder characterized by inappropriate, e.g., less than or greater than normal, DGAT activity. A DGAT-mediated condition or disorder may be completely or partially mediated by inappropriate DGAT activity. However, a DGAT-mediated condition or disorder is one in which modulation of DGAT results in some effect on the underlying condition or disease (e.g., a DGAT inhibitor or antagonist results in some improvement in patient well-being in at least some patients).

The term "alkyl," by itself or as part of another substituent, means, unless otherwise stated, a straight or branched chain, or cyclic hydrocarbon radical, or combination thereof, which is fully saturated, having the number of carbon atoms designated (i.e. $C_1$-$C_8$ means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. $C_2$-$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, $CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$.

Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., $C_3$-$C_8$ means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl" or "fluoroalkyl" are meant to include alkyl substituted with halogen atoms, which can be the same or different, in a number ranging from one to (2 m'+1), where m' is the total number of carbon atoms in the alkyl group. For example, the term "halo($C_1$-$C_4$)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2 m'+1) halogen atoms, where m' is the total number of carbon atoms in the alkyl group). The term "perhaloalkyl" means, unless otherwise stated, alkyl substituted with (2 m'+1) halogen atoms, where m' is the total number of carbon atoms in the alkyl group. For example the term "perhalo($C_1$-$C_4$)alkyl" is meant to include trifluoromethyl, pentachloroethyl, 1,1,1-trifluoro-2-bromo-2-chloroethyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term "heteroaryl" refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —OPO(OR')(OR"), —CN and —NO$_2$, in a number ranging from zero to three, with those groups having zero, one or two substituents being particularly preferred. R', R" and R'" each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO$_2$R', —NR'—C(O)NR"R'", —NR'—SO$_2$NR"R'", —NH—C(NH$_2$)=NH, —NR'C(NH$_2$)=NH, —NH—C(NH$_2$)=NR', —S(O)R', —SO$_2$R', —SO$_2$NR'R", NR'SO$_2$R, —N$_3$, —CH(Ph)$_2$, perfluoro(C$_1$-C$_4$)alkoxy and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl and (unsubstituted aryl)oxy-(C$_1$-C$_4$)alkyl. When the aryl group is 1,2,3,4-tetrahydronaphthalene, it may be substituted with a substituted or unsubstituted (C$_3$-C$_7$)spirocycloalkyl group. The (C$_3$-C$_7$)spirocycloalkyl group may be substituted in the same manner as defined herein for "cycloalkyl". Typically, an aryl or heteroaryl group will have from zero to three substituents, with those groups having two or fewer substituents being preferred in the present invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C$_1$-C$_4$)alkoxy and perfluoro(C$_1$-C$_4$)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C$_1$-C$_4$)alkoxy and perfluoro(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

It is to be understood that the substituent —CO$_2$H, as used herein, includes bioisosteric replacements therefor, such as:

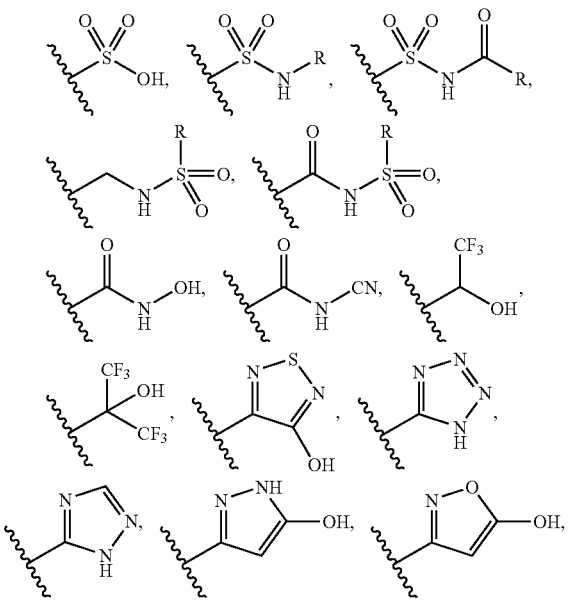

-continued

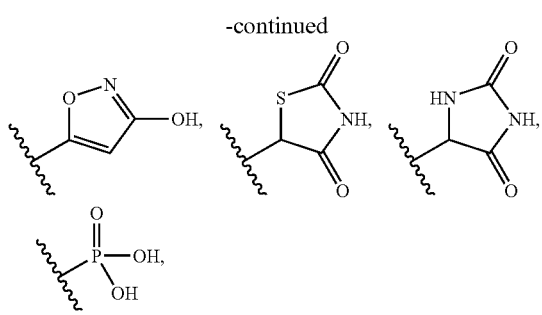

and the like. See, e.g., *The Practice of Medicinal Chemistry*; Wermuth, C. G., Ed.; Academic Press: New York, 1996; p. 203.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

It is to be understood that when a compound of the invention contains one or more asymmetric carbon atoms (optical centers) or double bonds, the present invention includes individual stereoisomers and geometric isomers as well as mixtures thereof.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

EMBODIMENTS OF THE INVENTION

Compounds

In one aspect, the present invention provides compounds of formula (I):

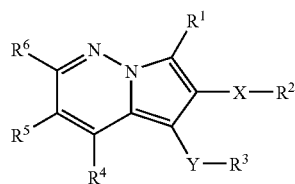

or a pharmaceutically acceptable salt or prodrug thereof, wherein X and Y are divalent linkages independently selected from the group consisting of a single bond, ($C_1$-$C_4$)alkylene, hetero($C_2$-$C_4$)alkylene, —O—, —$CO_2$—, —S(O)$_k$—, —C(O)—, —$NR^7$—, —C(O)$NR^7$—, —N($R^8$)C(O)$NR^7$—, —N($R^7$)$CO_2$—, —$SO_2NR^7$— and —N($R^8$)$SO_2NR^7$—.

$R^1$ is selected from the group consisting of H, halogen, ($C_1$-$C_8$)alkyl, ($C_2$-$C_8$)alkenyl, ($C_2$-$C_8$)alkynyl, fluoro($C_1$-$C_8$)alkyl, cyclo($C_3$-$C_8$)alkyl, hetero($C_2$-$C_8$)alkyl, heterocyclo($C_3$-$C_8$)aryl, aryl($C_1$-$C_4$)alkyl, heteroaryl, $OR^a$, $SR^a$, C(O)$R^a$, $CO_2R^a$, C(O)$NR^aR^b$, $SO_2R^a$, $SO_2NR^aR^b$, $NO_2$ and CN.

$R^2$ is selected from the group consisting of ($C_1$-$C_8$)alkyl, aryl($C_1$-$C_4$)alkyl, $OR^a$, halogen, $NO_2$, $NR^aR^b$, CN and $W^1$, wherein $W^1$ is selected from the group consisting of

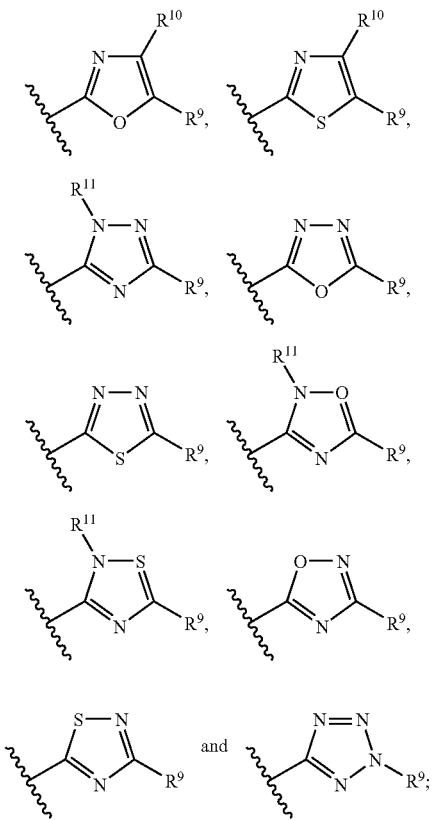

and optionally, $R^1$ and $R^2$ are combined to form a 5-, 6- or 7-membered fused ring having 0 heteroatoms or 1 heteroatom selected from the group consisting of N, O and S.

$R^3$ is selected from the group consisting of H, $(C_1-C_8)$ alkyl, aryl$(C_1-C_4)$alkyl, $OR^a$, halogen, $NO_2$, $NR^aR^b$, CN and $W^2$, wherein $W^2$ is selected from the group consisting of

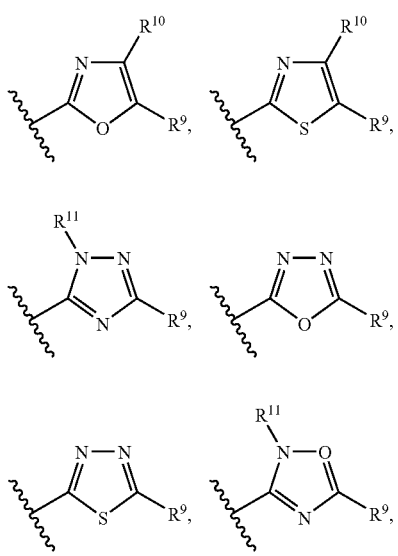

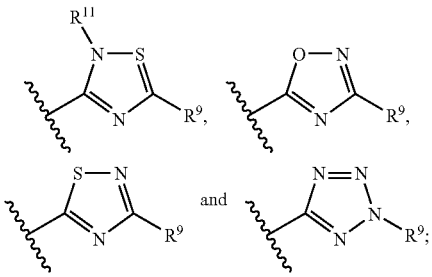

and optionally, $R^2$ and $R^3$ are combined to form a 5-, 6- or 7-membered fused ring containing 0 heteroatoms or 1 heteroatom selected from the group consisting of N, O and S.

$R^4$ is selected from the group consisting of $(C_1-C_8)$alkyl, $(C_2-C_8)$alkenyl, $(C_2-C_8)$alkynyl, fluoro$(C_1-C_4)$alkyl, hetero$(C_2-C_8)$alkyl, cyclo$(C_3-C_8)$alkyl, heterocyclo$(C_3-C_8)$alkyl, aryl, aryl$(C_1-C_4)$alkyl, heteroaryl, $OR^a$, $SR^a$, $NR^aR^b$, $C(O)R^a$, $CO_2R^a$, $C(O)NR^aR^b$, $SO_2R^a$ and $SO_2NR^aR^b$.

$R^5$ is selected from the group consisting of H, $(C_1-C_8)$alkyl, fluoro$(C_1-C_8)$alkyl, cyclo$(C_3-C_8)$alkyl, hetero$(C_2-C_8)$alkyl, heterocyclo$(C_3-C_8)$alkyl, aryl, aryl$(C_1-C_4)$alkyl, heteroaryl, halogen, $OR^a$, $NR^aR^b$, CN, $C(O)R^a$, $CO_2R^a$, $C(O)NR^aR^b$, $OC(O)R^a$, $OCO_2R^c$, $OC(O)NR^aR^b$, $NR^aC(O)R^b$, $NR^aCO_2R^c$ and $NR^aC(O)NR^bR^a$.

$R^6$ is selected from the group consisting of $OR^d$, $NR^dR^e$ and $S(O)_mR^d$.

$R^7$ and $R^8$ are independently selected from the group consisting of H, $(C_1-C_8)$alkyl, aryl and aryl$(C_1-C_4)$alkyl.

Each $R^9$ and $R^{10}$ is independently selected from the group consisting of H, $(C_1-C_8)$alkyl, $(C_2-C_8)$alkenyl, $(C_2-C_8)$alkynyl, fluoro$(C_1-C_8)$alkyl, aryl and aryl$(C_1-C_4)$alkyl; or optionally, $R^9$ and $R^{10}$ are combined to form a 5-, 6- or 7-membered fused ring containing 0, 1, 2 or 3 heteroatoms independently selected from the group consisting of N, O and S.

Each $R^{11}$ is independently selected from the group consisting of H, $(C_1-C_8)$alkyl, aryl and aryl$(C_1-C_4)$alkyl.

In each of the groups above, the symbols $R^a$ and $R^b$ are each independently members selected from H, $(C_1-C_8)$alkyl, cyclo$(C_3-C_8)$alkyl, aryl and aryl$(C_1-C_4)$alkyl. $R^c$ is a member selected from $(C_1-C_8)$alkyl, cyclo$(C_3-C_8)$alkyl, aryl and aryl$(C_1-C_4)$alkyl. The symbols $R^d$ and $R^e$ represent members independently selected from H, $(C_1-C_8)$alkyl, $(C_2-C_8)$alkenyl, $(C_2-C_8)$alkynyl, fluoro$(C_1-C_8)$alkyl, $C(O)R^f$, aryl and aryl$(C_1-C_4)$alkyl; or optionally, $R^d$ and $R^e$ are combined to form a 4-, 5-, 6- or 7-membered ring containing the nitrogen atom to which they are attached and 0, 1 or 2 additional heteroatoms independently selected from the group consisting of N, O and S. $R^f$ is a member selected from H, $(C_1-C_8)$alkyl, amino, $(C_1-C_4)$alkylamino, $(C_1-C_4)$dialkylamino, aryl$(C_1-C_4)$alkyl and $(C_1-C_8)$alkoxy.

The subscripts k and m are independently 0, 1 or 2.

In one group of preferred embodiments, $R^4$ is a substituted or unsubstituted phenyl. In still further preferred embodiments, the compound is represented by formula (II):

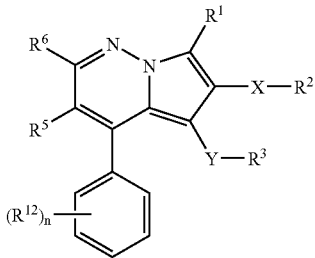

II wherein each $R^{12}$ is selected from the group consisting of $(C_1-C_4)$alkyl, fluoro$(C_1-C_8)$alkyl, halogen and aryl; and the subscript n is 0, 1, 2 or 3. The remaining R groups have the meaning provided above with reference to formula (I).

In another group of preferred embodiments, based on formula (I), $R^6$ is $NR^dR^e$. Still further preferred are those embodiments in which $R^6$ is selected from the group consisting of azetidinyl, pyrrolyl, pyrrolidinyl, imidazolyl, triazolyl, piperidinyl, morpholinyl, piperazinyl and indolyl. Each of these heterocyclic moieties can be substituted or unsubstituted. In a still further preferred group of embodiments, the compounds are represented by formula (III):

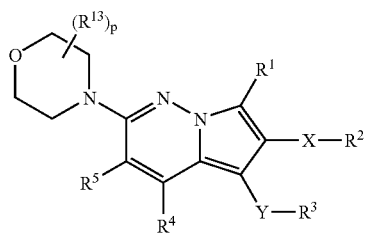

III wherein each $R^{13}$ is selected from the group consisting of $(C_1-C_4)$alkyl, fluoro$(C_1-C_8)$alkyl, halogen and aryl; and the subscript p is 0, 1, 2 or 3. The remaining R groups, X and Y have the meanings provided above with reference to formula (I).

In another further preferred group of embodiments, with reference to formula (I), $R^4$ is a substituted or unsubstituted phenyl, and $R^6$ is $NR^dR^e$. Still further preferred in this group of embodiments are those compounds represented by formula (IV):

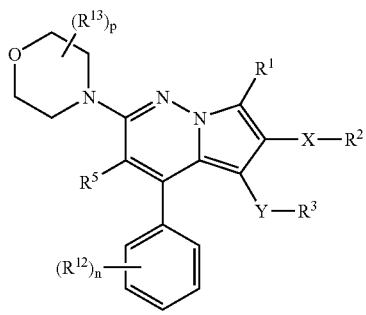

IV wherein each $R^{12}$ and $R^{13}$ is selected from the group consisting of $(C_1-C_4)$alkyl, fluoro$(C_1-C_8)$alkyl, halogen and aryl; and the subscripts n and p are independently 0, 1, 2 or 3. The remaining R groups, X and Y have the meanings provided above with reference to formula (I).

In one group of further preferred embodiments for the compounds of formula (IV) are those compounds in which $R^5$ is H or halogen. Even further preferred are those compounds in which $R^1$ is selected from H, $(C_1-C_8)$alkyl, $(C_2-C_8)$alkenyl, fluoro$(C_1-C_8)$alkyl, cyclopropyl, cyclobutyl, cyclopentyl, cyclohexyl, phenyl, pyridyl and benzyl. In still further preferred embodiments, $R^1$ and $R^2$ are combined to form a 5- or 6-membered fused ring having a nitrogen or oxygen atom as a ring member.

In another group of further preferred embodiments for the compounds of formula (IV) are those compounds in which X and Y are independently selected from a single bond, $(C_1-C_4)$alkylene, —C(O)—, —$CO_2$—, —$N(R^7)C(O)$— and —$N(R^7)CO_2$—. Still further preferred are those compounds in which X and Y are independently selected from a single bond, $(C_1-C_4)$alkylene, and —$CO_2$—, $R^2$ is selected from $(C_1-C_8)$alkyl, aryl$(C_1-C_4)$alkyl, $OR^a$ and $W^1$, and $R^3$ is selected from $(C_1-C_8)$alkyl, aryl$(C_1-C_4)$alkyl, $OR^a$ and $W^2$. In certain further preferred embodiments are those compounds in which X and Y are —$CO_2$—, and $R^2$ and $R^3$ are independently selected from $(C_1-C_8)$alkyl and aryl$(C_1-C_4)$alkyl. In other further preferred embodiments, X is a single bond, Y is selected from a single bond, $(C_1-C_4)$alkylene, and —$CO_2$—, and $R^2$ is $W^1$.

The most preferred compounds of the present invention are those that are provided in the examples below.

Preparation of Compounds

Compounds of the present invention can be prepared beginning with commercially available starting materials and using general synthetic techniques known to those of skill in the art. Outlined below are reaction schemes suitable for preparing such compounds. Further exemplification is found in the specific Examples provided.

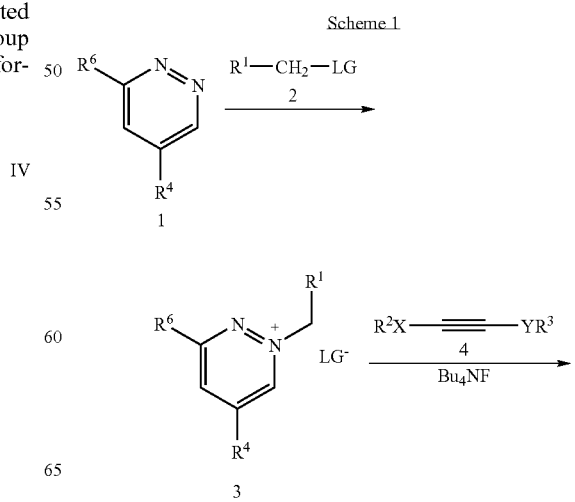

Scheme 1

-continued

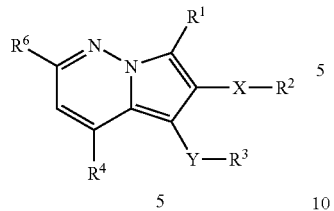

As shown in Scheme 1, compounds of the present invention wherein $R^5 Z^1$ is H, can be prepared by reacting a suitably substituted pyridazinium salt (3) with an acetylene derivative (4). Condensation of 3 and 4 in an organic solvent or mixture of solvents (including aqueous mixtures) in the presence of a base (e.g., tetrabutyl ammonium fluoride) provides, after workup, pyrrolopyridazine 5. Pyridazinium salt 3 can, in turn, be obtained by treatment of a suitably substituted pyridazine (1) with an alkylating agent (2), wherein LG indicates a leaving group such as halide, toluenesulfonate, methanesulfonate or trifluoromethanesulfonate, in an organic solvent or mixture of solvents. Pyridazine 1 can be obtained by a variety of methods, as illustrated in Schemes 2-4.

In Scheme 2, a substituted or unsubstituted arylacetonitrile (6) is condensed with glyoxylic acid under basic conditions to provide the corresponding 3-aryl-3-cyanopropenoate 7. Subjecting 7 to acids such as HCl or $H_2SO_4$/$HCO_2H$ results in the formation of maleic anhydride 8 (see, e.g., Dean et al. (1993) *J. Org. Chem.* 58:7916-7917). Treatment of 8 with hydrazine results in the formation of 4-arylpyridazine-3,6-diol 9, which can be converted into 4-aryl-3,6-dichloropyridazine 10 by treatment with a chlorinating reagent such as $POCl_3$, $PCl_3$, $PCl_5$ or $SOCl_2$. Compound 10 can be treated with a nucleophile, e.g., an amine, to provide 11. Catalytic Scheme 2

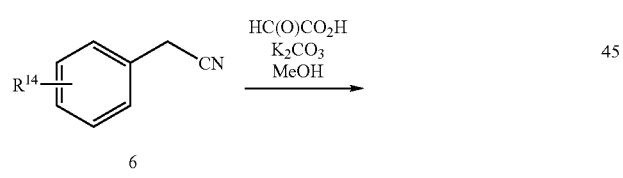

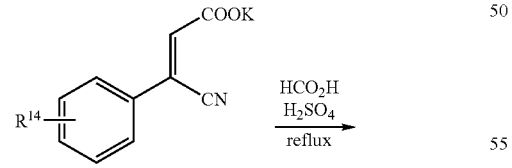

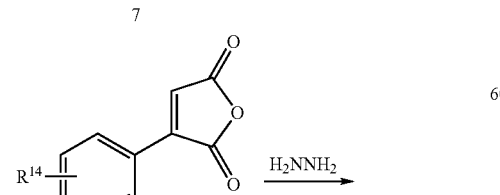

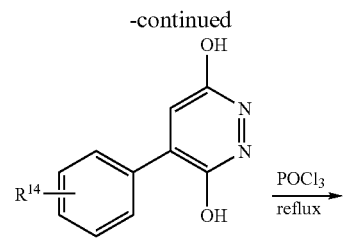

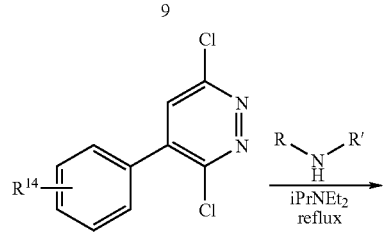

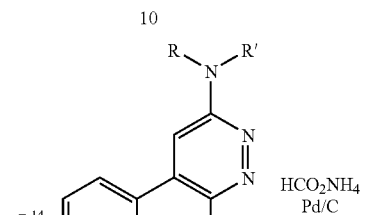

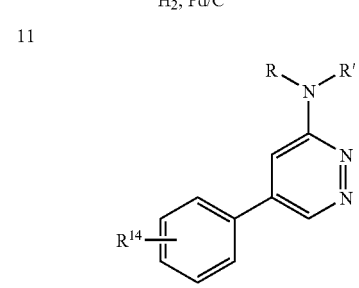

hydrogenation of 11 using, for example, a palladium or platinum catalyst in a relatively polar solvent such as THF, methanol or an aqueous mixture containing an alcohol or THF as a co-solvent, for example, can be used to remove the halogen atom, producing 12. Scheme 3 illustrates similar methods that can be used to convert 10 into oxygen-substituted derivatives 14.

Scheme 3

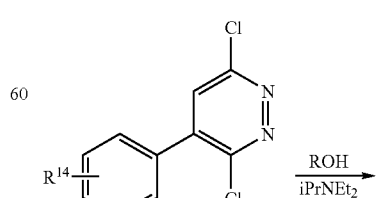

-continued

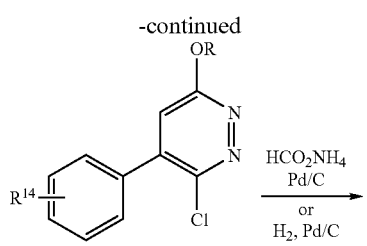
14

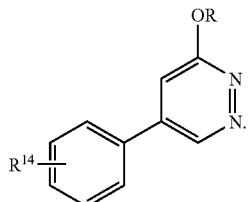
20

Other approaches can be used to obtain alkyl-substituted pyridazines, as depicted in Scheme 4. For example, 3,6-dichloropyridazine (15) can be alkylated in aqueous sulfuric acid with silver (I) peroxydisulfate in the presence of a carboxylic acid to afford alkylated dichloropyridazine 16 (see, e.g., Samaritoni (1988) *Org. Prep. Proced. Int.* 20:117). Transformation of 16 into the 3-amino-5-alkylpyridazine 18 can be accomplished as described above for the transformation of dichloropyridazine 10 into 3-amino-5-aryl-pyridazine 12. Similarly, 16 can be converted into the ether derivative 20 as described above for the conversion of 10 into 14.

As shown in Schemes 5-8, compounds such as diester 21 can be used to prepare compounds of the invention by, for example, hydrolysis of one or both ester groups to provide carboxylic acids such as 22 or 23 (Scheme 5). Ester hydrolysis can be accomplished in most solvents that will dissolve 21 and are at least partially miscible with water, by treating a solution of 21 with aqueous base such as lithium, sodium or potassium hydroxide.

Scheme 5

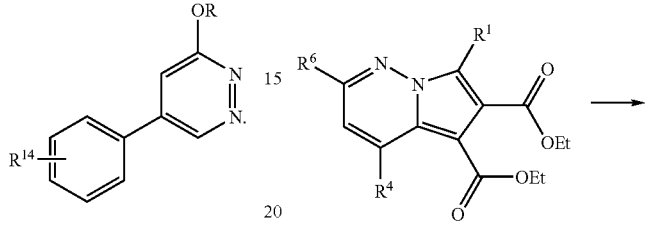
21

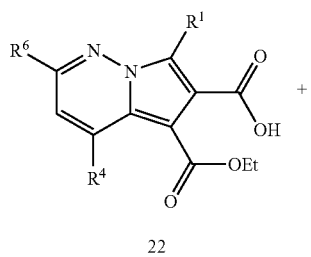
22

Scheme 4

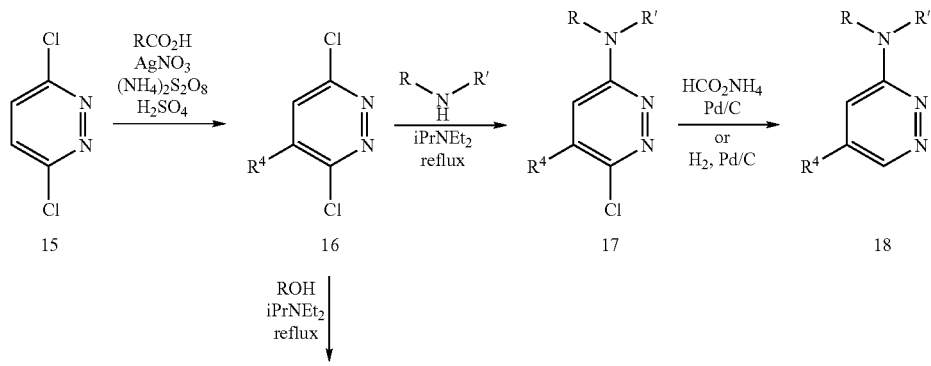

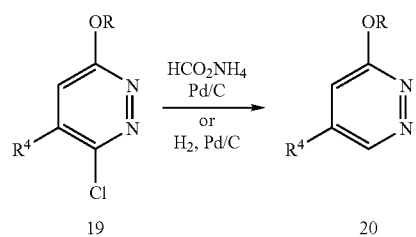

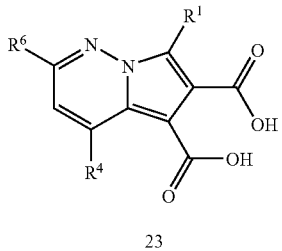

23

The carboxylic acid can, in turn, be converted into other groups by methods well known to those of ordinary skill in the art. Scheme 6 illustrates one method for the conversion of acid 22 to a carbamate (25). One of skill in the art will understand that other methods can be employed to prepare related compounds of the invention. For example, carboxylic acid 22 can be converted to amine 24 via a Curtius rearrangement (see, e.g., March, J. *Advanced Organic Chemistry*, 4th ed.; John Wiley & Sons: New York, 1992; pp 1091-1092). Treatment of 24 with a chloroformate in the presence of base (typically a tertiary amine) produces carbamate 25.

Carboxylic acid 22 can be activated by condensation with a variety of coupling reagents, including hydroxybenzotriazole (HOBt) and N-hydroxysuccinimide (HOSu), for example, using dicyclohexylcarbodiimide (DCC) or a similar carbodiimide reagent, or a wide variety of reagents such as those developed for formation of peptide bonds. Conditions for such reactions are well known to those of ordinary skill in the art. The activated intermediate, an ester of HOBt or HOSu, for example, can be condensed with a wide variety of nucleophiles, for example, amines, alcohols and thiols, to produce other esters, thioesters or amides. Scheme 6 shows the conversion of acid 22 into amide 26 by this sequence, using ammonia as the nucleophile. Dehydration of amide 26 can be accomplished by a variety of methods. Phosphorous pentoxide is the most common dehydrating reagent for this reaction, but many others are known to those skilled in the art. Nitrile 27 can be converted into other groups such as a tetrazole (28) by methods well known to those of ordinary skill in the art. For example, reacting the nitrile with an azide, such as sodium or lithium azide, or hydrazoic acid in a solvent such as DMF or water will accomplish this transformation.

Scheme 6

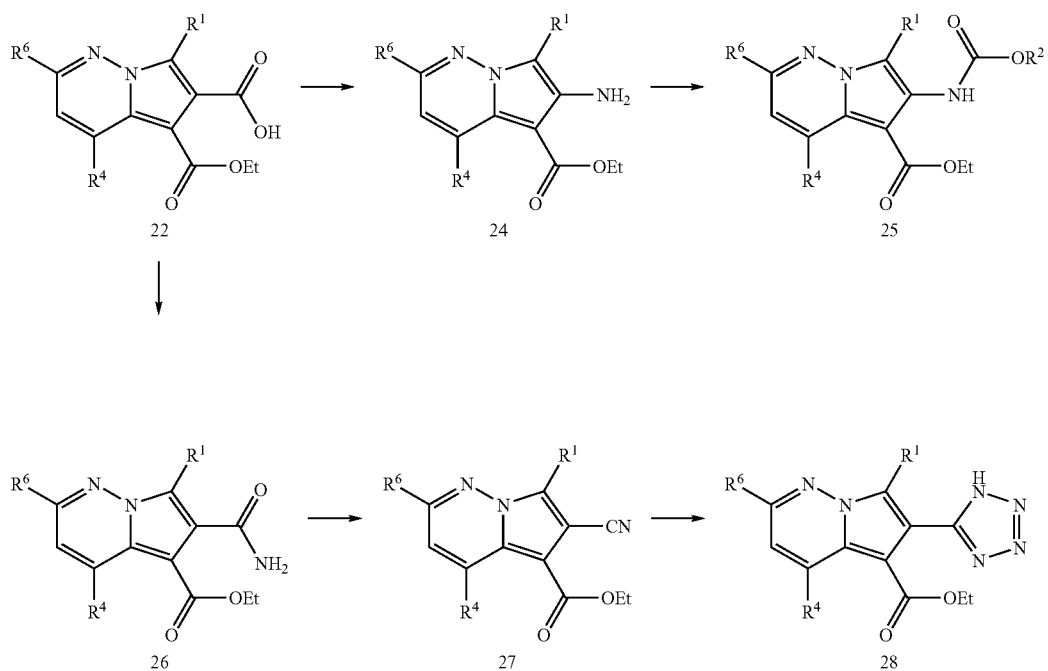

Additional examples of the conversion of 22 into other compounds are shown in Scheme 7.

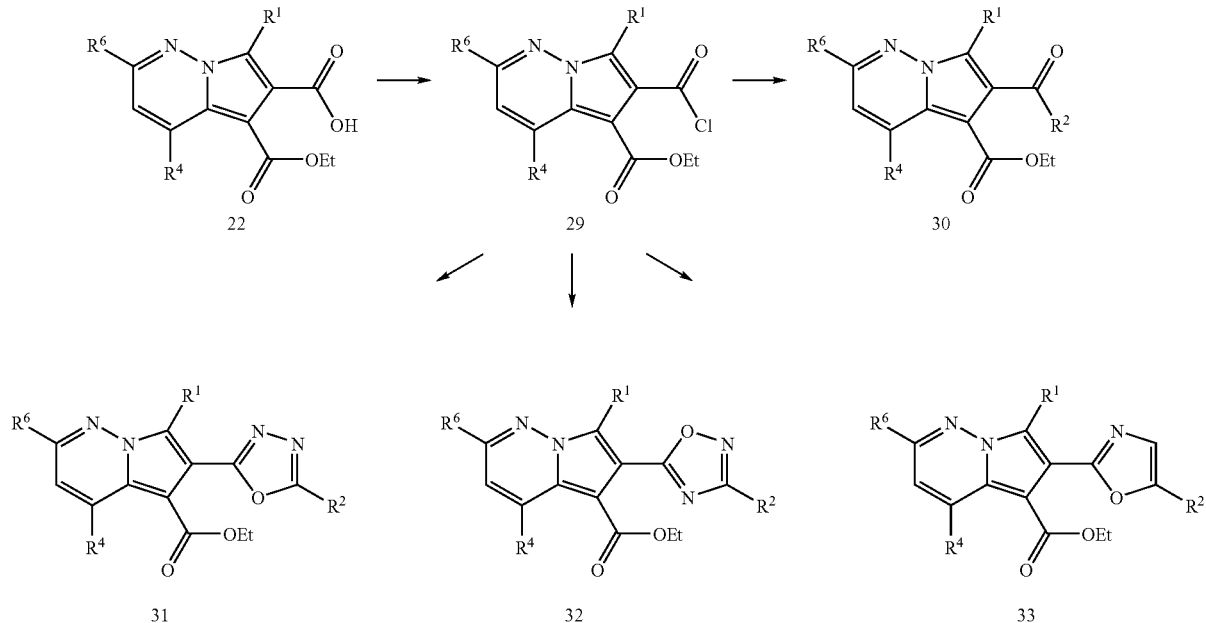

Transformation of 22 into acid chloride 29 can be accomplished using reagents such as oxalyl chloride, POCl$_3$, PCl$_3$, PCl$_5$ or SOCl$_2$. Acid chloride 29 can be treated with, for example, a lithium dialkylcopper reagent to give ketone 30. Acid chloride 29 can also be used to produce heterocyclic derivatives such as [1,3,4]-oxadiazoles (31), [1,2,4]-oxadiazoles (32) and oxazoles (33) using methods known to those of ordinary skill in the art. For example, reacting acid chloride 29 with an acyl hydrazide in the presence of a base such as triethylamine, followed by treatment with P$_4$O$_{10}$ at elevated temperature will accomplish the transformation into 31. In another example, 29 can be reacted with an N-hydroxyamidine derivative in the presence of a base, and the product treated with tetrabutyl ammonium fluoride to give 32. In yet another example, 29 can be treated with an α-aminoketone in the presence of a base such as triethylamine or pyridine, and subsequently subjected to dehydrating conditions such as sulfuric acid, P$_4$O$_{10}$ or PPh$_3$-diethyl azodicarboxylate to produce 33.

Still other compounds of this invention can be prepared from ester 21 as illustrated in Scheme 8. For example, reduction of 21 with a reagent such as LiAlH$_4$ or LiBEt$_3$H in a suitable solvent (e.g., THF, diethylether or dimethoxyethane) produces alcohol 34. Alcohol 34 can be alkylated or acylated by methods known to the skilled practitioner to give 35 or 36, respectively.

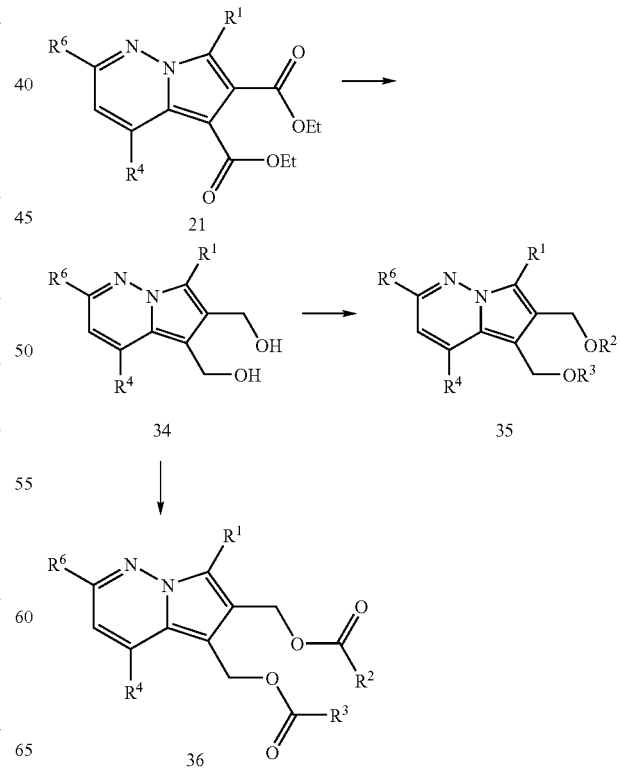

Compositions

In another aspect, the present invention provides pharmaceutical compositions for modulating DGAT activity in humans and animals that will typically contain a compound of formula I and a pharmaceutically acceptable carrier or diluent.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, patches, creams, ointments, jellies, solutions or suspensions, etc., containing the compounds of the present invention are employed. As used herein, topical application is also meant to include the use of mouth washes and gargles.

The pharmaceutical composition and method of the present invention may further comprise other therapeutically active compounds as noted herein which are usually applied in the treatment of the above-mentioned pathological conditions.

Methods of Use

In yet another aspect, the present invention provides methods of using a compound or composition of the invention to treat or prevent a disease or condition associated with DGAT. Diseases and conditions associated with lipid metabolism and cell proliferation, and complications thereof, can be treated with the subject compounds and compositions. In one group of embodiments, diseases and conditions, including chronic diseases, of humans or other species that can be treated with inhibitors of DGAT function include, but are not limited to, metabolic disorders, such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis and vascular stenosis; neoplastic diseases, such as solid tumors, skin cancer, melanoma, lymphoma and endothelial cancers, e.g., breast cancer, lung cancer, colorectal cancer, stomach cancer, other cancers of the gastrointestinal tract (e.g., esophageal cancer and pancreatic cancer), prostate cancer, kidney cancer, liver cancer, bladder cancer, cervical cancer, uterine cancer, testicular cancer and ovarian cancer; skin disorders typically associated with sebaceous glands such as acne (including open comedos and whiteheads), deep acne, acne conglobata, acne rosacea, comedos, cysts, microcomedos, acne vulgaris, rosacea, perioral dermatitis, sebaceous cysts, primary seborrhea, secondary seborrhea, and alopecia; and other diseases and conditions that are sensitive or responsive to modulation of DGAT function.

The methods of the present invention typically involve administering to a subject in need of therapeutic treatment, an effective amount of a compound of formula (I). The dose, frequency and timing of such administering will depend in large part on the selected therapeutic agent, the nature of the condition being treated, the condition of the subject including age, weight and presence of other conditions or disorders, the formulation being administered and the discretion of the attending physician. Preferably, the compositions and compounds of the invention and the pharmaceutically acceptable salts thereof are administered via oral, parenteral or topical routes. Generally, the compounds are administered in dosages ranging from about 2 mg up to about 2,000 mg per day, although variations will necessarily occur depending, as noted above, on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. The dosage employed for the topical administration will, of course, depend on the size of the area being treated.

Combination Therapy with Additional Active Agents

The present invention further provides methods of using a compound or composition of the invention in combination with one or more additional active agents, depending on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W., (ed.), CURRENT THERAPY IN ENDOCRINOLOGY AND METABOLISM, $6^{th}$ Edition (Mosby—Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al., *Diabet. Med.* (1996) 13 365-370; Kwiterovich, P. *Am. J. Cardiol* (1998) 82 (12A): 3U-17U).

In particular, the studies provided above indicate that diabetes and hyperlipidemia modulation can be further improved in many instances by the addition of a second agent to the therapeutic regimen. Combination therapy includes administration of a single pharmaceutical dosage formulation which contains a compound having the general structure of formula I and one or more additional active agents, as well as administration of a compound of formula I and each active agent in its own separate pharmaceutical dosage formulation. For example, a compound of formula I and an HMG-CoA reductase inhibitor can be administered to the human subject together in a single oral dosage composition, such as a tablet or capsule, or each agent can be administered in separate oral dosage formulations. Where separate dosage formulations are used, a compound of formula I and one or more additional active agents can be administered at essentially the same time (i.e., concurrently), or at separately staggered times (i.e., sequentially). Combination therapy is understood to include all these regimens.

An example of combination therapy that modulates (prevents the onset of the symptoms or complications associated with) atherosclerosis involves administering a compound of formula I in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the compounds of formula I can be administered in combination with more than one additional active agent, for example, a combination of a compound of formula I with an HMG-CoA reductase inhibitor (e.g., lovastatin, simvastatin and pravastatin) and aspirin, or a compound of formula I with an HMG-CoA reductase inhibitor and a β blocker.

Another example of combination therapy can be seen in treating obesity or obesity-related disorders, wherein the compounds of formula I can be effectively used in combination with, for example, phenylpropanolamine, phentermine, diethylpropion, mazindol; fenfluramine, dexfenfluramine, phentiramine, β$_3$ adrenoceptor agonist agents; sibutramine, gastrointestinal lipase inhibitors (such as orlistat), and leptins. Other agents used in treating obesity or obesity-related disorders can be used in combination with compounds of formula I including, for example, neuropeptide Y, enterostatin, cholecytokinin, bombesin, amylin, histamine H$_3$ receptors, dopamine D$_2$ receptors, melanocyte stimulating hormone, corticotrophin releasing factor, galanin and gamma amino butyric acid (GABA).

Another example of combination therapy can be seen in modulating diabetes (or treating diabetes and its related symptoms, complications, and disorders), wherein the compounds of formula I can be effectively used in combination with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); dehydroepiandrosterone (also referred to as DHEA or its conjugated sulphate ester, DHEA-SO$_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

Still another example of combination therapy can be seen in modulating hyperlipidemia (treating hyperlipidemia and its related complications), wherein the compounds of formula I can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E, or vitamin C.

In accordance with the present invention, a therapeutically effective amount of a compound of formula I can be used for the preparation of a pharmaceutical composition useful for treating diabetes, treating hyperlipidemia, treating hyperuricemia, treating obesity, lowering triglyceride levels, lowering cholesterol levels, raising the plasma level of high density lipoprotein, and for treating, preventing or reducing the risk of developing atherosclerosis.

A further example of combination therapy can be seen in modulating dermatological conditions, wherein compounds of formula I can be effectively used in combination with, for example, acne treatments (e.g., isotretinoin, doxycycline, tetracycline, salicylate) and seborrheic dermatitis treatments (antifungal agents such as climbazole, ketoconazole). Moreover, compounds of formula I can be effectively used to enhance the transdermal delivery of drugs applied topically in the form of a patch, lotion, jellies, cream, etc.

Still another example of combination therapy can be seen in treating nonalcoholic fatty liver disease (NAFLD), wherein compounds of formula I can be effectively used in combination with hepatoprotective agents such as ursodeoxycholic acid and betaine.

Additionally, an effective amount of a compound of formula I and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozil; vitamin B$_6$ and the pharmaceutically acceptable salts thereof; vitamin B$_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, β$_3$ adrenergic receptor agonists; sulfonylureas, biguanides, α-glucosidase inhibitors, other insulin secretogogues, insulin and a hepatoprotective agent can be used together for the preparation of a pharmaceutical composition useful for the above-described treatments.

EXAMPLES $^1$H-NMR spectra were recorded on a Varian Gemini 400 MHz or Bruker Avance 500 MHz NMR spectrometer. Significant peaks are tabulated and typically include: number of protons, multiplicity (s, singlet; d, doublet; t, triplet; q, quartet; m, multiplet; br s, broad singlet) and coupling constant(s) in Hertz. Mass spectrometry results are reported as the ratio of mass over charge, followed by the relative abundance of each ion (in parentheses). Starting materials in the synthesis examples below are either available from commercial sources such as Aldrich Chemical Co., Milwaukee, Wis., USA, or via literature procedures. Abbreviations used in the examples below have their accepted meanings in the chemical literature. For example, THF (tetrahydrofuran), Et$_2$O (diethyl ether), MeOH (methanol), LDA (lithium diisopropylamide), MeCN (acetonitrile), DMAP (4-dimethyaminopyridine), WSC (1-ethyl-3-(3'-dimethylaminopropyl)carbodiimide), HOBt (1-hydroxybenzotriazole), DBU (1,8-diazabicyclo[5.4.0]undec-7-ene), DME (1,2-dimethoxyethane), DMF (N,N-dimethylformamide), DMSO (dimethyl sulfoxide), AcOH (acetic acid) and AcOEt (ethyl acetate).

Example 1

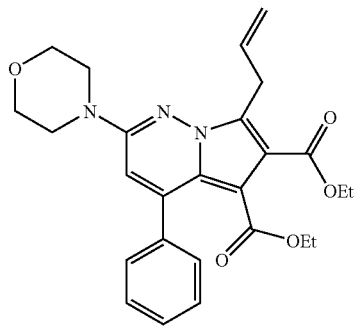

7-Allyl-2-morpholin-4-yl-4-phenylpyrrolo[1,2-b]
pyridazine-5,6-dicarboxylic acid diethyl ester (1)

Step A. 4-Phenyl-pyridazine-3,6-diol. Phenyl maleic anhydride (20 g, 0.115 mol) was added to a solution of hydrazine monohydrochloride (15.7 g, 0.230 mol) in 80% aqueous EtOH (400 mL). The reaction mixture was heated at reflux for 20 h. The solution was cooled to 0° C. and the resulting precipitate was collected by vacuum filtration and washed with cold EtOH (100 mL) to provide the title compound as a white solid. $^1$H NMR (DMSO-$d_6$) δ 7.17 (s, 1H), 7.43 (m, 5H). Mass Spectrum (ESI+) m/e=189.1 (M+H).

Step B. 3,6-Dichloro-4-phenylpyridazine. 4-Phenyl-1,2-dihydropyridazine-3,6-dione (19 g) was added to 50 mL of POCl$_3$. The reaction mixture was heated at reflux for 4 h and added dropwise to 300 mL of ice water. The resulting precipitate was collected by vacuum filtration to provide the title compound. $^1$H NMR (CDCl$_3$) δ 7.48-7.55 (m, 6H). Mass Spectrum (ESI+) m/e=225.0 (M+H).

Step C. 4-(6-Chloro-5-phenylpyridazin-3-yl)morpholine. 3,6-Dichloro-4-phenylpyridazine (9.0 g) was added to a solution of diisopropylethyl amine (9.39 mL, 53.9 mmol) in dioxane (200 mL). Morpholine (3.60 mL, 41.3 mmol) was added and the reaction mixture was heated at reflux for 18 h. The solvent was removed in vacuo and replaced with EtOAc (600 mL). The solution was washed with water, brine, dried (MgSO$_4$), filtered, and concentrated in vacuo to provide the title compound. $^1$H NMR (DMSO-$d_6$) δ 3.60 (m, 4H), 3.71 (m, 4H), 7.34 (s, 1H), 7.54 (m, 5H). Mass Spectrum (ESI+) m/e=276.1 (M+H).

Step D. 4-(5-Phenylpyridazin-3-yl)morpholine. A mixture of 4-(6-Chloro-5-phenylpyridazin-3-yl)morpholine (9.91 g, 35.9 mmol), HCO$_2$NH$_4$ (22.7 g, 0.359 mol), and 10% Pd/C (2 g) in MeOH (200 mL) was heated at 48° C. for 16 h. The reaction mixture was filtered through celite and the filtrate was concentrated in vacuo to provide a yellow solid. The solid was dissolved in CH$_2$Cl$_2$ and washed with water, dried over MgSO$_4$, filtered, and concentrated in vacuo to provide a yellow solid. The title compound was obtained by recrystallization from EtOAc/hexane. $^1$H NMR (DMSO-$d_6$) δ 3.75 (s, 8H), 7.64 (m, 3H), 8.01 (m, 2H), 8.23 (s, 1H), 9.63 (s, 1H). Mass Spectrum (ESI+) m/e=242.2 (M+H).

Step E. 1-But-3-enyl-3-morpholin-4-yl-5-phenylpyridazin-1-ium bromide. A solution of 4-(5-Phenylpyridazin-3-yl)morpholine (200 mg, 0.829 mmol) and 4-bromo-1-butene (252 μL, 2.49 mmol) in CH$_3$CN (30 mL) was heated at reflux for 12 h. The solvent volume was reduced to 5 mL in vacuo and Et$_2$O (25 mL) was added. The resulting precipitate was collected in vacuo and washed with Et$_2$O to provide the title compound. $^1$H NMR (CDCl$_3$) δ 2.71 (m, 2H), 3.83 (m, 4H), 3.88 (m, 4H), 4.86 (t, J=6.7 Hz, 2H), 4.99 (dd, J=0.7 and 17.1 Hz, 1H), 5.14 (dd, J=0.7 and 10.3 Hz, 1H), 5.88 (m, 1H), 7.45 (m, 3H), 8.13 (s, 1H), 8.18 (m, 2H), 10.17 (s, 1H). Mass Spectrum (ESI+) m/e=296.1 (M−Br).

Step F. 7-Allyl-2-morpholin-4-yl-4-phenylpyrrolo[1,2-b]pyridazine-5,6-dicarboxylic acid diethyl ester (1). Diethyl acetylenedicarboxylate (200 μL, 1.24 mmol) and a 1M solution of TBAF in THF (912 μL, 0.912 mmol) were added to a solution of 1-but-3-enyl-3-morpholin-4-yl-5-phenylpyridazin-1-ium bromide (312 mg, 0.829 mmol) in THF (30 mL) and EtOH (5 mL). The reaction mixture was heated at reflux for 12 h. The solvent was removed in vacuo and the resulting oil was purified by flash chromatography (silica gel, 10% EtOAc/hexane). The resulting residue was triturated in 1:1 Et$_2$O/hexane and the precipitate was collected by vacuum filtration and washed with hexane to provide the title compound as an off-white solid. $^1$H NMR (DMSO-$d_6$) δ 0.92 (t, J=7.1 Hz, 3H), 1.23 (t, J=7.1 Hz, 3H), 3.56 (m, 6H), 3.74 (m, 4H), 3.95 (d, J=6.4 Hz, 2H), 4.20 (q, J=7.1 Hz, 2H), 5.04 (dd, J=1.7 and 10.0 Hz, 1H), 5.11 (dd, J=1.7 and 17.1 Hz, 1H), 5.97 (m, 1H), 6.82 (s, 1H), 7.43 (m, 2H), 7.49 (m, 3H). Mass Spectrum (ESI+) m/e=464.1 (M+H).

Example 2

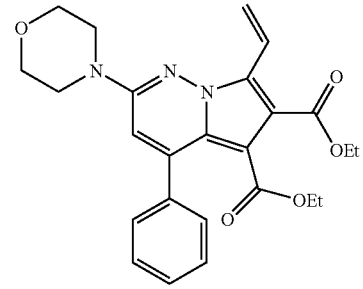

Step A. 1-Allyl-3-morpholin-4-yl-5-phenylpyridazin-1-ium bromide. The title compound was prepared from 4-(5-phenylpyridazin-3-yl)morpholine and allylbromide as described in Example 1, Step E. $^1$H NMR (DMSO-$d_6$) δ 3.76 (s, 8H), 5.21 (d, J=6.2 Hz, 2H), 5.45 (dd, J=1.2 and 10.2 Hz, 1H), 5.54 (dd, J=1.3 and 17.2 Hz, 1H), 6.17 (m, 1H), 7.64 (m, 3H), 8.01 (m, 2H), 8.25 (s, 1H), 9.64 (s, 1H). Mass Spectrum (ESI+) m/e=282.1 (M−Br).

Step B. 2-Morpholin-4-yl-4-phenyl-7-vinylpyrrolo[1,2-b]pyridazine-5,6-dicarboxylic acid diethyl ester (2). The title compound was prepared as described in Example 1, Step F. $^1$H NMR (DMSO-$d_6$) δ 0.89 (t, J=7.2 Hz, 3H), 1.19 (t, J=7.1 Hz, 3H), 3.51 (m, 6H), 3.74 (m, 4H), 4.19 (q, J=7.1 Hz, 2H), 5.61 (dd, J=2.3 and 11.7 Hz, 1H), 6.66 (dd, J=2.5 and 17.6 Hz, 1H), 6.92 (s, 1H), 7.34 (dd, J=12.0 and 17.6 Hz, 1H), 7.40 (m, 2H), 7.48 (m, 3H). Mass Spectrum (ESI+) m/e=450.1 (M+H).

Example 3

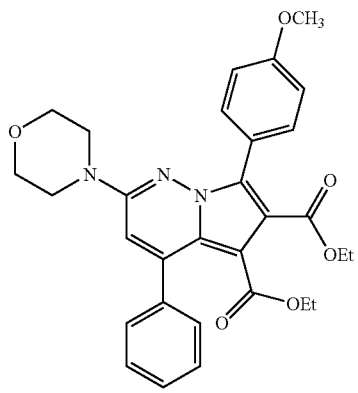

Step A. 1-(4-Methoxybenzyl)-3-morpholin-4-yl-5-phenylpyridazin-1-ium chloride. The title compound was prepared from 4-(5-phenylpyridazin-3-yl)morpholine and 1-chloromethyl-4-methoxybenzene as described in Example 1, Step E. $^1$H NMR (DMSO-d$_6$) δ 3.73 (s, 8H), 3.74 (s, 3H), 5.69 (s, 2H), 6.97 (d, J=8.0 Hz, 2H), 7.60 (d, J=8.2 Hz, 2H), 7.64 (m, 3H), 8.04 (m, 2H), 8.19 (s, 1H), 9.97 (s, 1H). Mass Spectrum (ESI+) m/e=362.3 (M−Cl).

Step B. 7-(4-Methoxyphenyl)-2-morpholin-4-yl-4-phenyl-pyrrolo[1,2-b]pyridazine-5,6-dicarboxylic acid diethyl ester (3). The title compound was prepared as described in Example 1, Step F. $^1$H NMR (DMSO-d$_6$) δ 0.86 (t, J=7.1 Hz, 3H), 1.07 (t, J=7.1 Hz, 3H), 3.39 (m, 4H), 3.52 (q, J=7.2 Hz, 2H), 3.66 (m, 4H), 3.81 (s, 3H), 4.06 (q, J=7.1 Hz, 2H), 6.85 (s, 1H), 7.01 (d, J=8.8 Hz, 2H), 7.49-7.45 (m, 5H), 7.53 (d, J=8.8 Hz, 2H). Mass Spectrum (ESI+) m/e=530.2 (M+H).

Example 4

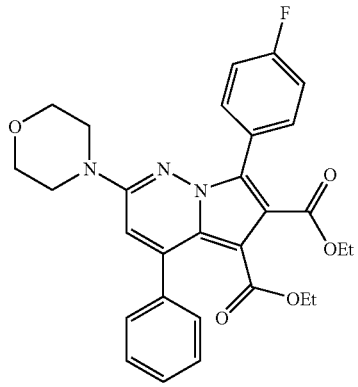

Step A. 1-(4-Fluorobenzyl)-3-morpholin-4-yl-5-phenylpyridazin-1-ium bromide. The title compound was prepared from 4-(5-phenylpyridazin-3-yl)morpholine and 1-bromomethyl-4-fluorobenzene as described in Example 1, Step E. $^1$H NMR (DMSO-d$_6$) δ 3.72 (s, 8H), 5.73, (s, 2H), 7.27 (t, J=8.9 Hz, 2H), 7.65 (m, 3H), 7.71 (m, 2H), 8.00 (m, 2H), 8.20 (d, J=0.89 Hz, 1H), 9.87 (s, 1H). Mass Spectrum (ESI+) m/e=350.1 (M−Br).

Step B. 7-(4-Fluorophenyl)-2-morpholin-4-yl-4-phenyl-pyrrolo[1,2-b]pyridazine-5,6-dicarboxylic acid diethyl ester (4). The title compound was prepared as described in Example 1, Step F. $^1$H NMR (DMSO-d$_6$) δ 0.87 (t, J=7.2 Hz, 3H), 1.06 (t, J=7.1 Hz, 3H), 3.38 (m, 4H), 3.53 (q, J=7.2 Hz, 2H), 3.65 (m, 4H), 4.06 (q, J=7.1 Hz, 2H), 6.88 (s, 1H), 7.30 (m, 2H), 7.49-7.46 (m, 5H), 7.63 (m, 2H). Mass Spectrum (ESI+) m/e=518.1 (M+H).

Example 5

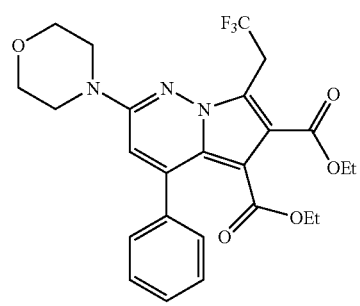

Step A. 3-Morpholin-4-yl-5-phenyl-1-(3,3,3-trifluoropropyl)-pyridazin-1-ium bromide. The title compound was prepared from 4-(5-phenylpyridazin-3-yl)morpholine and 1-bromo-3,3,3-trifluoropropane as described in Example 1, Step E. $^1$H NMR (DMSO-d$_6$) δ 3.24 (m, 2H), 3.75 (m, 4H), 3.80 (m, 4H), 4.88 (t, J=7.0 Hz, 2H), 7.65 (m, 3H), 8.03 (m, 2H), 8.28 (s, 1H), 9.79 (s, 1H). Mass Spectrum (ESI+) m/e=338.1 (M−Br).

Step B. 2-Morpholin-4-yl-4-phenyl-7-(2,2,2-trifluoroethyl)-pyrrolo[1,2-b]pyridazine-5,6-dicarboxylic acid diethyl ester (5). The title compound was prepared as described in Example 1, Step F. $^1$H NMR (DMSO-d$_6$) δ 0.91 (t, J=7.1 Hz, 3H), 1.21 (t, J=7.1 Hz, 3H), 3.53 (m, 6H), 3.71 (m, 4H), 4.20 (q, J=7.1 Hz, 2H), 4.28 (q, J=10.5 Hz, 2H), 6.90 (s, 1H), 7.42 (m, 2H), 7.48 (m, 3H). Mass Spectrum (ESI+) m/e=506.1 (M+H).

Example 6

Step A. 3-Morpholin-4-yl-5-phenyl-1-(4,4,4-trifluorobutyl)-pyridazin-1-ium bromide. The title compound was prepared from 4-(5-phenylpyridazin-3-yl)morpholine and 1-bromo-4,4,4-trifluorobutane as described in Example 1, Step E. $^1$H NMR (DMSO-d$_6$) δ 2.25 (m, 2H), 2.43 (m, 2H), 3.76 (s, 8H), 4.64 (t, J=6.97 Hz, 2H), 7.64 (m, 3H), 8.02 (m, 2H), 8.25 (s, 1H), 9.63 (s, 1H). Mass Spectrum (ESI+) m/e=352.2 (M−Br).

Step B. 2-Morpholin-4-yl-4-phenyl-7-(3,3,3-trifluoropropyl)-pyrrolo[1,2-b]pyridazine-5,6-dicarboxylic acid diethyl ester (6). The title compound was prepared as described in Example 1, Step F. $^1$H NMR (DMSO-$d_6$) δ 0.90 (t, J=7.1 Hz, 3H), 1.21 (t, J=7.1 Hz, 3H), 2.62 (m, 2H), 3.44 (m, 2H), 3.53 (m, 6H), 3.72 (m, 4H), 4.18 (q, J=7.1 Hz, 2H), 6.83 (s, 1H), 7.40 (m, 2H), 7.46 (m, 3H). Mass Spectrum (ESI+) m/e=520.2 (M+H).

Example 7

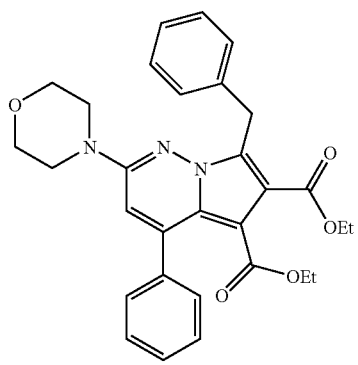

7

Step A. 3-Morpholin-4-yl-1-phenethyl-5-phenylpyridazin-1-ium bromide. The title compound was prepared from 4-(5-phenylpyridazin-3-yl)morpholine and 1-bromoethyl-benzene as described in Example 1, Step E. $^1$H NMR (DMSO-$d_6$) δ 3.30 (m, 2H), 3.70 (s, 8H), 4.83 (t, J=7.1 Hz, 2H), 7.31-7.23 (m, 5H), 7.63 (m, 3H), 8.19 (d, J=0.9 Hz, 1H), 9.52 (d, J=0.8 Hz, 1H). Mass Spectrum (ESI+) m/e=346.2 (M−Br).

Step B. 7-Benzyl-2-morpholin-4-yl-4-phenyl-pyrrolo[1,2-b]pyridazine-5,6-dicarboxylic acid diethyl ester (7). The title compound was prepared as described in Example 1, Step F. The title compound was prepared as described in Example 1, Step F. $^1$H NMR (DMSO-$d_6$) δ 0.89 (t, J=7.1 Hz, 3H), 1.19 (t, J=7.1 Hz, 3H), 3.50 (m, 4H), 3.54 (q, J=7.2 Hz, 2H), 3.66 (m, 4H), 4.20 (q, J=7.1 Hz, 2H), 4.52 (s, 2H), 6.78 (s, 1H), 7.16 (m, 1H), 7.26 (m, 2H), 7.33 (m, 2H), 7.40 (m, 2H), 7.46 (m, 3H). Mass Spectrum (ESI+) m/e=514.2 (M+H).

Example 8

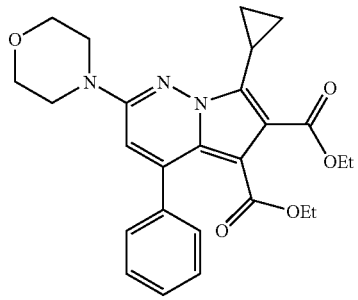

8

Step A. 1-Cyclopropylmethyl-3-morpholin-4-yl-5-phenylpyridazin-1-ium bromide. The title compound was prepared from 4-(5-phenylpyridazin-3-yl)morpholine and 1-bromomethyl-cyclopropane as described in Example 1, Step E. H NMR (DMSO-$d_6$) δ 0.62 (m, 4H), 1.54 (m, 1H), 3.76 (m, 8H), 4.43 (d, J=7.5 Hz, 2H), 7.64 (m, 3H), 8.01 (m, 2H), 8.24 (d, J=0.9 Hz, 1H), 9.61 (d, J=0.8 Hz, 1H). Mass Spectrum (ESI+) m/e=296.3 (M−Br).

Step B. 7-Cyclopropyl-2-morpholin-4-yl-4-phenyl-pyrrolo[1,2-b]pyridazine-5,6-dicarboxylic acid diethyl ester (8). The title compound was prepared as described in Example 1, Step F. $^1$H NMR (DMSO-$d_6$) δ 0.85 (t, J=7.1 Hz, 3H), 0.93 (m, 2H), 1.19 (t, J=7.1 Hz, 3H), 1.37 (m, 2H), 2.52 (m, 1H), 3.47 (m, 6H), 3.71 (m, 4H), 4.16 (q, J=7.1 Hz, 2H), 6.75 (s, 1H), 7.38 (m, 2H), 7.45 (m, 3H). Mass Spectrum (ESI+) m/e=464.2 (M+H).

Example 9

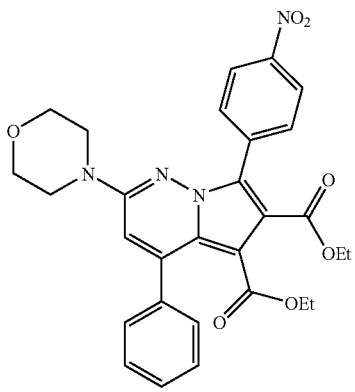

9

Step A. 3-Morpholin-4-yl-1-(4-nitrobenzyl)-5-phenylpyridazin-1-ium bromide. The title compound was prepared from 4-(5-phenylpyridazin-3-yl)morpholine and 1-bromomethyl-4-nitrobenzene as described in Example 1, Step E. $^1$H NMR (DMSO-$d_6$) δ 3.71 (s, 8H), 5.92 (s, 2H), 7.65 (m, 3H), 7.90 (d, J=8.9 Hz, 2H), 8.04 (m, 2H), 8.25 (s, 1H), 8.28 (d, J=8.9 Hz, 2H), 9.96 (s, 1H). Mass Spectrum (ESI+) m/e=377.1 (M−Br).

Step B. 2-Morpholin-4-yl-7-(4-nitrophenyl)-4-phenyl-pyrrolo[1,2-b]pyridazine-5,6-dicarboxylic acid diethyl ester (9). The title compound was prepared as described in Example 1, Step F. $^1$H NMR (DMSO-$d_6$) δ 0.88 (t, J=7.1 Hz, 3H), 1.07 (t, J=7.1 Hz, 3H), 3.40 (m, 4H), 3.55 (q, J=7.2 Hz, 2H), 3.66 (m, 4H), 4.10 (q, J=7.1 Hz, 2H), 6.96 (s, 1H), 7.47 (m, 2H), 7.49 (m, 3H), 7.93 (d, J=8.9 Hz, 2H), 8.32 (d, J=8.9 Hz, 2H). Mass Spectrum (ESI+) m/e=545.1 (M+H).

Example 10

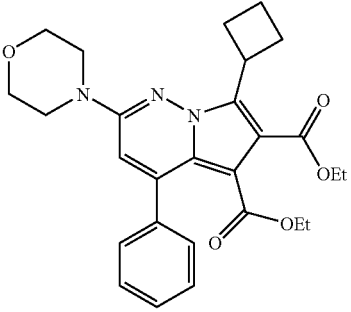

10

Step A. 1-Cyclobutylmethyl-3-morpholin-4-yl-5-phenylpyridazin-1-ium bromide. The title compound was prepared from 4-(5-phenylpyridazin-3-yl)morpholine and 1-bromomethyl-cyclobutane as described in Example 1, Step E. $^1$H NMR (DMSO-$d_6$) δ 1.90 (m, 4H), 2.04 (m, 2H), 2.97 (m, 1H), 3.75 (s, 8H), 4.61 (d, J=7.5 Hz, 2H), 7.64 (m, 3H), 8.01 (m, 2H), 8.23 (s, 1H), 9.63 (s, 1H). Mass Spectrum (ESI+) m/e=310.2 (M−Br).

Step B. 7-Cyclobutyl-2-morpholin-4-yl-4-phenyl-pyrrolo[1,2-b]pyridazine-5,6-dicarboxylic acid diethyl ester (10). The title compound was prepared as described in Example 1, Step F. $^1$H NMR (DMSO-$d_6$) δ 0.84 (t, J=7.1 Hz, 3H), 1.19 (t, J=7.1 Hz, 3H), 2.14-1.84 (m, 2H), 2.18 (m, 2H), 2.86 (m, 2H), 3.49 (q, J=7.1 Hz, 2H), 3.54 (m, 4H), 3.74, (m, 4H), 4.16 (q, J=7.1 Hz, 2H), 4.50 (qn, J=9.2 Hz, 1H), 6.80 (s, 1H), 7.39 (m, 2H), 7.45 (m, 3H). Mass Spectrum (ESI+) m/e=478.2 (M+H).

Example 11

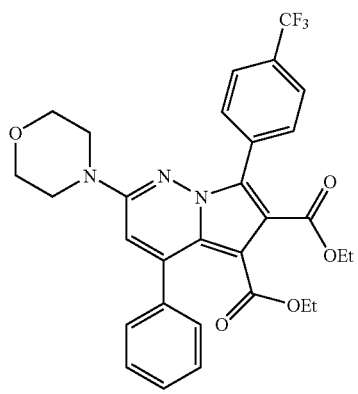

11

Step A. 3-Morpholin-4-yl-5-phenyl-1-(4-trifluoromethyl-benzyl)-pyridazin-1-ium bromide. The title compound was prepared from 4-(5-phenylpyridazin-3-yl)morpholine and 1-bromomethyl-4-trifluoromethylbenzene as described in Example 1, Step E. $^1$H NMR (DMSO-$d_6$) δ 3.71 (s, 8H), 5.86 (s, 2H), 7.65 (m, 3H), 7.81 (d, J=8.4 Hz, 2H), 7.86 (d, J=8.3 Hz, 2H), 8.03 (m, 2H), 8.22 (d, J=0.9 Hz, 1H), 9.93 (d, J=0.9 Hz, 1H). Mass Spectrum (ESI+) m/e=400.2 (M−Br).

Step B. 2-Morpholin-4-yl-4-phenyl-7-(4-triflurometh-ylphenyl)-pyrrolo[1,2-b]pyridazine-5,6-dicarboxylic acid diethyl ester (11). The title compound was prepared as described in Example 1, Step F. $^1$H NMR (DMSO-$d_6$) δ 0.88 (t, J=7.1 Hz, 3H), 1.05 (t, J=7.1 Hz, 3H), 3.39 (m, 4H), 3.54 (q, J=7.2 Hz, 2H), 3.66 (m, 4H), 4.08 (q, J=7.1 Hz, 2H), 6.93 (s, 1H), 7.50-7.45 (m, 5H), 7.84 (m, 4H). Mass Spectrum (ESI+) m/e=568.2 (M+H).

Example 12

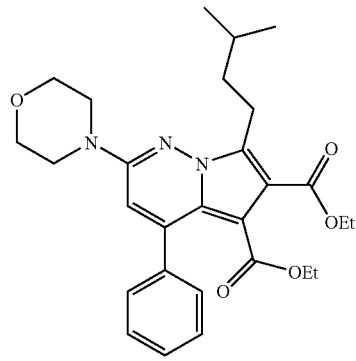

12

Step A. 1-(4-Methylpentyl)-3-morpholin-4-yl-5-phenylpyridazin-1-ium bromide. The title compound was prepared from 4-(5-phenylpyridazin-3-yl)morpholine and 1-bromo-4-methylpentane as described in Example 1, Step E. $^1$H NMR (DMSO-$d_6$) δ 0.87 (d, J=6.6 Hz, 6H), 1.23 (m, 2H), 1.57 (sep, J=6.6 Hz, 1H), 2.01 (m, 2H), 3.76 (s, 8H), 4.55 (t, J=7.3 Hz, 2H), 7.64 (m, 3H), 8.02 (m, 2H), 8.23 (s, 1H), 9.64 (s, 1H). Mass Spectrum (ESI+) m/e=326.3 (M−Br).

Step B. 7-(3-Methylbutyl)-2-morpholin-4-yl-4-phenyl-pyrrolo[1,2-b]pyridazine-5,6-dicarboxylic acid diethyl ester (12). The title compound was prepared as described in Example 1, Step F. $^1$H NMR (DMSO-$d_6$) δ 0.89 (t, J=7.1 Hz, 3H), 0.94 (d, J=6.5 Hz, 6H), 1.21 (t, J=7.1 Hz, 3H), 1.49 (m, 2H), 1.59 (sep, J=6.5 Hz, 1H), 3.16 (m, 2H), 3.52 (m, 6H), 3.72 (m, 4H), 4.16 (q, J=7.1 Hz, 2H), 6.76 (s, 1H), 7.40 (m, 2H), 7.45 (m, 3H). Mass Spectrum (ESI+) m/e=494.2 (M+H).

Example 13

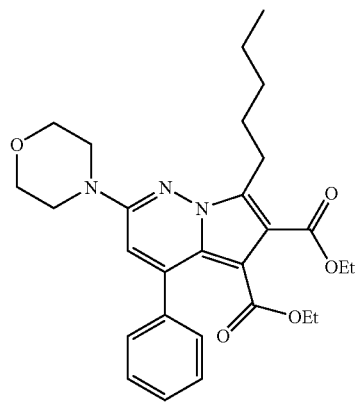

13

Step A. 1-Hexyl-3-morpholin-4-yl-5-phenylpyridazin-1-ium iodide. The title compound was prepared from 4-(5-phenylpyridazin-3-yl)morpholine and 1-iodo-hexane as described in Example 1, Step E. $^1$H NMR (DMSO-$d_6$) δ 0.86 (m, 3H), 1.30 (m, 6H), 1.98 (m, 2H), 3.76 (s, 8H), 4.56 (t, J=7.2 Hz, 2H), 7.64 (m, 3H), 8.01 (m, 2H), 8.22 (s, 1H), 9.63 (s, 1H). Mass Spectrum (ESI+) m/e=328.5 (M−I).

Step B. 2-Morpholin-4-yl-7-pentyl-4-phenyl-pyrrolo[1,2-b]pyridazine-5,6-dicarboxylic acid diethyl ester (13). The title compound was prepared as described in Example 1, Step F. $^1$H NMR (DMSO-d$_6$) δ 0.86 (t, J=6.9 Hz, 3H), 0.89 (t, J=7.2 Hz, 3H), 1.20 (t, J=7.1 Hz, 3H), 1.31 (m, 4H), 1.63 (m, 2H), 3.16 (m, 2H), 3.51 (m, 6H), 3.72 (m, 4H), 4.16 (q, J=7.1 Hz, 2H), 6.76 (s, 1H), 7.40 (m, 2H), 7.45 (m, 3H). Mass Spectrum (ESI+) m/e=494.2 (M+H).

Example 14

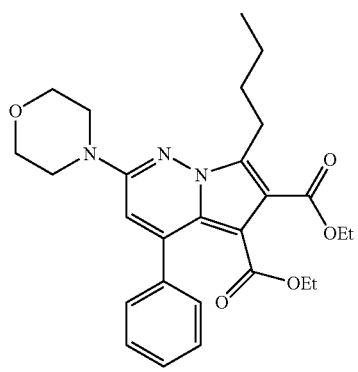

14

Step A. 3-Morpholin-4-yl-1-pentyl-5-phenylpyridazin-1-ium iodide. The title compound was prepared from 4-(5-phenylpyridazin-3-yl)morpholine and 1-iodo-pentane as described in Example 1, Step E. $^1$H NMR (DMSO-d$_6$) δ 0.88 (m, 3H), 1.33 (m, 4H), 1.99 (m, 2H), 3.76 (s, 8H), 4.55 (t, J=7.3 Hz, 2H), 7.63 (m, 3H), 8.01 (m, 2H), 8.23 (s, 1H), 9.63 (s, 1H). Mass Spectrum (ESI+) m/e=314.5 (M−I).

Step B. 7-Butyl-2-morpholin-4-yl-4-phenyl-pyrrolo[1,2-b]pyridazine-5,6-dicarboxylic acid diethyl ester (14). The title compound was prepared as described in Example 1, Step F. $^1$H NMR (DMSO-d$_6$) δ 0.89 (m, 6H), 1.21 (t, J=7.1 Hz, 3H), 1.32 (m, 2H), 1.60 (m, 2H), 3.17 (m, 2H), 3.51 (m, 6H), 3.72 (m, 4H), 4.16 (q, J=7.1 Hz, 2H), 6.76 (s, 1H), 7.40 (m, 2H), 7.45 (m, 3H). Mass Spectrum (ESI+) m/e=480.2 (M+H).

Example 15

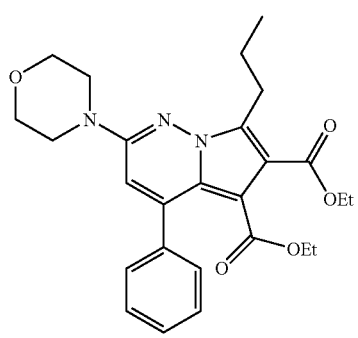

15

Step A. 1-Butyl-3-morpholin-4-yl-5-phenyl-pyridazin-1-ium iodide. The title compound was prepared from 4-(5-phenylpyridazin-3-yl)morpholine and 1-iodo-butane as described in Example 1, Step E. $^1$H NMR (DMSO-d$_6$) δ 1.11 (t, 3H, J=7.4 Hz), 1.52-1.56 (m, 2H), 2.13-2.19 (m, 2H), 3.94 (s, 8H), 4.74 (t, 2H, J=7.4 Hz), 7.80-7.82 (m, 3H), 8.17-8.20 (m, 2H), 8.40 (s, 1H), 9.80 (s, 1H).

Step B. 2-Morpholin-4-yl-4-phenyl-7-propyl-pyrrolo[1,2-b]pyridazine-5,6-dicarboxylic acid diethyl ester (15). The title compound was prepared as described in Example 1, Step F. $^1$H NMR (DMSO-d$_6$) δ 1.05-1.10 (m, 6H), 1.39 (t, 3H, J=7.0 Hz), 1.82-1.88 (m, 2H), 3.33 (t, 2H, J=7.8 Hz), 3.67-3.74 (m, 6H), 3.88-3.91 (m, 4H), 4.35 (q, 2H, J=7.0 Hz), 6.94 (s, 1H), 7.56-7.59 (m, 2H), 7.62-7.65 (m, 3H). Mass Spectrum (ES+) m/e=488.2 (M+23).

Example 16

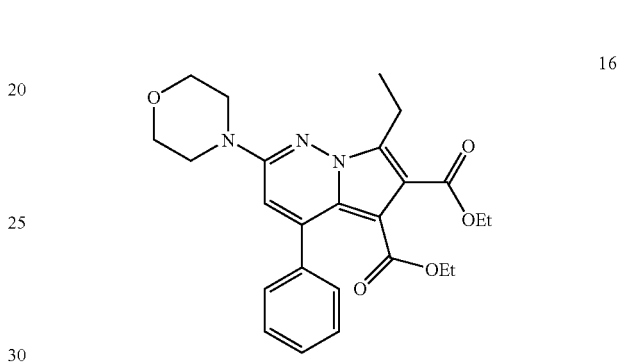

16

Step A. 3-Morpholin-4-yl-5-phenyl-1-propylpyridazin-1-ium iodide. The title compound was prepared from 4-(5-phenylpyridazin-3-yl)morpholine and 1-iodo-propane as described in Example 1, Step E. $^1$H NMR (DMSO-d$_6$) δ 0.94 (t, J=7.4 Hz, 3H), 2.04 (m, 2H), 3.76 (s, 8H), 4.53 (t, J=7.1 Hz, 2H), 7.64 (m, 3H), 8.02 (m, 2H), 8.23 (s, 1H), 9.63 (s, 1H). Mass Spectrum (ESI+) m/e=284.2 (M−I).

Step B. 7-Ethyl-2-morpholin-4-yl-4-phenyl-pyrrolo[1,2-b]pyridazine-5,6-dicarboxylic acid diethyl ester (16). The title compound was prepared as described in Example 1, Step F. $^1$H NMR (DMSO-d$_6$) δ 0.89 (t, J=7.2 Hz, 3H), 1.20 (t, J=7.4 Hz, 3H), 1.21 (t, J=7.1 Hz, 3H), 3.17 (q, J=7.3 Hz, 2H), 3.52 (m, 6H), 3.72 (m, 4H), 4.17 (q, J=7.1 Hz, 2H), 6.77 (s, 1H), 7.40 (m, 2H), 7.45 (m, 3H). Mass Spectrum (ESI+) m/e=452.2 (M+H).

Example 17

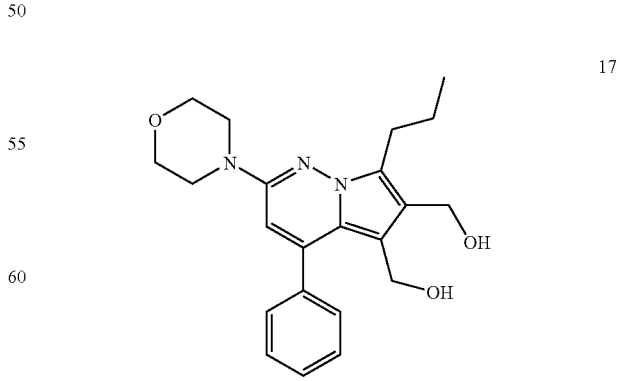

17

(5-Hydroxymethyl-2-morpholin-4-yl-4-phenyl-7-propyl-pyrrolo[1,2-b]pyridazin-6-yl)-methanol (17). To a suspension of lithium aluminum hydride (118 mg, 3.11 mmol) in THF (10 mL) was added 2-morpholino-4-yl-4-phenyl-7-propyl-pyrrolo [1,2-b]pyridazine-5,6-dicarboxylic acid diethyl ester (15) (242 mg, 0.52 mmol). The reaction mixture was heated at reflux for 1 h. After cooling to 0° C., Et$_2$O (10 mL) was added and an excess reagent in the reaction mixture was quenched by brine. The resulting precipitate was removed by filtration. The filtrate was dried over Na$_2$SO$_4$ and concentrated in vacuo to provide the title compound. $^1$H NMR (DMSO-d$_6$) δ 0.92 (t, J=7.2 Hz, 3H), 1.63-1.71 (m, 2H), 2.91 (t, J=7.2 Hz, 2H), 3.40 (br t, J=5.0 Hz, 4H), 3.72 (br t, J=5.0 Hz, 4H), 4.05 (d, J=5.0 Hz, 2H), 4.22 (t, J=5.0 Hz, 1H), 4.55 (d, J=5.1 Hz, 2H), 4.61 (t, J=5.1 Hz, 1H), 6.34 (s, 1H), 7.46-7.48 (m, 3H), 7.53-7.56 (m, 2H). Mass Spectrum (ESI+) m/e=364 (M−OH).

Example 18

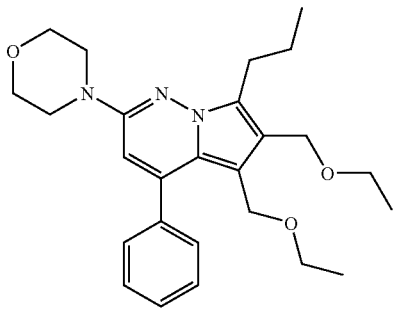

18

5,6-Bis-ethoxymethyl-2-morpholin-4-yl-4-phenyl-7-propyl-pyrrolo[1,2-b]pyridazine (18). To a solution of (5-hydroxymethyl-2-morpholin-4-yl-4-phenyl-7-propyl-pyrrolo[1,2-b]pyridazin-6-yl)-methanol (17) (40 mg, 0.11 mmol) in DMF (0.5 mL) was added 60% NaH (9.2 mg, 0.23 mmol) at 0° C. After stirring at room temperature for 30 min, ethyl iodide (25.2 μL, 0.32 mmol) was added. The reaction mixture was heated at 50° C. for 13 h. After cooling to room temperature, the reaction mixture was poured into saturated aqueous NH$_4$Cl and extracted with Et$_2$O. The organic layer was washed with water and brine and concentrated in vacuo. The resulting oil was purified by thin-layer chromatography using as eluent Hexane-AcOEt (3:1) to provide the title compound. $^1$H NMR (DMSO-d$_6$) δ 0.89-0.94 (m, 6H), 1.09 (t, J=3.5 Hz, 3H), 1.63-1.68 (m, 2H), 2.88-2.97 (m, 4H), 3.38-3.44 (m, 6H), 3.72 (br t, J=4.5 Hz, 4H), 3.90 (s, 2H), 4.46 (s, 2H), 6.38 (s, 1H), 7.47-7.51 (m, 5H). Mass Spectrum (ESI+) m/e=438 (M+H).

Example 19

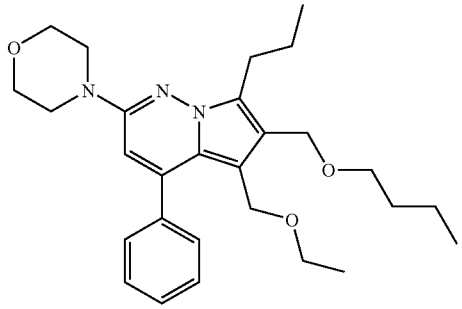

19

Step A. (6-Butoxymethyl-2-morpholin-4-yl-4-phenyl-7-propyl-pyrrolo[1,2-b]pyridazin-5-yl)-methanol. To a solution of (5-hydroxymethyl-2-morpholin-4-yl-4-phenyl-7-propyl-pyrrolo[1,2-b]pyridazin-6-yl)-methanol (17) (40 mg, 0.11 mmol) in DMF (0.5 mL) was added 60% NaH (9.2 mg, 0.23 mmol) at 0° C. After stirring at room temperature for 30 min, n-butyl iodide (29.8 μL, 0.26 mmol) was added. The reaction mixture was heated at 50° C. for 13 h. After cooling to room temperature, the reaction mixture was poured into saturated aqueous NH$_4$Cl and extracted with Et$_2$O. The organic layer was washed with water and brine and concentrated in vacuo. The resulting oil was purified by thin-layer chromatography using as eluent hexane-AcOEt (3:1) to provide the title compound.

Step B. 6-Butoxymethyl-5-ethoxymethyl-2-morpholin-4-yl-4-phenyl-7-propyl-pyrrolo[1,2-b]pyridazine (19). To a solution of (6-butoxymethyl-2-morpholin-4-yl-4-phenyl-7-propyl-pyrrolo[1,2-b]pyridazin-5-yl)-methanol (35 mg, 0.08 mmol) in DMF (0.5 mL) was added 60% NaH (4.0 mg, 0.10 mmol) at 0° C. After stirring at room temperature for 30 min, ethyl iodide (12.8 μL, 0.16 mmol) was added. The reaction mixture was heated at 50° C. for 13 h. After cooling to room temperature, the reaction mixture was poured into saturated aqueous NH$_4$Cl and extracted with Et$_2$O. The organic layer was washed with water and brine and concentrated in vacuo. The resulting oil was purified by thin-layer chromatography using as eluent hexane-AcOEt (3:1) to provide the title compound. $^1$H NMR (DMSO-d$_6$) δ 0.81-0.86 (m, 3H), 0.89-0.94 (m, 4H), 1.08 (t, J=7.0 Hz, 1H), 1.17-1.31 (m, 3H), 1.46 (m, 1H), 1.63-1.70 (m, 2H), 2.89-2.95 (m, 4H), 3.37-3.43 (m, 6H), 3.72 (br t, J=5.0 Hz, 4H), 3.90 (s, 2H), 4.46 (s, 2H), 6.38 (s, 1H), 7.47-7.51 (m, 5H). Mass Spectrum (ESI+) m/e=466 (M+H).

Example 20

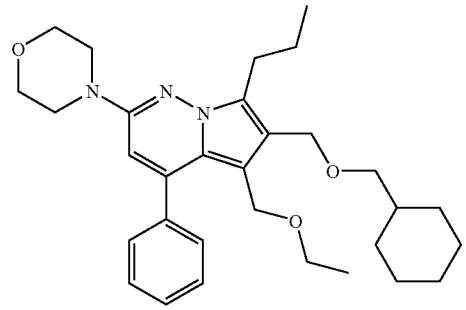

20

Step A. (6-Cyclohexylmethoxymethyl-2-morpholin-4-yl-4-phenyl-7-propyl-pyrrolo[1,2-b]pyridazin-5-yl)-methanol. The title compound was prepared from of (5-hydroxymethyl-2-morpholin-4-yl-4-phenyl-7-propyl-pyrrolo[1,2-b]pyridazin-6-yl)-methanol (17) and bromomethylcyclohexane as described in Example 19, Step A.

Step B. 6-Cyclohexylmethoxymethyl-5-ethoxymethyl-2-morpholin-4-yl-4-phenyl-7-propyl-pyrrolo[1,2-b]pyridazine (20). The title compound was prepared from of (6-cyclohexylmethoxymethyl-2-morpholin-4-yl-4-phenyl-7-propyl-pyrrolo[1,2-b]pyridazin-5-yl)-methanol ethyl iodide as described in Example 19, Step B. $^1$H NMR (DMSO-d6) δ 0.81-0.94 (m, 7H), 1.06-1.67 (m, 12H), 2.75 (d, J=6.3 Hz, 1H), 2.88-2.95 (m, 3H), 3.19 (d, J=6.3 Hz, 1H), 3.39-3.43 (m, 5H), 3.72 (br t, J=5.0 Hz, 4H), 4.02 (s, 2H), 4.45 (br d, J=5.4 Hz, 2H), 6.38 (s, 1H), 7.46-7.49 (m, 5H). Mass Spectrum (ESI+) m/e=506 (M+H).

Example 21

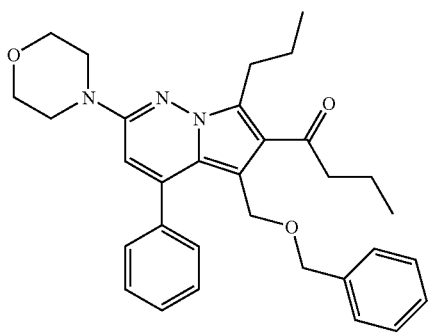

Step A. A mixture of (6-Benzyloxymethyl-2-morpholin-4-yl-4-phenyl-7-propyl-pyrrolo[1,2-b]pyridazin-5-yl)-methanol and (5-benzyloxymethyl-2-morpholin-4-yl-4-phenyl-7-propyl-pyrrolo[1,2-b]pyridazin-6-yl)-methanol. The title compound was prepared from of (5-hydroxymethyl-2-morpholin-4-yl-4-phenyl-7-propyl-pyrrolo[1,2-b]pyridazin-6-yl)-methanol (17) and benzyl bromide as described in Example 19, Step A.

Step B. 5-Benzyloxymethyl-2-morpholin-4-yl-4-phenyl-7-propyl-pyrrolo[1,2-b]pyridazine-6-carbaldehyde. To a solution of a mixture (97 mg, 0.21 mmol) of (6-benzyloxymethyl-2-morpholin-4-yl-4-phenyl-7-propyl-pyrrolo[1,2-b]pyridazin-5-yl)-methanol and (5-benzyloxymethyl-2-morpholin-4-yl-4-phenyl-7-propyl-pyrrolo[1,2-b]pyridazin-6-yl)-methanol in $CH_2Cl_2$ (2 mL) was added molecular sieves (103 mg), NMO (36 mg, 0.31 mmol) and TPAP (7.2 mg, 0.02 mmol) and the reaction mixture was stirred at room temperature overnight. After filtration, the filtrate was concentrated in vacuo. The resulting oil was purified by thin-layer chromatography using as eluent $CHCl_3$-AcOEt (9:1) to provide the title compound. $^1$H NMR ($CDCl_3$) δ 0.92 (t, J=7.5 Hz, 3H), 1.66-1.72 (m, 2H), 3.21 (t, J=7.5 Hz, 2H), 3.51 (br t, J=4.9 Hz, 4H), 3.72 (br t, J=4.9 Hz, 4H), 4.06 (s, 2H), 4.24 (s, 2H), 6.61 (s, 1H), 7.16 (d, J=6.8 Hz, 2H), 7.24-7.31 (m, 3H), 7.46-7.55 (m, 5H), 10.14 (s, 1H).

Step C. 1-(5-Benzyloxymethyl-2-morpholin-4-yl-4-phenyl-7-propyl-pyrrolo[1,2-b]pyridazin-6-yl)-butan-1-ol. To a solution of 5-benzyloxymethyl-2-morpholin-4-yl-4-phenyl-7-propyl-pyrrolo[1,2-b]pyridazine-6-carbaldehyde (19 mg, 0.04 mmol) in THF (0.5 mL) was added n-propyl magnesium chloride (2.0M $Et_2O$ solution, 30 μL, 0.06 mmol) at room temperature under $N_2$. After stirring for 30 min, the reaction mixture was poured into saturated aqueous $NH_4Cl$ and extracted with $Et_2O$. The organic layer was washed with water and brine and concentrated in vacuo to provide the title compound.

Step D. 1-(5-Benzyloxymethyl-2-morpholin-4-yl-4-phenyl-7-propyl-pyrrolo[1,2-b]pyridazin-6-yl)-butan-1-one (21). To a solution of 1-(5-benzyloxymethyl-2-morpholin-4-yl-4-phenyl-7-propyl-pyrrolo[1,2-b]pyridazin-6-yl)-butan-1-ol (22 mg, 0.04 mmol) in $CH_2Cl_2$ (1 mL) was added molecular sieves (50 mg), NMO (7 mg, 0.06 mmol) and TPAP (1.4 mg, 0.004 mmol) and the reaction mixture was stirred at room temperature overnight. After filtration, the filtrate was concentrated in vacuo. The resulting oil was purified by thin-layer chromatography using as eluent $CHCl_3$-AcOEt (9:1) to provide the title compound. $^1$H NMR ($CDCl_3$) δ 0.91 (t, J=7.5 Hz, 3H), 1.00 (t, J=7.3 Hz, 3H), 1.64-1.75 (m, 4H), 2.85 (t, J=7.3 Hz, 2H), 3.14 (t, J=7.5 Hz, 2H), 3.46 (br t, J=4.9 Hz, 4H), 3.83 (br t, J=4.9 Hz, 4H), 4.02 (s, 2H), 4.12 (s, 2H), 6.18 (s, 1H), 7.19-7.28 (m, 5H), 7.42-7.51 (m, 5H). Mass Spectrum (ESI+) m/e=404 (M−BnO).

Example 22

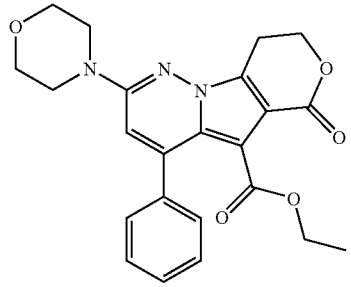

Step A. 1-(3-Hydroxy-propyl)-3-morpholin-4-yl-5-phenyl-pyridazin-1-ium iodide. The title compound was prepared from of 4-(5-phenyl-pyridazin-3-yl)-morpholine and 3-iodo-propan-1-ol as described in Example 1, Step E.

Step B. 7-(2-Hydroxy-ethyl)-2-morpholin-4-yl-4-phenyl-pyrrolo[1,2-b]pyridazine-5,6-dicarboxylic acid diethyl ester. The title compound was prepared from of 1-(3-hydroxy-propyl)-3-morpholin-4-yl-5-phenyl-pyridazin-1-ium iodide and diethyl acetylenedicarboxylate as described in Example 1, Step F. $^1$H NMR ($CDCl_3$) δ 0.97 (t, J=7.2 Hz, 3H), 1.29 (t, J=7.1 Hz, 3H), 2.87 (br s, 1H), 3.50 (br t, J=5.0 Hz, 4H), 3.56 (t, J=6.0 Hz, 2H), 3.63 (q, J=7.2 Hz, 2H), 3.84 (br t, J=5.0 Hz, 4H), 3.99 (br q, J=6.0 Hz, 2H), 4.29 (q, Step C. 6-Morpholin-4-yl-1-oxo-8-phenyl-3,4-dihydro-1H-2-oxa-4b,5-diaza-fluorene-9-carboxylic acid ethyl ester (22). To a solution of 7-(2-hydroxy-ethyl)-2-morpholin-4-yl-4-phenyl-pyrrolo[1,2-b]pyridazine-5,6-dicarboxylic acid diethyl ester (15 mg, 0.03 mmol) in THF (1 mL)-DMF (0.2 mL) was added 60% NaH (4.0 mg, 0.10 mmol). After stirring at room temperature for 30 min, the reaction mixture was poured into saturated aqueous $NH_4Cl$ and extracted with $Et_2O$. The organic layer was washed with water and brine and concentrated in vacuo. The resulting oil was purified by thin-layer chromatography using as eluent $CHCl_3$-AcOEt (1:1) to provide the title compound. $^1$H NMR ($CDCl_3$) δ 0.97 (t, J=7.2 Hz, 3H), 3.23 (t, J=6.2 Hz, 2H), 3.53 (br t, J=5.0 Hz, 4H), 3.75 (q, J=7.2 Hz, 2H), 3.84 (br t, J=5.0 Hz, 4H), 4.63 (t, J=6.2 Hz, 2H), 6.44 (s, 1H), 7.45 (s, 5H). Mass Spectrum (ESI+) m/e=422 (M+H).

Example 23

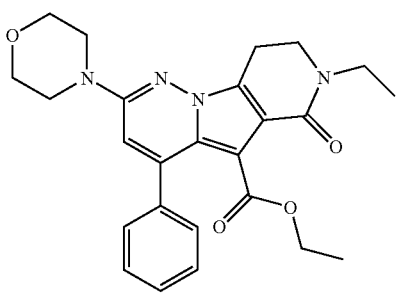

Step A. 7-(2-Methanesulfonyloxy-ethyl)-2-morpholin-4-yl-4-phenyl-pyrrolo[1,2-b]pyridazine-5,6-dicarboxylic acid diethyl ester. To a solution of 7-(2-hydroxy-ethyl)-2-morpholin-4-yl-4-phenyl-pyrrolo[1,2-b]pyridazine-5,6-dicarboxylic acid diethyl ester (10 mg, 0.02 mmol) in THF (1 mL) was added pyridine (6 μL, 0.06 mmol) and methanesulfonic anhydride (7.5 mg, 0.04 mmol). After stirring at room temperature for 13 h, the reaction mixture was poured into saturated aqueous NaHCO$_3$ and extracted with Et$_2$O. The organic layer was washed with water and brine and concentrated in vacuo to provide the title compound.

Step B. 2-Ethyl-6-morpholin-4-yl-1-oxo-8-phenyl-1,2,3,4-tetrahydro-2,4b,5-triaza-fluorene-9-carboxylic acid ethyl ester (23). To a solution of crude 7-(2-methanesulfonyloxy-ethyl)-2-morpholin-4-yl-4-phenyl-pyrrolo[1,2-b]pyridazine-5,6-dicarboxylic acid diethyl ester (17 mg, ca. 0.02 mmol) in THF (2 mL) was added 70% aqueous EtNH$_2$ (300 μL, 3.77 mmol) and heated at 80° C. for 13 h in sealed tube. After cooling to room temperature, the reaction mixture was concentrated in vacuo. The resulting oil was purified by thin-layer chromatography using as eluent CHCl$_3$-AcOEt (1:1) to provide the title compound. $^1$H NMR (CDCl$_3$) δ 0.96 (t, J=7.2 Hz, 3H), 1.19 (t, J=7.5 Hz, 3H), 3.15 (t, J=6.2 Hz, 2H), 3.50 (br t, J=5.0 Hz, 4H), 3.60 (q, J=7.2 Hz, 2H), 3.65-3.74 (m, 4H), 3.83 (br t, J=5.0 Hz, 4H), 6.34 (s, 1H), 7.45 (s, 5H). Mass Spectrum (ESI+) m/e=449 (M+H).

Example 24

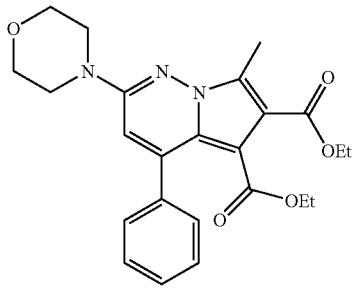

24

Step A. 1-Ethyl-3-morpholin-4-yl-5-phenylpyridazin-1-ium bromide. The title compound was prepared from 4-(5-phenylpyridazin-3-yl)morpholine and 1-bromo-ethane as described in Example 1, Step E. $^1$H NMR (DMSO-d$_6$) δ 1.58 (t, J=7.2 Hz, 3H), 3.75 (m, 8H), 4.60 (q, J=7.3 Hz, 2H), 7.64 (m, 3H), 8.02 (m, 2H), 8.23 (s, 1H), 9.63 (s, 1H). Mass Spectrum (ESI+) m/e=270.2 (M−Br).

Step B. 7-Methyl-2-morpholin-4-yl-4-phenyl-pyrrolo[1,2-b]pyridazine-5,6-dicarboxylic acid diethyl ester (24). The title compound was prepared as described in Example 1, Step F. $^1$H NMR (DMSO-d$_6$) δ 0.89 (t, J=7.1 Hz, 3H), 1.20 (t, J=7.0 Hz, 3H), 2.63 (s, 3H), 3.53 (m, 6H), 3.72 (m, 4H), 4.17 (q, J=7.1 Hz, 2H), 6.77 (s, 1H), 7.40 (m, 2H), 7.46 (m, 3H). Mass Spectrum (ESI+) m/e=438.1 (M+H).

Example 25

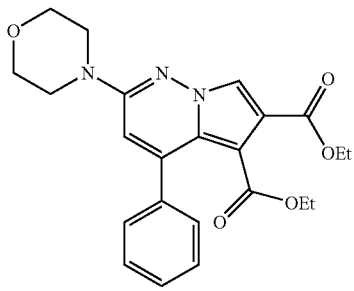

25

Step A. 1-Methyl-3-morpholin-4-yl-5-phenylpyridazin-1-ium iodide. The title compound was prepared from 4-(5-phenylpyridazin-3-yl)morpholine and iodomethane as described in Example 1, Step E. $^1$H NMR (DMSO-d$_6$) δ 3.75 (s, 8H), 4.35 (s, 3H), 7.64 (m, 3H), 8.01 (m, 2H), 8.22 (s, 1H), 9.59 (s, 1H). Mass Spectrum (ESI+) m/e=256.1 (M−I).

Step B. 2-Morpholin-4-yl-4-phenyl-pyrrolo[1,2-b]pyridazine-5,6-dicarboxylic acid diethyl ester (25). The title compound was prepared as described in Example 1, Step F. $^1$H NMR (DMSO-d$_6$) δ 0.90 (t, J=7.1 Hz, 3H), 1.22 (t, J=7.1 Hz, 3H), 3.49 (m, 4H), 3.56 (q, J=7.1 Hz, 2H), 3.70 (m, 4H), 4.17 (q, J=7.1 Hz, 2H), 6.83 (s, 1H), 7.42 (m, 2H), 7.46 (m, 3H), 7.99 (s, 1H). Mass Spectrum (ESI+) m/e=424.1 (M+H).

Example 26

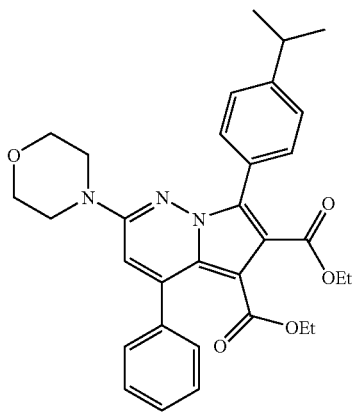

26

Step A. 1-(4-Isopropylbenzyl)-3-morpholin-4-yl-5-phenylpyridazin-1-ium chloride. The title compound was prepared from 4-(5-phenylpyridazin-3-yl)morpholine and 1-bromomethyl-4-isopropylbenzene as described in Example 1, Step E. $^1$H NMR (DMSO-d$_6$) δ 1.17 (d, J=6.9 Hz, 6H), 2.89 (sep, J=6.9 Hz, 1H), 3.73 (s, 8H), 5.71 (s, 2H), 7.29 (d, J=8.2 Hz, 2H), 7.57 (d, J=8.2 Hz, 2H), 7.64 (m, 3H), 8.03 (m, 2H), 8.20 (s, 1H), 9.98 (s, 1H). Mass Spectrum (ESI+) m/e=374.2 (M−Cl).

Step B. 7-(4-Isopropylphenyl)-2-morpholin-4-yl-4-phenyl-pyrrolo[1,2-b]pyridazine-5,6-dicarboxylic acid diethyl ester (26). The title compound was prepared as described in Example 1, Step F. $^1$H NMR (DMSO-d$_6$) δ 0.86 (t, J=7.1 Hz, 3H), 1.06 (t, J=7.1 Hz, 3H), 1.25 (d, J=8.5 Hz, 6H), 2.95 (sep, J=6.9 Hz, 1H), 3.40 (m, 4H), 3.52 (q, J=7.1 Hz, 2H), 3.67 (m, 4H), 4.07 (q, J=7.1 Hz, 2H), 6.87 (s, 1H), 7.33 (d, J=8.3 Hz, 2H), 7.47 (m, 5H), 7.54 (d, J=8.2 Hz, 2H). Mass Spectrum (ESI+) m/e=542.2 (M+H).

Example 27

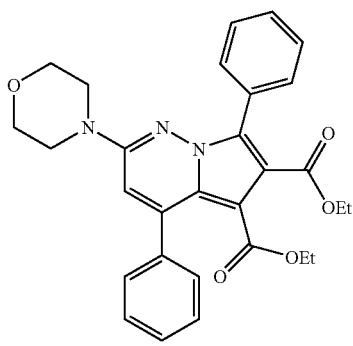

27

Step A. 1-Benzyl-3-morpholin-4-yl-5-phenylpyridazin-1-ium bromide. The title compound was prepared from 4-(5-phenylpyridazin-3-yl)morpholine and benzylbromide as described in Example 1, Step E. ¹H NMR (DMSO-d₆) δ 3.72 (s, 8H), 5.75 (s, 2H), 7.43 (m, 3H), 7.63 (m, 5H), 8.02 (m, 2H), 8.21 (s, 1H), 9.92 (s, 1H). Mass Spectrum (CI+) m/e=332.2 (M−Br).

Step B. 2-Morpholin-4-yl-4,7-diphenyl-pyrrolo[1,2-b]pyridazine-5,6-dicarboxylic acid diethyl ester (27). The title compound was prepared as described in Example 1, Step F. ¹H NMR (DMSO-d₆) δ 0.86 (t, J=7.1 Hz, 3H), 1.05 (t, J=7.1 Hz, 3H), 3.38 (m, 4H), 3.53 (q, J=7.1 Hz, 2H), 3.65 (m, 4H), 4.06 (q, J=7.1 Hz, 2H), 6.88 (s, 1H), 7.49-7.44 (m, 8H), 7.59 (m, 2H). Mass Spectrum (CI+) m/e=500.3 (M+H).

Example 28

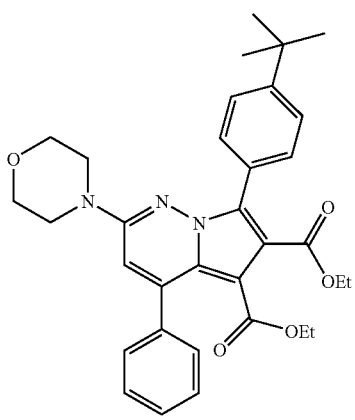

28

Step A. 1-(4-tert-Butylbenzyl)-3-morpholin-4-yl-5-phenylpyridazin-1-ium bromide. The title compound was prepared from 4-(5-phenylpyridazin-3-yl)morpholine and 1-bromomethyl-4-tert-butylbenzene as described in Example 1, Step E. ¹H NMR (DMSO-d₆) δ 1.26 (s, 9H), 3.74 (s, 8H), 5.70 (s, 2H), 7.44 (d, J=8.4 Hz, 2H), 7.57 (d, J=8.3 Hz, 2H), 7.64 (m, 3H), 8.02 (m, 2H), 8.20 (s, 1H), 9.93 (s, 1H). Mass Spectrum (ESI+) m/e=388.2 (M−Br).

Step B. 7-(4-tert-Butylphenyl)-2-morpholin-4-yl-4-phenyl-pyrrolo[1,2-b]pyridazine-5,6-dicarboxylic acid diethyl ester (28). The title compound was prepared as described in Example 1, Step F. ¹H NMR (DMSO-d₆) δ 0.85 (t, J=7.1 Hz, 3H), 1.06 (t, J=7.1 Hz, 3H), 1.33 (s, 9H), 3.41 (m, 4H), 3.52 (q, J=7.2 Hz, 2H), 3.67 (m, 4H), 4.07 (q, J=7.1 Hz, 2H), 6.87 (s, 1H), 7.45-7.48 (m, 7H), 7.56 (m, 2H). Mass Spectrum (ESI+) m/e=556.2 (M+H).

Example 29

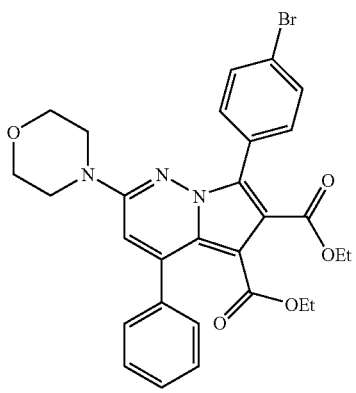

29

Step A. 1-(4-Bromobenzyl)-3-morpholin-4-yl-5-phenylpyridazin-1-ium bromide. The title compound was prepared from 4-(5-phenylpyridazin-3-yl)morpholine and 1-bromomethyl-4-bromobenzene as described in Example 1, Step E. ¹H NMR (DMSO-d₆) δ 3.72 (s, 8H), 5.74 (s, 2H), 7.59-7.66 (m, 7H), 8.03 (m, 2H), 8.21 (s, 1H), 9.91 (s, 1H). Mass Spectrum (ESI+) m/e=410.1 and 412.0 (M−Br).

Step B. 7-(4-Bromophenyl)-2-morpholin-4-yl-4-phenyl-pyrrolo[1,2-b]pyridazine-5,6-dicarboxylic acid diethyl ester (29). The title compound was prepared as described in Example 1, Step F. ¹H NMR (DMSO-d₆) δ 0.87 (t, J=7.1 Hz, 3H), 1.07 (t, J=7.1 Hz, 3H), 3.39 (m, 4H), 3.53 (q, J=7.1 Hz, 2H), 3.66 (m, 4H), 4.07 (q, J=7.1 Hz, 2H), 6.90 (s, 1H), 7.45-7.50 (m, 5H), 7.56 (d, J=8.6 Hz, 2H), 7.66 (d, J=8.6 Hz, 2H). Mass Spectrum (ESI+) m/e=578.0 and 580.0 (M+H).

Example 30

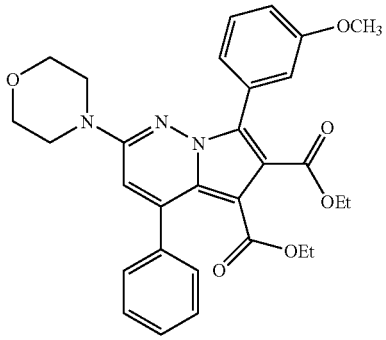

30

Step A. 1-(3-Methoxybenzyl)-3-morpholin-4-yl-5-phenylpyridazin-1-ium bromide. The title compound was prepared from 4-(5-phenylpyridazin-3-yl)morpholine and 1-bromomethyl-3-methoxybenzene as described in Example 1, Step E. ¹H NMR (DMSO-d₆) δ 3.73 (s, 8H), 3.76 (s, 3H), 5.71 (s, 2H), 6.98 (dd, J=2.5 and 8.3 Hz, 1H), 7.19 (d, J=7.6 Hz, 1H), 7.23 (m, 1H), 7.35 (t, J=7.9 Hz, 1H), 7.65 (m, 3H), 8.03 (m, 2H), 8.21 (s, 1H), 9.91 (s, 1H). Mass Spectrum (ESI+) m/e=362.1 (M−Br).

Step B. 7-(3-Methoxyphenyl)-2-morpholin-4-yl-4-phenyl-pyrrolo[1,2-b]pyridazine-5,6-dicarboxylic acid diethyl ester (30). The title compound was prepared as described in Example 1, Step F. ¹H NMR (DMSO-d₆) δ 0.86 (t, J=7.1 Hz, 3H), 1.07 (t, J=7.1 Hz, 3H), 3.40 (m, 4H), 3.53 (q, J=7.1 Hz, 2H), 3.66 (m, 4H), 3.77 (s, 3H), 4.07 (q, J=7.1 Hz, 2H), 6.89 (s, 1H), 6.99 (m, 1H), 7.15 (d, J=7.6 Hz, 1H), 7.19 (m, 1H), 7.37 (t, J=7.9 Hz, 1H), 7.44-7.48 (m, 5H). Mass Spectrum (ESI+) m/e=530.2 (M+H).

Example 31

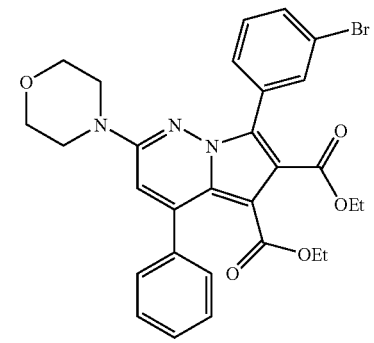

31

Step A. 1-(3-Bromobenzyl)-3-morpholin-4-yl-5-phenylpyridazin-1-ium bromide. The title compound was prepared from 4-(5-phenylpyridazin-3-yl)morpholine and 1-bromomethyl-3-bromobenzene as described in Example 1, Step E. $^1$H NMR (DMSO-$d_6$) δ 3.72 (s, 8H), 5.75 (s, 2H), 7.40 (t, J=7.9 Hz, 1H), 7.64 (m, 5H), 7.90 (s, 1H), 8.03 (m, 2H), 8.22 (s, 1H), 9.88 (s, 1H). Mass Spectrum (ESI+) m/e=410.2 and 412.3 (M−Br).

Step B. 7-(3-Bromophenyl)-2-morpholin-4-yl-4-phenyl-pyrrolo[1,2-b]pyridazine-5,6-dicarboxylic acid diethyl ester (31). The title compound was prepared as described in Example 1, Step F. $^1$H NMR (DMSO-$d_6$) δ 0.87 (t, J=7.1 Hz, 3H), 1.08 (t, J=7.1 Hz, 3H), 3.40 (m, 4H), 3.54 (q, J=7.1 Hz, 2H), 3.66 (m, 4H), 4.08 (q, J=7.1 Hz, 2H), 6.91 (s, 1H), 7.43-7.50 (m, 6H), 7.62 (m, 2H), 7.82 (m, 1H). Mass Spectrum (ESI+) m/e=578.0 and 580.0 (M+H).

Example 32

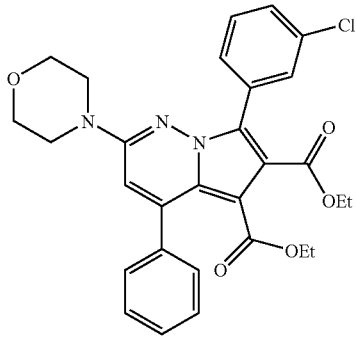

Step A. 1-(3-Chlorobenzyl)-3-morpholin-4-yl-5-phenylpyridazin-1-ium bromide. The title compound was prepared from 4-(5-phenylpyridazin-3-yl)morpholine and 1-bromomethyl-3-chlorobenzene as described in Example 1, Step E. $^1$H NMR (DMSO-$d_6$) δ 3.72 (s, 8H), 5.76 (s, 2H), 7.46-7.49 (m, 2H), 7.61 (m, 1H), 7.65 (m, 3H), 7.76 (m, 1H), 8.04 (m, 2H), 8.22 (s, 1H), 9.90 (s, 1H). Mass Spectrum (ESI+) m/e=366.2 (M−Br).

Step B. 7-(3-Chlorophenyl)-2-morpholin-4-yl-4-phenyl-pyrrolo[1,2-b]pyridazine-5,6-dicarboxylic acid diethyl ester (32). The title compound was prepared as described in Example 1, Step F. $^1$H NMR (DMSO-$d_6$) δ 0.87 (t, J=7.1 Hz, 3H), 1.07 (t, J=7.1 Hz, 3H), 3.40 (m, 4H), 3.54 (q, J=7.1 Hz, 2H), 3.66 (m 4H), 4.08 (q, J=7.1 Hz, 2H), 6.91 (s, 1H), 7.44-7.49 (m, 7H), 7.57 (m, 1H), 7.67 (m, 1H). Mass Spectrum (ESI+) m/e=534.1 (M+H).

Example 33

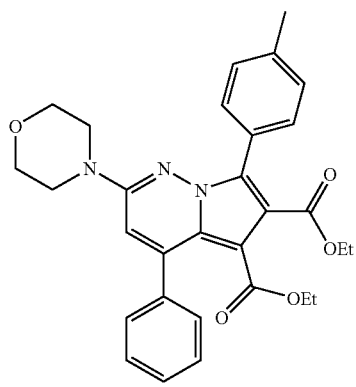

Step A. 1-(4-Methylbenzyl)-3-morpholin-4-yl-5-phenylpyridazin-1-ium chloride. The title compound was prepared from 4-(5-phenylpyridazin-3-yl)morpholine and 1-chloromethyl-4-methylbenzene as described in Example 1, Step E. $^1$H NMR (DMSO-$d_6$) δ 2.29 (s, 3H), 3.72 (s, 8H), 5.72 (s, 2H), 7.22 (d, J=7.9 Hz, 2H), 7.53 (d, J=8.0 Hz, 2H), 7.64 (m, 3H), 8.05 (m, 2H), 8.21 (s, 1H), 10.01 (s, 1H). Mass Spectrum (ESI+) m/e=346.2 (M−Cl).

Step B. 7-(4-Methylphenyl)-2-morpholin-4-yl-4-phenyl-pyrrolo[1,2-b]pyridazine-5,6-dicarboxylic acid diethyl ester (33). The title compound was prepared as described in Example 1, Step F. $^1$H NMR (DMSO-$d_6$) δ 0.86 (t, J=7.1 Hz, 3H), 1.07 (t, J=7.1 Hz, 3H), 2.37 (s, 3H), 3.38 (m, 4H), 3.53 (q, J=7.2 Hz, 2H), 3.66 (m, 4H), 4.06 (q, J=7.0 Hz, 2H), 6.87 (s, 1H), 7.26 (d, J=8.1 Hz, 2H), 7.45-7.50 (m, 7H). Mass Spectrum (ESI+) m/e=514.2 (M+H).

Example 34

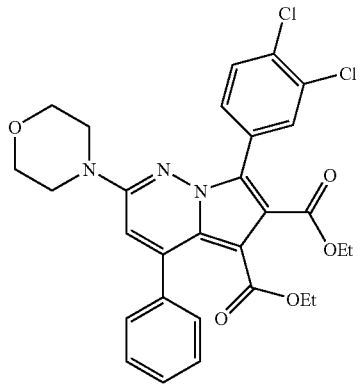

Step A. 1-(3,4-Dichlorobenzyl)-3-morpholin-4-yl-5-phenylpyridazin-1-ium bromide. The title compound was prepared from 4-(5-phenylpyridazin-3-yl)morpholine and 1-bromomethyl-3,4-dichlorobenzene as described in Example 1, Step E. $^1$H NMR (DMSO-$d_6$) δ 3.72 (s, 8H), 5.76 (s, 2H), 7.65 (m, 4H), 7.72 (d, J=8.3 Hz, 1H), 7.98 (d, J=2.0 Hz, 1H), 8.03 (m, 2H), 8.22 (s, 1H), 9.88 (s, 1H). Mass Spectrum (ESI+) m/e=400.0 and 402.0 (M−Br).

Step B. 7-(3,4-Dichloro-phenyl)-2-morpholin-4-yl-4-phenyl-pyrrolo[1,2-b]pyridazine-5,6-dicarboxylic acid diethyl ester (34). The title compound was prepared as described in Example 1, Step F. $^1$H NMR (DMSO-$d_6$) δ 0.88 (t, J=7.1 Hz, 3H), 1.08 (t, J=7.1 Hz, 3H), 3.40 (m, 4H), 3.54 (q, J=7.0 Hz, 2H), 3.66 (m, 4H), 4.09 (q, J=7.1 Hz, 2H), 6.93 (s, 1H), 7.45 (m, 2H), 7.49 (m, 3H), 7.63 (dd, J=1.8 and 8.4 Hz, 1H), 7.74 (d, J=8.4 Hz, 1H), 7.90 (d, J=1.8 Hz, 1H). Mass Spectrum (ESI+) m/e=568.0 (M+H).

Example 35

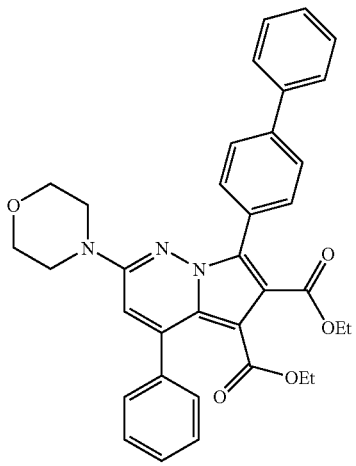

35

Step A. 4-(Biphenyl-4-ylmethyl)-3-morpholin-4-yl-5-phenyl-1-pyridazin-1-ium bromide. The title compound was prepared from 4-(5-phenylpyridazin-3-yl)morpholine and 1-bromomethyl-4-phenylbenzene as described in Example 1, Step E. $^1$H NMR (DMSO-$d_6$) δ 3.74 (s, 8H), 5.80 (s, 2H), 7.38 (m, 1H), 7.47 (m, 2H), 7.66 (m, 5H), 7.73 (s, 4H), 8.04 (m, 2H), 8.22 (s, 1H), 9.96 (s, 1H). Mass Spectrum (ESI+) m/e=408.1 (M−Br).

Step B. 7-(Biphenyl)-2-morpholin-4-yl-4-phenyl-pyrrolo[1,2-b]pyridazine-5,6-dicarboxylic acid diethyl ester (35). The title compound was prepared as described in Example 1, Step F. $^1$H NMR (DMSO-$d_6$) δ 0.87 (t, J=7.1 Hz, 3H), 1.09 (t, J=7.1 Hz, 3H), 3.41 (m, 4H), 3.54 (q, J=7.1 Hz, 2H), 3.66 (m, 4H), 4.10 (q, J=7.1 Hz, 2H), 6.90 (s, 1H), 7.40 (m, 1H), 7.47-7.51 (m, 7H), 7.71-7.79 (m, 6H). Mass Spectrum (ESI+) m/e=576.1 (M+H).

Example 36

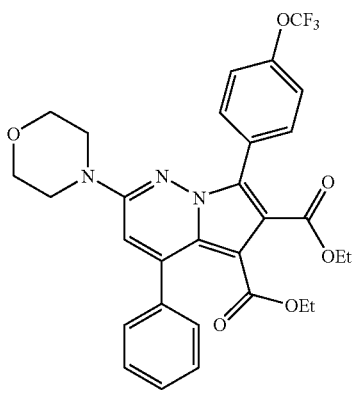

36

Step A. 3-Morpholin-4-yl-5-phenyl-1-(4-trifluoromethoxybenzyl)-pyridazin-1-ium bromide. The title compound was prepared from 4-(5-phenylpyridazin-3-yl)morpholine and 1-bromomethyl-4-trifluoromethoxybenzene as described in Example 1, Step E. $^1$H NMR (DMSO-$d_6$) δ 3.72 (s, 8H), 5.79 (s, 2H), 7.44 (d, J=8.5 Hz, 2H), 7.65 (m, 3H), 7.79 (d, J=8.6 Hz, 2H), 8.03 (m, 2H), 8.22 (s, 1H), 9.92 (s, 1H). Mass Spectrum (ESI+) m/e=416.1 (M−Br).

Step B. 2-Morpholin-4-yl-4-phenyl-7-(4-trifluoromethoxyphenyl)-pyrrolo[1,2-b]pyridazine-5,6-dicarboxylic acid diethyl ester (36). The title compound was prepared as described in Example 1, Step F. $^1$H NMR (DMSO-$d_6$) δ 0.88 (t, J=7.1 Hz, 3H), 1.04 (t, J=7.1 Hz, 3H), 3.38 (m, 4H), 3.54 (q, J=7.1 Hz, 2H), 3.66 (m, 4H), 4.06 (q, J=7.1 Hz, 2H), 6.90 (s, 1H), 7.45-7.50 (m, 7H), 7.74 (d, J=8.6 Hz, 2H). Mass Spectrum (ESI+) m/e=584.1 (M+H).

Example 37

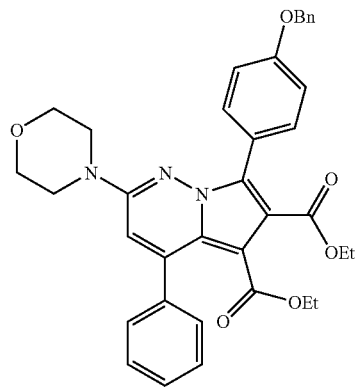

37

Step A. 1-(4-Benzyloxybenzyl)-3-morpholin-4-yl-5-phenylpyridazin-1-ium chloride. The title compound was prepared from 4-(5-phenylpyridazin-3-yl)morpholine and 1-bromomethyl-4-benzyloxybenzene as described in Example 1, Step E. $^1$H NMR (DMSO-$d_6$) δ 3.72 (s, 8H), 5.10 (s, 2H), 5.68 (s, 2H), 7.04 (d, J=8.7 Hz, 2H), 7.31-7.44 (m, 5H), 7.59 (d, J=8.7 Hz, 2H), 7.64 (m, 3H), 8.04 (m, 2H), 8.19 (s, 1H), 9.96 (s, 1H). Mass Spectrum (ESI+) m/e=438.4 (M−Cl).

Step B. 7-(4-Benzyloxyphenyl)-2-morpholin-4-yl-4-phenyl-pyrrolo[1,2-b]pyridazine-5,6-dicarboxylic acid diethyl ester (37). The title compound was prepared as described in Example 1, Step F. $^1$H NMR (DMSO-$d_6$) δ 0.86 (t, J=7.2 Hz, 3H), 1.05 (t, J=7.1 Hz, 3H), 3.39 (m, 4H), 3.52 (q, J=7.2 Hz, 2H), 3.66 (m, 4H), 4.06 (q, J=7.1 Hz, 2H), 5.16 (s, 2H), 6.85 (s, 1H), 7.09 (d, J=8.9 Hz, 2H), 7.33-7.50 (m, 10H), 7.53 (d, J=8.9 Hz, 2H). Mass Spectrum (ESI+) m/e=606.2 (M+H).

Example 38

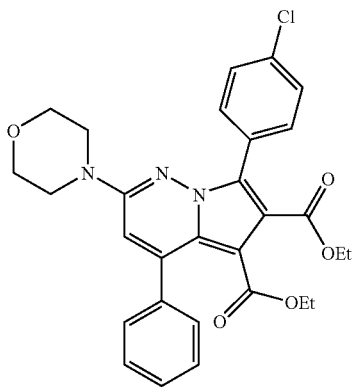

Step A. 1-(4-Chlorobenzyl)-3-Morpholin-4-yl-5-phenylpyridazin-1-ium bromide. The title compound was prepared from 4-(5-phenylpyridazin-3-yl)morpholine and 1-bromomethyl-4-chlorobenzene as described in Example 1, Step E. $^1$H NMR (DMSO-d$_6$) δ 3.74 (s, 8H), 5.77 (s, 2H), 7.53 (d, J=8.6 Hz, 2H), 7.68 (m, 5H), 8.04 (m, 2H), 8.23 (d, J=0.84 Hz, 1H), 9.91 (s, 1H). Mass Spectrum (ESI+) m/e=366.1 (M−Br).

Step B. 7-(4-Chlorophenyl)-2-morpholin-4-yl-4-phenyl-pyrrolo[1,2-b]pyridazine-5,6-dicarboxylic acid diethyl ester (38). The title compound was prepared as described in Example 1, Step F. $^1$H NMR (DMSO-d$_6$) δ 0.87 (t, J=7.1 Hz, 3H), 1.07 (t, J=7.1 Hz, 3H), 3.38 (m, 4H), 3.54 (q, J=7.2 Hz, 2H), 3.66 (m, 4H), 4.07 (q, J=7.1 Hz, 2H), 6.90 (s, 1H), 7.45-7.50 (m, 5H), 7.52 (d, J=8.5 Hz, 2H), 7.63 (d, J=8.6 Hz, 2H). Mass Spectrum (ESI+) m/e=534.1 (M+H).

Example 39

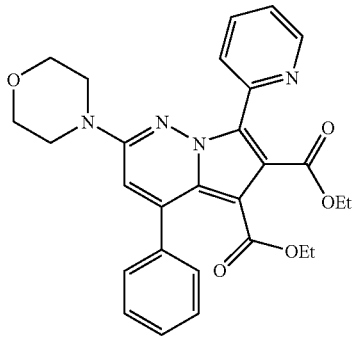

Step A. 2-(3-Morpholin-4-yl-5-phenylpyridazin-1-ium bromide)pyridine hydrobromide. A solution of 4-(5-phenylpyridazin-3-yl)morpholine (200 mg, 0.829 mmol) and 2-(bromomethyl)pyridine hydrobromide (210 mg, 0.829 mmol) in CH$_3$CN (25 mL) was heated at reflux for 24 h. The solvent volume was reduced to 5 mL in vacuo and Et$_2$O (25 mL) was added. The resulting precipitate was collected in vacuo and washed with Et$_2$O to provide the title compound. $^1$H NMR (DMSO-d$_6$) 3.68 (s, 8H), 5.95 (s, 2H), 7.44 (ddd, J=0.96, 4.9, and 7.5 Hz, 1H), 7.64-7.69 (m, 4H), 7.93 (dt, J=1.8 and 7.7 Hz, 1H), 8.06 (m, 2H), 8.27 (s, 1H), 8.56 (m, 1H), 9.91 (s, 1H). Mass Spectrum (ESI+) m/e=333.4 (M−HBr$_2$).

Step B. 2-Morpholin-4-yl-4-phenyl-7-pyridin-2-yl-pyrrolo[1,2-b]pyridazine-5,6-dicarboxylic acid diethyl ester (39). Diethyl acetylenedicarboxylate (252 μL, 1.57 mmol) and a 1M solution of TBAF in THF (1.57 mL, 1.57 mmol) were added to a solution of 2-(3-morpholin-4-yl-5-phenylpyridazin-1-ium bromide)pyridine hydrobromide (389 mg, 0.787 mmol) in THF (30 mL) and EtOH (5 mL). The reaction mixture was heated at reflux for 18 h. The solvent was removed in vacuo and replaced with EtOAc. The solution was washed with saturated aqueous NaHCO$_3$, dried (MgSO$_4$), filtered, and concentrated in vacuo to provide a brown oil. Purification by flash chromatography (silica gel, 35% EtOAc/hexane) followed by trituration in 1:1 Et$_2$O/hexane provided the title compound as an off-white solid. $^1$H NMR (DMSO-d$_6$) δ 0.82 (t, J=7.1 Hz, 3H), 1.08 (t, J=7.1 Hz, 3H), 3.47 (m, 4H), 3.54 (q, J=7.1 Hz, 2H), 3.70 (m, 4H), 4.10 (q, J=7.1 Hz, 2H), 6.96 (s, 1H), 7.36 (ddd, J=0.9, 4.9, and 7.5 Hz, 1H), 7.48 (s, 5H), 7.93 (dt, J=1.8 and 7.8 Hz, 1H), 8.16 (d, J=8.0 Hz, 1H), 8.60 (d, J=4.2 Hz, 1H). Mass Spectrum (ESI+) m/e=501.1 (M+H).

Example 40

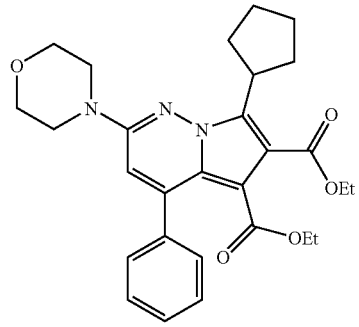

7-Cyclopentyl-2-morpholin-4-yl-4-phenyl-pyrrolo[1,2-b]pyridazine-5,6-dicarboxylic acid diethyl ester (40). A solution of 4-(5-phenylpyridazin-3-yl)morpholine (150 mg, 0.622 mmol) and methanesulfonic acid cyclopentylmethyl ester (Newcomb et al. (1980) *J. Org. Chem.* 45:1707-1708) (890 mg, 4.99 mmol) in CH$_3$CN (30 mL) was heated at reflux for 48 h. The solvent was removed in vacuo to provide a brown oil. Diethyl acetylenedicarboxylate (150 μL, 0.933 mmol) and a 1M solution of TBAF in THF (684 μL, 0.684 mmol) were added to a solution of this oil in THF (30 mL) and EtOH (5 mL). The reaction mixture was heated at reflux for 20 h. The solvent was removed in vacuo and the residue was purified by flash chromatography (silica gel, 15% EtOAc/hexane). The resulting residue was triturated in 1:1 Et$_2$O/hexane to provide the title compound as an off-white solid. $^1$H NMR (DMSO-d$_6$) δ 0.86 (t, J=7.1 Hz, 3H), 1.17 (t, J=7.1 Hz, 3H), 1.66 (m, 2H), 1.76 (m, 2H), 1.87 (m, 2H), 2.23 (m, 2H), 3.48 (m, 6H), 3.72 (m, 4H), 4.06 (m, 1H), 4.15 (q, J=7.1 Hz, 2H), 6.77 (s, 1H), 7.39 (m, 2H), 7.45 (m, 3H). Mass Spectrum (ESI+) m/e=492.3 (M+H).

Example 41

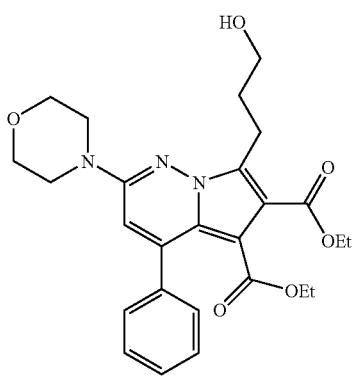

7-(3-Hydroxypropyl)-2-morpholin-4-yl-4-phenyl-pyrrolo[1,2-b]pyridazine-5,6-dicarboxylic acid diethyl ester (41). BH$_3$.THF (162 µL, 0.162 mmol) was added dropwise via syringe to a solution of 1 (50 mg, 0.108 mmol) in anhydrous THF (6 mL). The reaction mixture was stirred at ambient temperature for 1 h. 5% aqueous NaOH (0.5 mL) and 30% aqueous H$_2$O$_2$ (1 mL) were added and the reaction mixture was stirred at ambient temperature for 1.5 h. The reaction mixture was extracted with EtOAc and the organic layers were pooled, washed with brine, dried (MgSO$_4$), filtered, and concentrated in vacuo to provide a yellow oil. The oil was purified by flash chromatography (silica gel, 40% EtOAc/hexane) to yield a yellow oil. The oil was triturated in (1:1) Et$_2$O/hexane to provide a white solid. $^1$H NMR (DMSO-d$_6$) δ 0.89 (t, J=7.2 Hz, 3H), 1.21 (t, J=7.0 Hz, 3H), 1.78 (m, 2H), 3.18 (m, 2H), 3.40 (m, 2H), 3.50 (m, 6H), 3.72 (m, 4H), 4.16 (q, J=7.1 Hz, 2H), 4.45 (t, J=5.3 Hz, 1H), 6.77 (s, 1H), 7.41 (m, 2H), 7.46 (m, 3H). Mass Spectrum (ESI+) m/e=482.2 (M+H).

Example 42

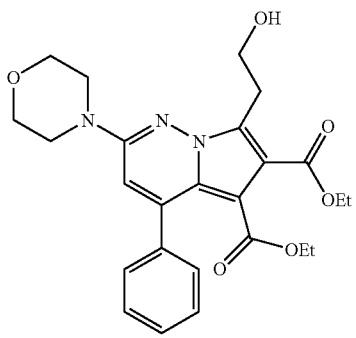

7-(2-Hydroxyethyl)-2-morpholin-4-yl-4-phenyl-pyrrolo[1,2-b]pyridazine-5,6-dicarboxylic acid diethyl ester (42). The title compound was prepared from 2 as described in Example 34. $^1$H NMR (DMSO-d$_6$) δ 0.89 (t, J=7.2 Hz, 3H), 1.20 (t, J=7.1 Hz, 3H), 3.29 (m, 2H), 3.51 (m, 6H), 3.64 (m, 2H), 3.72 (m, 4H), 4.16 (q, J=7.1 Hz, 2H), 4.73 (t, J=5.6 Hz, 1H), 6.77 (s, 1H), 7.40 (m, 2H), 7.46 (m, 3H). Mass Spectrum (ESI+) m/e=468.1 (M+H).

Example 43

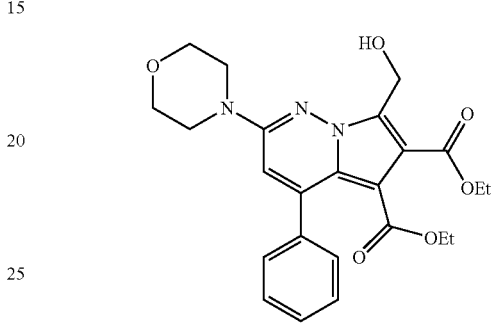

Step A. 1-[2-(tert-Butyldimethylsilanyloxy)ethyl]-3-morpholin-4-yl-5-phenylpyridazin-1-ium bromide. The title compound was prepared from 4-(5-phenylpyridazin-3-yl)morpholine and 2-bromoethoxy-tert-butyldimethylsilane as described in Example 1, Step E. $^1$H NMR (DMSO-d$_6$) δ −0.83 (s, 6H), 0.70 (s, 9H), 3.74 (m, 4H), 3.79 (m, 4H), 4.14 (t, J=4.9 Hz, 2H), 4.69 (t, J=4.9 Hz, 2H), 7.65 (m, 3H), 8.01 (m, 2H), 8.28 (s, 1H), 9.65 (s, 1H). Mass Spectrum (ESI+) m/e=400.2 (M−Br).

Step B. 7-Hydroxymethyl-2-morpholin-4-yl-4-phenyl-pyrrolo[1,2-b]pyridazine-5,6-dicarboxylic acid diethyl ester (43). Diethyl acetylenedicarboxylate (168 µL, 1.05 mmol) and a 1M solution of TBAF in THF (1.4 mL, 1.40 mmol) were added to a solution of 1-[2-(tert-butyldimethylsilanyloxy)ethyl]-3-morpholin-4-yl-5-phenylpyridazin-1-ium bromide in THF (24 mL) and EtOH (6 mL). The reaction mixture was heated at reflux for 6 h. The solvent was removed in vacuo and replaced with THF (20 mL). A 1M solution of TBAF in THF (1.4 mL, 1.40 mmol) was added and the reaction mixture was stirred at ambient temperature for 2 h. The reaction mixture was diluted with water (20 mL) and extracted with EtOAc. The organic layers were pooled, washed with brine, dried (MgSO$_4$), filtered, and concentrated in vacuo to provide a brown oil. Purification by flash chromatography (silica gel, 1:1 EtOAc/hexane) yielded a yellow oil. The oil was sonicated in (1:1) Et$_2$O/hexane and the resulting precipitate was collected by vacuum filtration to provide the title compound as an off-white solid. $^1$H NMR (DMSO-d$_6$) δ 0.89 (t, J=7.2 Hz, 3H), 1.21 (t, J=7.1 Hz, 3H), 3.53 (m, 6H), 3.70 (m, 4H), 4.18 (q, J=7.3 Hz, 2H), 4.87 (t, J=5.8 Hz, 1H), 4.95 (d, J=5.8 Hz, 2H), 6.84 (s, 1H), 7.40 (m, 2H), 7.46 (m, 3H). Mass Spectrum (ESI+) m/e=454.2 (M+H).

Example 44

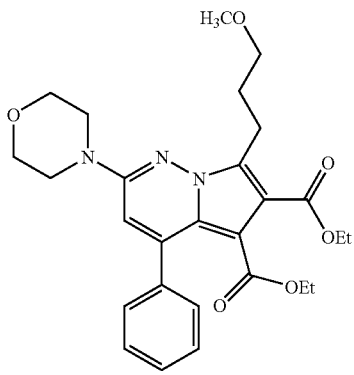

7-(3-Methoxypropyl)-2-morpholin-4-yl-4-phenyl-pyrrolo[1,2-b]pyridazine-5,6-dicarboxylic acid diethyl ester (44). A solution of 41 (10.4 mg, 0.022 mmol), MeI (24 µL, 0.389 mmol), and Ag$_2$O (25 mg, 0.108 mmol) in CH$_3$CN (1 mL) was heated at 80° C. for 24 h. The reaction mixture was filtered through celite and washed with CH$_2$Cl$_2$. The filtrate was concentrated in vacuo and purified by TLC (silica gel, 35% EtOAc/hexane) to provide a yellow oil. The oil was sonicated in 2:1 Et$_2$O/hexane to provide the title compound as an off-white solid. $^1$H NMR (DMSO-d$_6$) δ 0.88 (t, J=7.1 Hz, 3H), 1.21 (t, J=7.1 Hz, 3H), 1.87 (m, 2H), 3.20 (m, 2H), 3.21 (s, 3H), 3.52 (m, 8H), 3.72 (m, 4H), 4.17 (q, J=7.1 Hz, 2H), 6.77 (s, 1H), 7.40 (m, 2H), 7.46 (m, 3H). Mass Spectrum (ESI+) m/e=496.2 (M+H).

Example 45

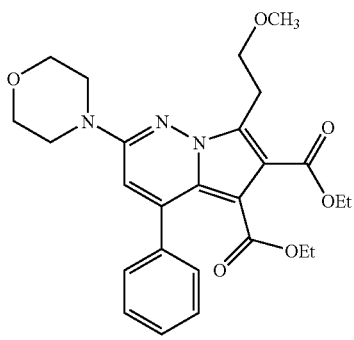

7-(2-Methoxyethyl)-2-morpholin-4-yl-4-phenyl-pyrrolo[1,2-b]pyridazine-5,6-dicarboxylic acid diethyl ester (45). The title compound was prepared from 42 as described in Example 37. $^1$H NMR (DMSO-d$_6$) δ 0.89 (t, J=7.1 Hz, 3H), 1.20 (t, J=7.1 Hz, 3H), 3.26 (s, 3H), 3.45 (t, J=7.0 Hz, 2H), 3.52 (m, 6H), 3.61 (t, J=7.0 Hz, 2H), 3.72 (m, 4H), 4.16 (q, J=7.1 Hz, 2H), 6.79 (s, 1H), 7.40 (m, 2H), 7.47 (m, 3H). Mass Spectrum (ESI+) m/e=482.3 (M+H).

Example 46

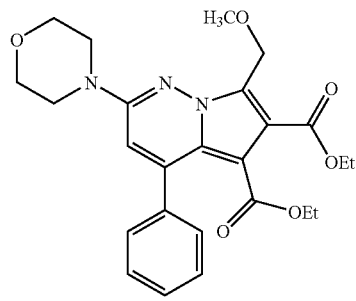

7-Methoxymethyl-2-morpholin-4-yl-4-phenyl-pyrrolo[1,2-b]pyridazine-5,6-dicarboxylic acid diethyl ester (46). The title compound was prepared from 43 as described in Example 37. $^1$H NMR (DMSO-d$_6$) δ 0.89 (t, J=7.1 Hz, 3H), 1.21 (t, J=7.1 Hz, 3H), 3.28 (s, 3H), 3.53 (m, 6H), 3.72 (m, 4H), 4.19 (q, J=7.1 Hz, 2H), 4.91 (s, 2H), 6.87 (s, 1H), 7.41 (m, 2H), 7.47 (m, 3H). Mass Spectrum (ESI+) m/e=436.2 ([M+H]—OCH$_3$).

Example 47

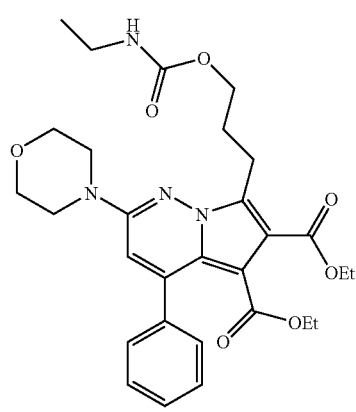

7-(3-Ethylcarbamoyloxy-propyl)-2-morpholin-4-yl-4-phenyl-pyrrolo[1,2-b]pyridazine-5,6-dicarboxylic acid diethyl ester (47). Ethyl isocyanate (50 µL, 0.063 mmol) and diisopropylethyl amine (1 drop) were added to a solution of 41 (30 mg, 0.062 mmol) in CH$_3$CN (10 mL). The reaction mixture was heated at 50° C. for 18 h. The solvent was removed in vacuo and the residue was purified by flash chromatography (silica gel, 35% EtOAc/hexane) to provide the title compound as a white solid. $^1$H NMR (DMSO-d$_6$) δ 0.89 (t, J=7.1 Hz, 3H), 0.99 (t, J=7.2 Hz, 3H), 1.20 (t, J=7.1 Hz, 3H), 1.91 (m, 2H), 2.96 (m, 2H), 3.22 (m, 2H), 3.53 (m, 6H), 3.71 (m, 4H), 3.96 (m, 2H), 4.19 (q, J=7.1 Hz, 2H), 6.78 (s, 1H), 7.00 (m, 1H), 7.41 (m, 2H), 7.46 (m, 3H). Mass Spectrum (ESI+) m/e=553.2 (M+H).

Example 48

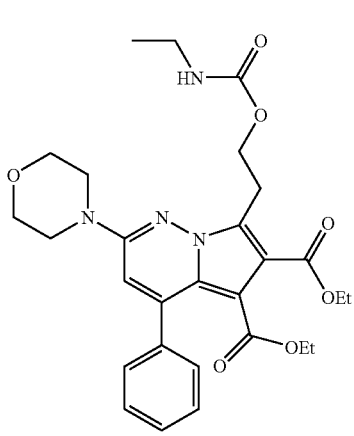

7-(2-Ethylcarbamoyloxy-ethyl)-2-morpholin-4-yl-4-phenyl-pyrrolo[1,2-b]pyridazine-5,6-dicarboxylic acid diethyl ester (48). The title compound was prepared from 42 as described in Example 47. $^1$H NMR (DMSO-$d_6$) δ 0.89 (t, J=7.1 Hz, 3H), 0.97 (t, J=7.2 Hz, 3H), 1.20 (t, J=7.1 Hz, 3H), 2.96 (m, 2H), 3.51 (m, 8H), 3.71 (m, 4H), 4.17 (q, J=7.1 Hz, 2H), 4.25 (m, 2H), 6.80 (s, 1H), 7.00 (m, 1H), 7.40 (m, 2H), 7.47 (m, 3H). Mass Spectrum (ESI+) m/e=539.2 (M+H).

Example 49

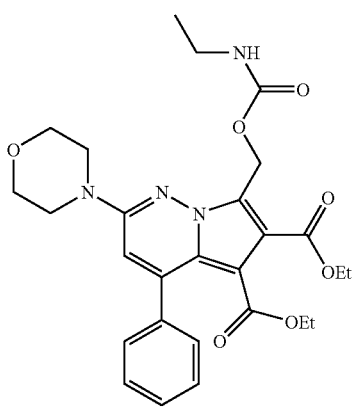

7-(Ethylcarbamoyloxy-methyl)-2-morpholin-4-yl-4-phenyl-pyrrolo[1,2-b]pyridazine-5,6-dicarboxylic acid diethyl ester (49). The title compound was prepared from 43 as described in Example 47. $^1$H NMR (DMSO-$d_6$) δ 0.90 (t, J=7.1 Hz, 3H), 0.99 (t, J=7.2 Hz, 3H), 1.21 (t, J=7.1 Hz, 3H), 3.0 (m, 2H), 3.54 (m, 6H), 3.69 (m, 4H), 4.17 (q, J=7.1 Hz, 2H), 5.53 (s, 2H), 6.89 (s, 1H), 7.09 (m, 1H), 7.40 (m, 2H), 7.47 (m, 3H). Mass Spectrum (ESI+) m/e=436.1 ([M+H]—$C_3H_6NO_2$).

Example 50

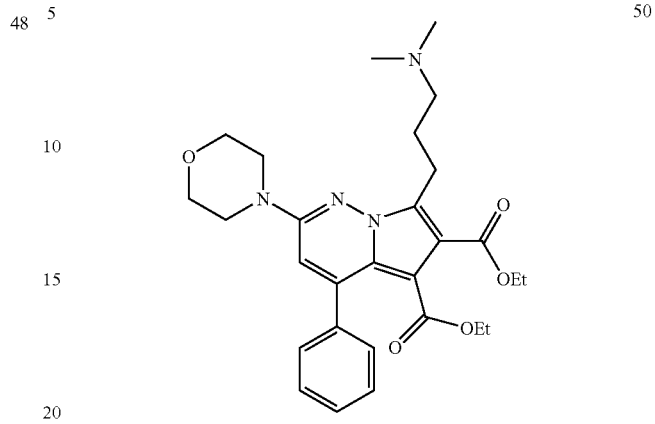

7-(3-Dimethylamino-propyl)-2-morpholin-4-yl-4-phenyl-pyrrolo[1,2-b]pyridazine-5,6-dicarboxylic acid diethyl ester (50). Methanesulfonic anhydride (136 mg, 0.78 mmol) and NEt$_3$ (145 μL, 1.04 mmol) were added to a solution of 41 (125 mg, 0.26 mmol) in CH$_2$Cl$_2$ (15 mL) at 0° C. under a nitrogen atmosphere. The reaction mixture was stirred at 0° C. for 30 min. and at ambient temperature for 8 h. The reaction mixture was diluted with CH$_2$Cl$_2$ (20 mL) and washed with saturated aqueous NaHCO$_3$, brine, dried (MgSO$_4$), filtered, and concentrated in vacuo to provide a yellow oil. A solution of the oil (68.5 mg, 0.122 mmol) in a 30% ethanolic HNMe$_2$ solution was heated at 60° C. in a sealed tube for 16 h. The excess HNMe$_2$ was removed by bubbling nitrogen through the solution. The solvent was removed in vacuo and the resulting oil was purified by flash chromatography (silica gel, 5% MeOH/CH$_2$Cl$_2$) to provide the title compound. $^1$H NMR (DMSO-$d_6$) δ 0.89 (t, J=7.1 Hz, 3H), 1.20 (t, J=7.1 Hz, 3H), 1.83 (m, 2H), 2.32 (bs, 6H), 3.17 (m, 2H), 3.30 (m, 2H), 3.53 (m, 6H), 3.72 (m, 4H), 4.17 (q, J=7.1 Hz, 2H), 6.78 (s, 1H), 7.40 (m, 2H), 7.46 (m, 3H). Mass Spectrum (ESI+) m/e=509.2 (M+H).

Example 51

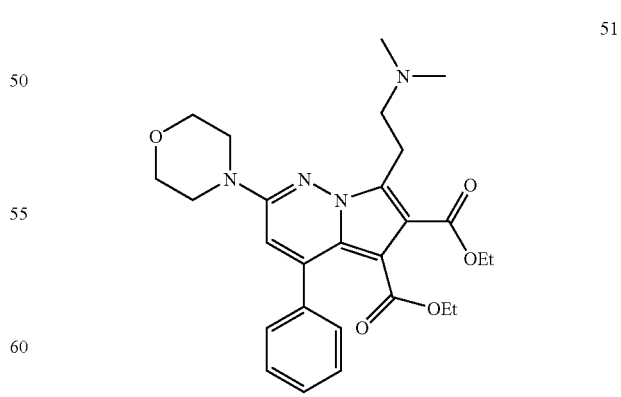

7-(2-Dimethylamino-ethyl)-2-morpholin-4-yl-4-phenyl-pyrrolo[1,2-b]pyridazine-5,6-dicarboxylic acid diethyl ester (51). The title compound was prepared from 42 as described in Example 50. $^1$H NMR (DMSO-$d_6$) δ 0.89 (t, J=7.1 Hz, 3H), 1.21 (t, J=7.1 Hz, 3H), 2.30 (bs, 6H), 3.30 (m, 4H), 3.52 (m, 6H), 3.72 (m, 4H), 4.17 (q, J=7.1 Hz, 2H), 6.78 (s, 1H), 7.40 (m, 2H), 7.46 (m, 3H). Mass Spectrum (ESI+) m/e=495.1 (M+H).

Example 52

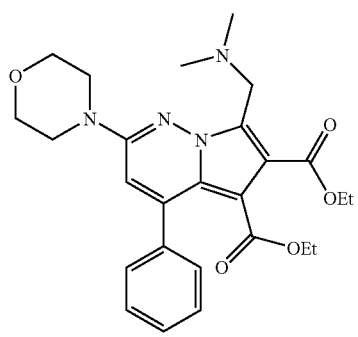

7-(Dimethylamino-methyl)-2-morpholin-4-yl-4-phenyl-pyrrolo[1,2-b]pyridazine-5,6-dicarboxylic acid diethyl ester (52). The title compound was prepared from 43 as described in Example 50. $^1$H NMR (DMSO-d$_6$) δ 0.88 (t, J=7.1 Hz, 3H), 1.22 (t, J=7.1 Hz, 3H), 2.20 (bs, 6H), 3.51 (m, 6H), 3.72 (m, 4H), 3.98 (bs, 2H), 4.17 (q, J=7.1 Hz, 2H), 6.83 (s, 1H), 7.40 (m, 2H), 7.47 (m, 3H). Mass Spectrum (ESI+) m/e=481.2 (M+H).

Example 53

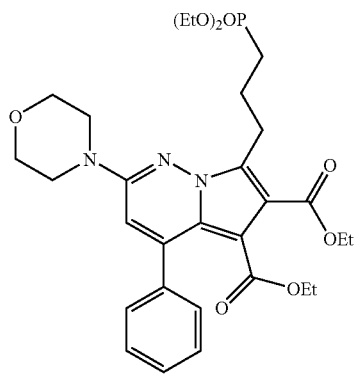

7-[3-(Diethoxyphosphoryl)-propyl]-2-morpholin-4-yl-4-phenyl-pyrrolo[1,2-b]pyridazine-5,6-dicarboxylic acid diethyl ester (53). Methanesulfonic anhydride (136 mg, 0.78 mmol) and NEt$_3$ (145 μL, 1.04 mmol) were added to a solution of 41 (125 mg, 0.26 mmol) in CH$_2$Cl$_2$ (15 mL) at 0° C. under a nitrogen atmosphere. The reaction mixture was stirred at 0° C. for 30 min. and at ambient temperature for 8 h. The reaction mixture was diluted with CH$_2$Cl$_2$ (20 mL) and washed with saturated aqueous NaHCO$_3$, brine, dried (MgSO$_4$), filtered, and concentrated in vacuo to provide a yellow oil. A mixture of the oil (68.5 mg, 0.122 mmol) and NaI (183 mg, 1.22 mmol) in P(OEt)$_3$ (5 mL) was heated at 120° C. for 24 h. The P(OEt)$_3$ was removed in vacuo and the residue was purified by flash chromatography (silica gel, 0-4% MeOH/CH$_2$Cl$_2$) to provide the title compound. $^1$H NMR (DMSO-d$_6$) δ 0.89 (t, J=7.2 Hz, 3H), 1.20 (m, 9H), 1.85 (m, 2H), 3.24 (m, 2H), 3.52 (m, 6H), 3.71 (m, 4H), 3.94 (m, 6H), 4.17 (q, J=7.1 Hz, 2H), 6.79 (s, 1H), 7.40 (m, 2H), 7.46 (m, 3H). Mass Spectrum (ESI+) m/e=602.2 (M+H).

Example 54

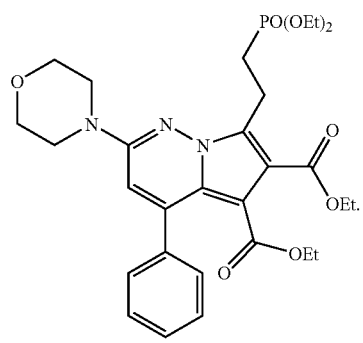

7-[2-(Diethoxyphosphoryl)-ethylyl]-2-morpholin-4-yl-4-phenyl-pyrrolo[1,2-b]pyridazine-5,6-dicarboxylic acid diethyl ester (54). The title compound was prepared from 42 as described in Example 53. $^1$H NMR (DMSO-d$_6$) δ 0.89 (t, J=7.2 Hz, 3H), 1.21 (m, 9H), 2.60 (m, 2H), 3.53 (m, 6H), 3.72 (m, 4H), 4.00 (m, 6H), 4.17 (q, J=7.1 Hz, 2H), 6.80 (s, 1H), 7.40 (m, 2H), 7.46 (m, 3H). Mass Spectrum (ESI+) m/e=588.2 (M+H).

Example 55

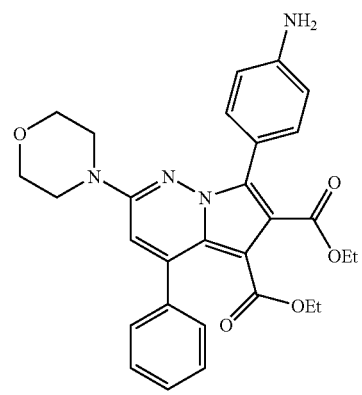

7-(4-Aminophenyl)-2-morpholin-4-yl-4-phenyl-pyrrolo[1,2-b]pyridazine-5,6-dicarboxylic acid diethyl ester (55). HCO$_2$NH$_4$ (29 mg, 0.459 mmol) was added to a suspension of 9 (50 mg, 0.092 mmol) and 10% Pd/C (10 mg) in EtOH (10 mL). The reaction mixture was stirred at ambient temperature for 24 h. The reaction mixture was filtered through celite and the filtrate was concentrated in vacuo. The resulting residue was triturated in (1:1) Et$_2$O/hexane and the resulting precipitate was collected by vacuum filtration to provide the title compound as a yellow solid. $^1$H NMR (DMSO-d$_6$) δ 0.84 (t, J=7.1 Hz, 3H), 1.09 (t, J=7.0 Hz, 3H), 3.39 (m, 4H), 3.51 (q, J=7.1 Hz, 2H), 3.67 (m, 4H), 4.07 (q, J=7.2 Hz, 2H), 6.60 (d, J=8.4 Hz, 2H), 6.80 (s, 1H), 7.27 (d, J=8.3 Hz, 2H), 7.44 (m, 5H). Mass Spectrum (ESI+) m/e=515.3 (M+H).

Example 56

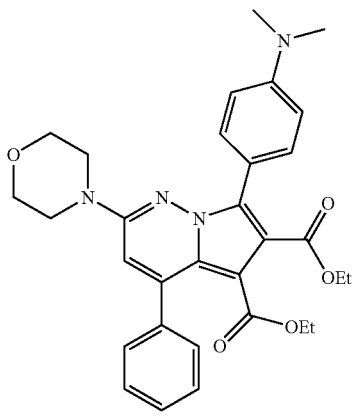

7-(4-Dimethylamino-phenyl)-2-morpholin-4-yl-4-phenyl-pyrrolo[1,2-b]pyridazine-5,6-dicarboxylic acid diethyl ester (56). To a solution of 55 (78 mg, 0.152 mmol) in $CH_3CN$ (10 mL) was added 37% aqueous $CH_2O$ (123 μL, 1.52 mmol), $NaBH_3CN$ (29 mg, 0.450 mmol), and AcOH (31 μL, 0.531 mmol). The reaction mixture was stirred at ambient temperature for 2 h. $Et_2O$ was added and the solution was washed with saturated aqueous $NaHCO_3$, brine, dried ($MgSO_4$), filtered, and concentrated in vacuo to provide a yellow oil. Purification by flash chromatography (silica gel, 40% EtOAc/hexane) provided an off-white solid. The solid was suspended in (1:1) $Et_2O$/hexane, collected by vacuum filtration and washed with hexane to provide the title compound as an off-white solid. $^1$H NMR (DMSO-$d_6$) δ 0.85 (t, J=7.1 Hz, 3H), 1.10 (t, J=7.1 Hz, 3H), 2.96 (s, 6H), 3.40 (m, 4H), 3.51 (q, J=7.2 Hz, 2H), 3.67 (m, 4H), 4.07 (q, J=7.1 Hz, 2H), 6.77 (d, J=9.0 Hz, 2H), 6.82 (s, 1H), 7.44-7.48 (m, 7H). Mass Spectrum (ESI+) m/e=543.2 (M+H).

Example 57

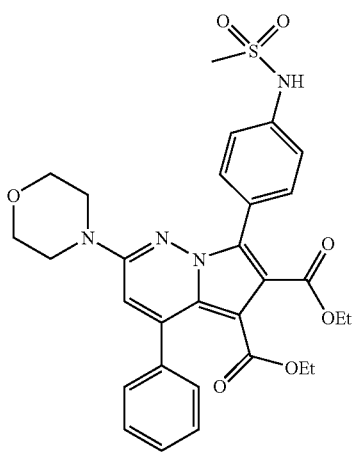

7-(4-Methylsulfonylaminophenyl)-2-morpholin-4-yl-4-phenyl-pyrrolo[1,2-b]pyridazine-5,6-dicarboxylic acid diethyl ester (57) Methanesulfonyl chloride (5.4 μL, 0.07 mmol) was added to a solution of 7-(4-aminophenyl)-2-morpholin-4-yl-4-phenyl-pyrrolo[1,2-b]pyridazine-5,6-dicarboxylic acid diethyl ester 55 (30 mg, 0.058 mmol) and $NEt_3$ (16 μL, 0.116 mmol) in $CH_2Cl_2$ (10 mL). The reaction mixture was stirred at ambient temperature for 12 h, quenched with water, and the layers separated. The organic layer was washed with saturated aqueous $NaHCO_3$, brine, dried ($MgSO_4$), filtered, concentrated in vacuo. Purification by flash chromatography (silica gel, 35% EtOAc/hexane) provided the title compound. $^1$H NMR (DMSO-$d_6$) δ 0.85 (t, J=7.1 Hz, 3H), 1.07 (t, J=7.1 Hz, 3H), 3.06 (s, 3H), 3.40 (m, 4H), 3.53 (q, J=7.1 Hz, 2H), 3.66 (m, 4H), 4.07 (q, J=7.1 Hz, 2H), 6.87 (s, 1H), 7.26 (d, J=8.6 Hz, 2H), 7.45 (m, 2H), 7.48 (m, 3H), 7.56 (d, J=8.6 Hz, 2H), 9.97 (bs, 1H). Mass Spectrum (ESI+) m/e=593.1 (M+H).

Example 58

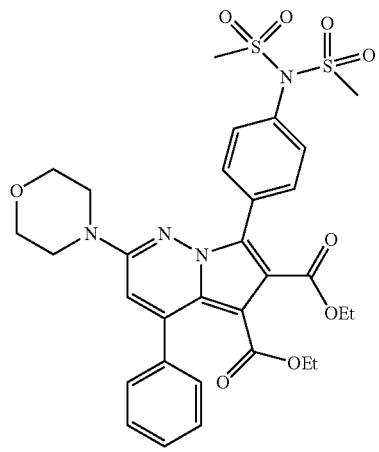

7-[4-Bis(methylsulfonyl)-aminophenyl]-2-morpholin-4-yl-4-phenyl-pyrrolo[1,2-b]pyridazine-5,6-dicarboxylic acid diethyl ester (58). The title compound was also obtained by the procedure described in Example 57. $^1$H NMR (DMSO-$d_6$) δ 0.87 (t, J=7.1 Hz, 3H), 1.06 (t, J=7.1 Hz, 3H), 3.42 (m, 4H), 3.53 (q, J=7.2 Hz, 2H), 3.57 (s, 6H), 3.66 (m, 4H), 4.08 (q, J=7.1 Hz, 2H), 6.92 (s, 1H), 7.47 (m, 5H), 7.61 (d, J=8.5 Hz, 2H), 7.74 (d. J=8.5 Hz, 2H), Mass Spectrum (ESI+) m/e=671.1 (M+H).

Example 59

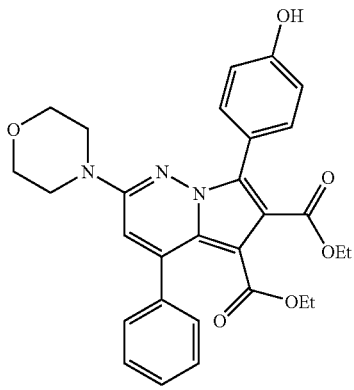

7-(4-Hydroxy-phenyl)-2-morpholin-4-yl-4-phenyl-pyrrolo[1,2-b]pyridazine-5,6-dicarboxylic acid diethyl ester (59). 10% Pd/C was added to a solution of 37 in 95% EtOH (20 mL). The reaction mixture was stirred at ambient temperature under a $H_2$ atmosphere for 24 h. The reaction mixture was filtered through celite and the filtrate was concentrated in vacuo. The resulting residue was triturated in 1:1 $Et_2O$/hexane and the precipitate was collected by vacuum filtration to provide the title compound as an off-white solid. $^1$H NMR (DMSO-$d_6$) δ 0.85 (t, J=7.1 Hz, 3H), 1.07 (t, J=7.1 Hz, 3H), 3.38 (m, 4H), 3.51 (q, J=7.2 Hz, 2H), 3.66 (m, 4H), 4.06 (q, J=7.1 Hz, 2H), 6.83 (m, 3H), 7.40-7.49 (m, 7H), 9.67 (s, 1H). Mass Spectrum (ESI+) m/e=516.3 (M+H).

Example 60

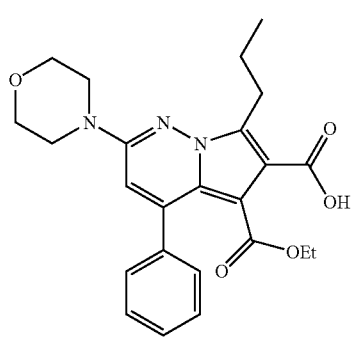

2-Morpholin-4-yl-4-phenyl-7-propyl-pyrrolo[1,2-b]pyridazine-5,6-dicarboxylic acid 5-ethyl ester (60). A mixture of 2-morpholin-4-yl-4-phenyl-7-propyl-pyrrolo[1,2-b]pyridazine-5,6-dicarboxylic acid diethyl ester (15) (3.9 g, 8.38 mmol) and 10 mL of a 2N solution of NaOH in 50 mL of ethanol and 30 mL of water was heated at reflux for 5 h. The reaction mixture was cooled to r.t. and concentrated to about half of the original volume. 25 mL of 1N HCl were added and the resulting precipitate was collected by vacuum filtration, washed with cold water and died in vacuo to provide the title compound as a solid. $^1$H NMR (DMSO-$d_6$) δ 1.04-1.10 (m, 6H), 1.79-1.87 (m, 2H), 3.34 (t, 2H, 7.3 Hz), 3.66-3.74 (m, 6H), 3.86-3.91 (m, 4H), 6.91 (s, 1H), 7.56-7.64 (m, 5H), 12.53 (brs, 1H). Mass Spectrum (ES+) m/e=460.1 (M+23).

Example 61

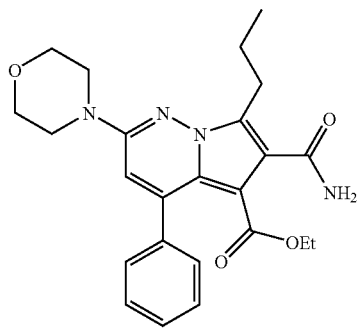

6-Carbamoyl-2-morpholin-4-yl-4-phenyl-7-propyl-pyrrolo[1,2-b]pyridazine-5-carboxylic acid ethyl ester (61). Oxalyl chloride (33 mL, 0.379 mmol) and DMF (1 drop) were added to a solution of 60 in $CH_2Cl_2$ (10 mL) at 0° C. The reaction mixture was stirred at ambient temperature for 1 h and concentrated in vacuo. THF (15 mL) was added followed by 28% aqueous $NH_4OH$ (5 mL). The reaction mixture was stirred at ambient temperature for 1 h and the layers were separated. The aqueous layer was extracted with EtOAc and the organic layers were pooled, dried ($MgSO_4$), filtered, and concentrated in vacuo to provide a yellow solid. Purification by flash chromatography (silica gel, 25-30-35% EtOAc/hexane) provided the title compound as an off-white solid. $^1$H NMR (CDCl$_3$) δ 0.79 (t, J=7.2 Hz, 3H), 1.04 (t, J=7.4 Hz, 3H), 1.78 (m, 2H), 3.36 (m, 4H), 3.54 (m, 4H), 3.88 (m, 4H), 5.31 (s, 2H), 6.47 (s, 1H), 7.48 (m, 5H). Mass Spectrum (ESI+) m/e=437.1 (M+H).

Example 62

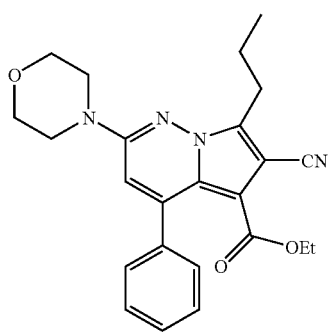

6-Cyano-2-morpholin-4-yl-4-phenyl-7-propyl-pyrrolo[1,2-b]pyridazine-5-carboxylic acid ethyl ester (62). Trifluoroacetic anhydride (36 μL, 0.252 mmol) was added dropwise via syringe to a solution of 61 (100 mg, 0.229 mmol) and NEt₃ (70 µL, 0.504 mmol) in THF (10 mL) at 0° C. The reaction mixture was stirred at ambient temperature for 48 h. Water was added, the layers were separated, and the aqueous layer was extracted with EtOAc. The organic layers were pooled, washed with brine, dried (MgSO₄), filtered, and concentrated in vacuo to provide a yellow oil. Purification by flash chromatography (silica gel, 20% EtOAc/hexane) provided the title compound. ¹H NMR (DMSO-d₆) δ 0.74 (t, J=7.2 Hz, 3H), 0.94 (t, J=7.4 Hz, 3H), 1.78 (m, 2H), 3.03 (t, J=7.3 Hz, 2H), 3.59 (m, 6H), 3.75 (m, 4H), 7.02 (s, 1H), 7.48 (m, 5H). Mass Spectrum (ESI+) m/e=419.1 (M+H).

Example 63

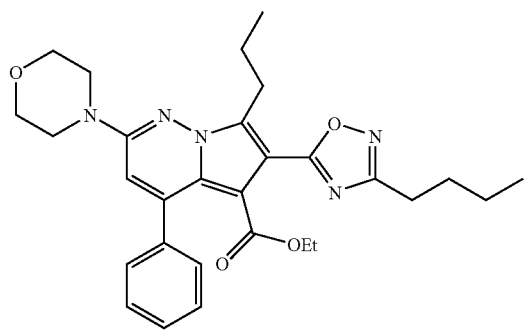

63

6-(3-Butyl-[1,2,4]oxadiazol-5-yl)-2-morpholin-4-yl-4-phenyl-7-propyl-pyrrolo[1,2-b]pyridazine-5-carboxylic acid ethyl ester (63). Oxalyl chloride (33 µL, 0.379 mmol) and DMF (1 drop) were added to a solution of 2-morpholin-4-yl-4-phenyl-7-propyl-pyrrolo[1,2-b]pyridazine-5,6-dicarboxylic acid 5-ethyl ester (60) (200 mg, 0.457 mmol) in CH₂Cl₂ (20 mL) at 0° C. The reaction mixture was stirred at ambient temperature for 1.5 h and concentrated in vacuo to provide the acid chloride. N-hydroxypentanamidine (Boschelli et al. (1993) *Heterocycles* 35(1):121-124) (423 mg, 3.64 mmol) was added to a solution of the acid chloride (50 mg, 0.11 mmol) in THF (10 mL) followed by NEt₃ (38 µL, 0.274 mmol). The reaction mixture was stirred at ambient temperature for 1 h and quenched with saturated aqueous NH₄Cl (10 mL). The layers were separated and the aqueous layer was extracted with EtOAc. The organic layers were pooled, washed with brine, dried (MgSO₄), filtered, and concentrated in vacuo to provide a yellow oil. The yellow oil was dissolved in THF (20 mL) and TBAF (1.64 mmol) was added. The reaction mixture was stirred at ambient temperature for 48 h and concentrated in vacuo to provide a yellow oil. Purification by flash chromatography (silica gel, 25% EtOAC/hexane) yielded the the title compound. ¹H NMR (DMSO-d₆) δ 0.87 (m, 9H), 1.34 (m, 2H), 1.68 (m, 4H), 2.72 (t, J=7.4 Hz, 2H), 3.21 (m, 2H), 3.56 (m, 6H), 3.73 (m, 4H), 6.87 (s, 1H), 7.44 (m, 2H), 7.47 (m, 3H). Mass Spectrum (ESI+) m/e=518.2 (M+H).

Example 64

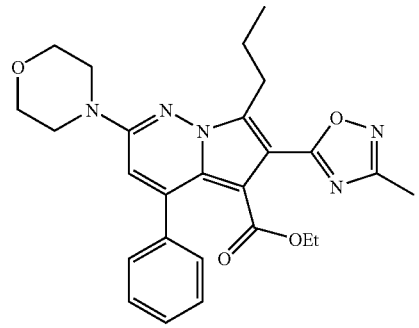

64

6-(3-Methyl-[1,2,4]oxadiazol-5-yl)-2-morpholin-4-yl-4-phenyl-7-propyl-pyrrolo[1,2-b]pyridazine-5-carboxylic acid ethyl ester (64). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. ¹H NMR (DMSO-d₆) δ 0.92-0.99 (m, 6H), 1.76-1.83 (m, 2H), 2.45 (s, 3H), 3.29 (t, 2H, J=7.3 Hz). 3.60-3.66 (m, 4H), 3.67 (q, 2H, J=7.0 Hz), 3.80-3.83 (m, 4H), 6.95 (s, 1H), 7.51-7.58 (m, 5H). Mass Spectrum (ES+) m/e=476.2 (M+H).

Example 65

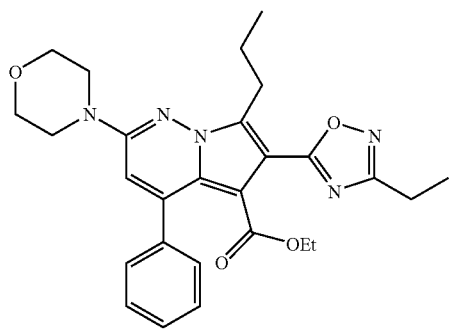

65

6-(3-Ethyl-[1,2,4]oxadiazol-5-yl)-2-morpholin-4-yl-4-phenyl-7-propyl-pyrrolo[1,2-b]pyridazine-5-carboxylic acid ethyl ester (65). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. ¹H NMR (DMSO-d₆) δ 1.05 (t, 3H, J=7.2 Hz), 1.07 (t, 3H, J=7.2 Hz), 1.43 (t, 3H, J=7.6 Hz), 1.86-1.92 (m, 2H), 2.92 (q, 2H, J=7.7 Hz), 3.40 (t, 2H, J=7.3 Hz), 3.71-3.74 (m, 4H), 3.75 (q, 2H, J=7.3 Hz), 3.90-3.93 (m, 4H), 7.05 (s, 1H), 7.60-7.67 (m, 5H). Mass Spectrum (ES+) m/e=490.2 (M+H).

Example 66

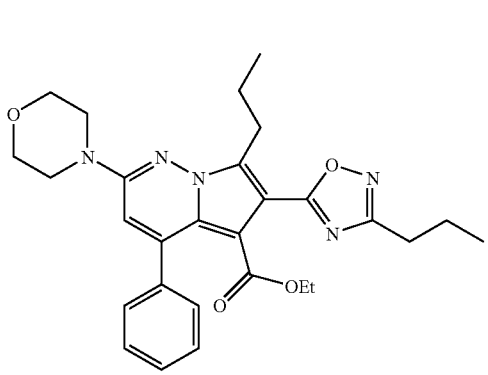

2-Morpholin-4-yl-4-phenyl-6-(3-propyl-[1,2,4] oxadiazol-5-yl)-7-propyl-pyrrolo[1,2-b]pyridazine-5-carboxylic acid ethyl ester (66). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-d$_6$) δ 1.02-1.07 (m, 6H), 1.12 (t, 3H, J=7.3 Hz), 1.85-1.93 (m, 4H), 2.88 (t, 2H, J=7.3 Hz), 3.39 (t, 2H, J=7.6 Hz), 3.71-3.74 (m, 4H), 3.76 (q, 2H, J=7.0 Hz), 3.90-3.92 (m, 4H), 7.05 (s, 1H), 7.61-7.66 (m, 5H). Mass Spectrum (ES+) m/e=504.1 (M+H).

Example 67

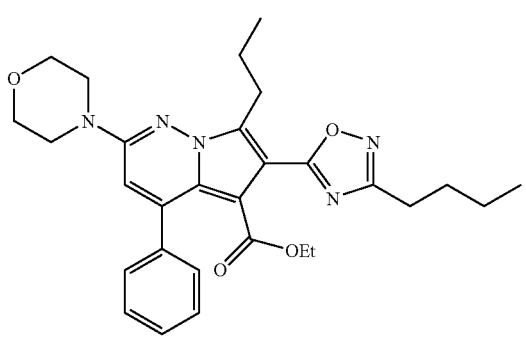

2-Morpholin-4-yl-6-(3-pentyl-[1,2,4]oxadiazol-5-yl)-4-phenyl-7-propyl-pyrrolo[1,2-b]pyridazine-5-carboxylic acid ethyl ester (67). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-d$_6$) δ 0.88 (m, 9H), 1.33 (m, 4H), 1.72 (m, 4H), 2.74 (t, J=7.3 Hz, 2H), 3.23 (m, 2H), 3.57 (m, 4H), 3.61 (q, J=7.2 Hz, 2H), 3.76 (m, 4H), 6.90 (s, 1H), 7.47 (m, 2H), 7.50 (m, 3H). Mass Spectrum (ESI+) m/e=532.2 (M+H).

Example 68

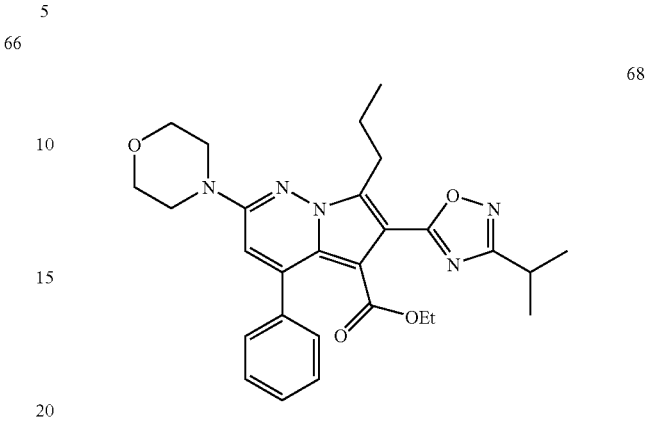

6-(3-Isopropyl-[1,2,4]oxadiazol-5-yl)-2-morpholin-4-yl-4-phenyl-7-propyl-pyrrolo[1,2-b]pyridazine-5-carboxylic acid ethyl ester (68). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-d$_6$) δ 1.04-1.09 (m, 6H), 1.46 (d, 6H, J=6.9 Hz), 1.86-1.92 (m, 2H), 3.24-3.29 (m, 1H), 3.40 (t, 2H, J=7.0 Hz), 3.71-3.74 (m, 4H), 3.77 (q, 2H, J=7.1 Hz), 3.90-3.93 (m, 4H), 7.05 (s, 1H). 7.60-7.67 (m, 5H). Mass Spectrum (ES+) m/e=504.1 (M+H).

Example 69

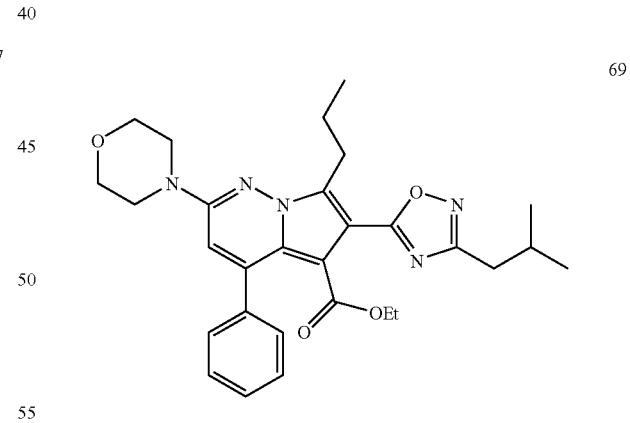

6-(3-Isobutyl-[1,2,4]oxadiazol-5-yl)-2-morpholin-4-yl-4-phenyl-7-propyl-pyrrolo[1,2-b]pyridazine-5-carboxylic acid ethyl ester (69). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-d$_6$) δ 0.89 (m, 6H), 0.97 (d, J=6.7 Hz, 6H), 1.72 (m, 2H), 2.10 (m, 1H), 2.63 (d, J=7.0 Hz, 2H), 3.23 (m, 2H), 3.58 (m, 6H), 3.76 (m, 4H), 6.90 (s, 1H), 7.47 (m, 2H), 7.50 (m, 3H). Mass Spectrum (ESI+) m/e=518.2 (M+H).

Example 70

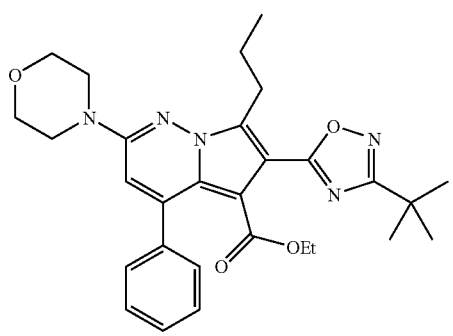

6-(3-tert-Butyl-[1,2,4]oxadiazol-5-yl)-2-morpholin-4-yl-4-phenyl-7-propyl-pyrrolo[1,2-b]pyridazine-5-carboxylic acid ethyl ester (70). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-$d_6$) δ 1.04-1.10 (m, 6H), 1.51 (s, 9H), 1.87-1.91 (m, 2H), 3.40 (t, 2H, J=7.4 Hz), 3.71-3.76 (m, 6H), 3.90-3.92 (m, 4H), 7.04 (s, 1H), 7.61-7.66 (m, 5H). Mass Spectrum (ES+) m/e=518.2 (M+H).

Example 71

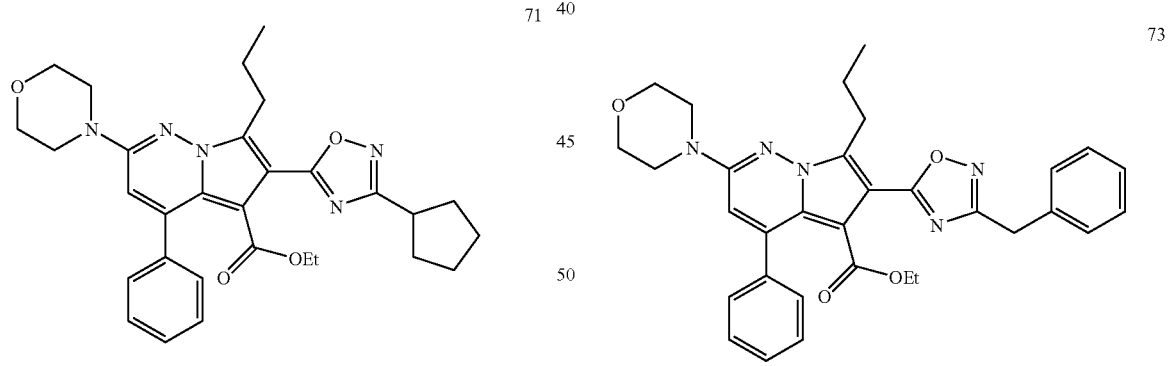

6-(3-Cyclopentyl-[1,2,4]oxadiazol-5-yl)-2-morpholin-4-yl-4-phenyl-7-propyl-pyrrolo[1,2-b]pyridazine-5-carboxylic acid ethyl ester (71). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-$d_6$) δ 1.03-1.08 (m, 6H), 1.82-1.93 (m, 8H), 2.17-2.20 (m, 2H), 3.39 (t, 2H, J=7.0 Hz), 3.42-3.45 (m, 1H), 3.72-3.78 (m, 6H), 3.89-3.92 (m, 4H), 7.05 (s, 1H), 7.60-7.67 (m, 5H). Mass Spectrum (ES+) m/e=530.2 (M+H).

Example 72

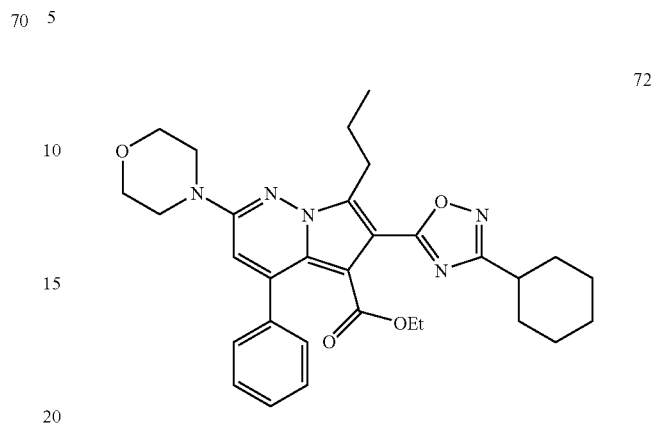

6-(3-Cyclohexyl-[1,2,4]oxadiazol-5-yl)-2-morpholin-4-yl-4-phenyl-7-propyl-pyrrolo[1,2-b]pyridazine-5-carboxylic acid ethyl ester (72). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-$d_6$) δ 1.02-1.08 (m, 6H), 1.41-1.95 (m, 10H), 2.12-2.15 (m, 2H), 2.96-3.00 (m, 1H), 3.37-3.44 (m, 2H), 3.71-3.79 (m, 6H), 3.89-3.92 (m, 4H), 7.04 (s, 1H), 7.60-7.66 (m, 5H). Mass Spectrum (ES+) m/e=544.2 (M+H).

Example 73

6-(3-Benzyl-[1,2,4]oxadiazol-5-yl)-2-morpholin-4-yl-4-phenyl-7-propyl-pyrrolo[1,2-b]pyridazine-5-carboxylic acid ethyl ester (73). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-$d_6$) δ 0.99 (t, 3H, J=7.0 Hz), 1.02 (t, 3H, J=7.2 Hz), 1.83-1.86 (m, 2H), 3.36 (t, 2H, J=7.4 Hz), 3.68-3.72 (m, 6H), 3.89-3.92 (m, 4H), 4.29 (s, 2H), 7.04 (s, 1H), 7.40-7.51 (m, 5H), 7.59-7.66 (m, 5H). Mass Spectrum (ES+) m/e=552.3 (M+H).

Example 74

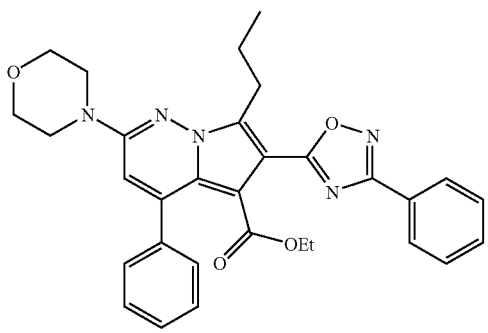

2-Morpholin-4-yl-4-phenyl-6-(3-phenyl-[1,2,4]oxadiazol-5-yl)-7-propyl-pyrrolo[1,2-b]pyridazine-5-carboxylic acid ethyl ester (74). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-$d_6$) δ 0.98 (t, 3H, J=7 Hz), 1.03 (t, 3H, J=7.4 Hz), 1.88-1.89 (m, 2H), 3.37-3.39 (m, 2H), 3.65-3.66 (m, 4H), 3.71 (q, 2H, J=7.4 Hz), 3.81-3.83 (m, 2H), 6.98 (s, 1H), 7.54-56 (m, 5H), 7.66-7.69 (m, 3H), 8.12 (dd, 2H, J1=1.8 Hz, J2=7.8 Hz). Mass Spectrum (ES+) m/e=538.2 (M+H).

Example 75

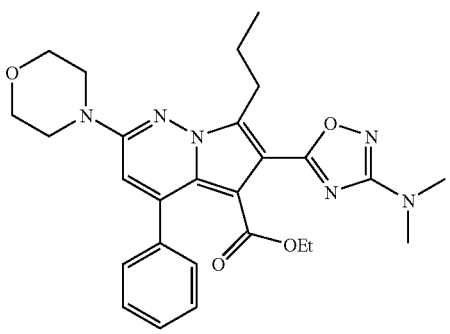

6-(3-Dimethylamino-[1,2,4]oxadiazol-5-yl)-2-morpholin-4-yl-4-phenyl-7-propyl-pyrrolo[1,2-b]pyridazine-5-carboxylic acid ethyl ester (75). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-$d_6$) δ 1.06 (t, 3H, J=7.1 Hz), 1.08 (t, 3H, J=7.4 Hz), 1.86-1.90 (m, 2H), 3.11 (s, 6H), 3.38 (t, 2H, J=7.6 Hz), 3.70-3.76 (m, 6H), 3.89-3.92 (m, 4H), 7.02 (s, 1H), 7.60-7.66 (m, 5H). Mass Spectrum (ES+) m/e=505.2 (M+H).

Example 76

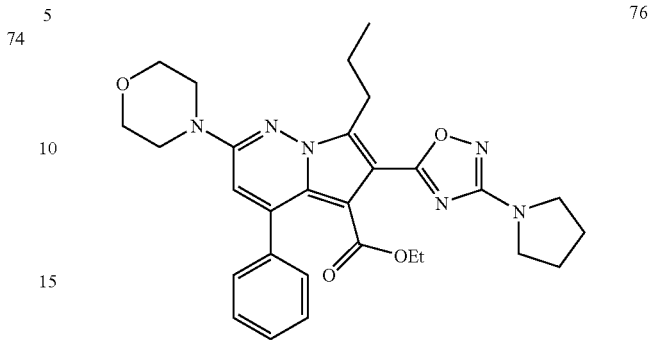

2-Morpholin-4-yl-4-phenyl-7-propyl-6-(3-pyrrolidin-1-yl-[1,2,4]oxadiazol-5-yl)-pyrrolo[1,2-b]pyridazine-5-carboxylic acid ethyl ester (76). The title compound was prepared from 2-morpholin-4-yl-4-phenyl-7-propyl-pyrrolo[1,2-b]pyridazine-5,6-dicarboxylic acid 5-ethyl ester (60) and the corresponding amidine, as described in Example 63. $^1$H NMR (DMSO-$d_6$) δ 1.04-1.11 (m, 6H), 1.86-1.91 (m, 2H), 2.07-2.11 (m, 4H), 3.36 (t, 2H, J=7.6 Hz), 3.48-3.53 (m, 4H), 3.70-3.78 (m, 6H), 3.90-3.92 (m, 4H), 7.02 (s, 1H), 7.59-7.66 (m, 5H). Mass Spectrum (ES+) m/e=531.2 (M+H).

Example 77

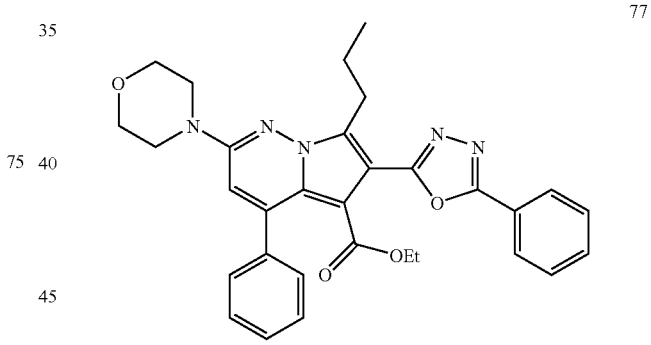

2-Morpholin-4-yl-4-phenyl-6-(5-phenyl-[1,3,4]oxadiazol-2-yl)-7-propyl-pyrrolo[1,2-b]pyridazine-5-carboxylic acid ethyl ester (77). Oxalyl chloride (40 μL, 0.46 mmol) and DMF (1 drop) were added to a solution of 2-morpholin-4-yl-4-phenyl-7-propyl-pyrrolo[1,2-b]pyridazine-5,6-dicarboxylic acid 5-ethyl ester (60) (97.2 mg, 0.22 mmol) in $CH_2Cl_2$ (5 mL) at 0° C. The reaction mixture was stirred at ambient temperature for 1.5 h and concentrated in vacuo to provide the acid chloride. Benzoic acid hydrazide (46 mg, 0.34 mmol) was added to a solution of the acid chloride in THF (5 mL) followed by $NEt_3$ (46 μL, 0.66 mmol). The reaction mixture was stirred at ambient temperature for 1 h and quenched with saturated aqueous $NH_4Cl$ (10 mL). The layers were separated and the aqueous layer was extracted with EtOAc. The organic layers were pooled, washed with brine, dried ($MgSO_4$), filtered, and concentrated in vacuo to provide a yellow solid. This solid was dissolved in N-methylpyrrolidine (2 mL) and phosphorous pentoxide (20 mg) was added. The reaction mixture was heated to 180° C. for 48 h and concentrated in vacuo. Purification by flash chromatography (silica gel, 25% EtOAc/hexane) yielded the title compound. ¹H NMR (DMSO-d₆) δ 0.97 (t, 3H, J 7.0 Hz), 1.11 (t, 3H, J=7.3 Hz), 1.91-1.98 (m, 2H), 3.37-3.41 (m, 2H), 3.71-3.74 (m, 6H), 3.91-3.92 (m, 4H), 7.07 (s, 1H), 7.66 (m, 5H), 7.78-7.81 (m, 3H), 8.12-8.14 (m, 2H). Mass Spectrum (ES+) m/e=538.2 (M+H).

Example 78

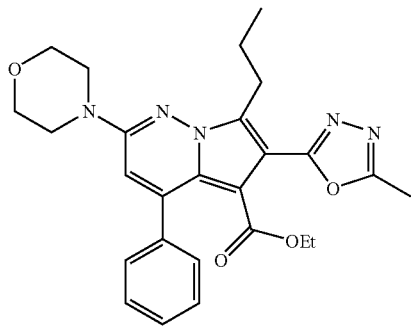

6-(5-Methyl-[1,3,4]oxadiazol-2-yl)-2-morpholin-4-yl-4-phenyl-7-propyl-pyrrolo[1,2-b]pyridazine-5-carboxylic acid ethyl ester (78). The title compound was prepared according to the procedure described in Example 77. ¹H NMR (DMSO-d₆) δ 0.98-1.08 (m, 6H), 1.85-1.91 (m, 2H), 2.67 (s, 3H), 3.28 (t, 2H, J=7.4 Hz), 3.70-3.77 (m, 6H), 3.90-3.93 (m, 4H), 7.04 (s, 1H), 7.61-7.66 (m, 5H). Mass Spectrum (ES+) m/e=476.1 (M+H).

Example 79

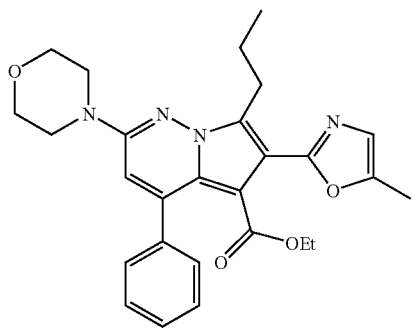

6-(5-Methyl-oxazol-2-yl)-2-morpholin-4-yl-4-phenyl-7-propyl-pyrrolo[1,2-b]pyridazine-5-carboxylic acid ethyl ester (79). Oxalyl chloride (0.1 mL, 1.1 mmol) and DMF (1 drop) were added to a solution of 2-morpholin-4-yl-4-phenyl-7-propyl-pyrrolo[1,2-b]pyridazine-5,6-dicarboxylic acid 5-ethyl ester (60) (52 mg, 0.12 mmol) in CH₂Cl₂ (2 mL) at 0° C. The reaction mixture was stirred at ambient temperature for 1.5 h and concentrated in vacuo to provide the acid chloride. This was dissolved in 2 mL of THF, 1-aminopropan-2-one hydrochloride (150 mg, 1.37 mmol) and Et₃N (0.2 mL, 1.4 mmol) were added. The reaction mixture was stirred at ambient temperature for 2 h and quenched by addition of saturated aqueous NH₄Cl (10 mL). The layers were separated and the aqueous layer was extracted with EtOAc. The organic layers were pooled, washed with brine, dried (MgSO₄), filtered, and the filtrate was concentrated in vacuo to provide an oil. Concentrated sulfuric acid (1 mL) was added and the reaction mixture was stirred at ambient temperature for 1.5 h and poured into 10 mL of water and brought to pH ~8 by addition of saturated aqueous solution of NaHCO₃. The mixture was extracted with EtOAc. The organic layers were pooled, washed with brine, dried (MgSO₄), filtered, and the filtrate was concentrated. Purification by flash chromatography (silica gel, EtOAc/hexane=⅓) gave the title compound. ¹H NMR (DMSO-d₆) δ 1.03-1.07 (m, 6H), 1.83-1.88 (m, 2H), 2.45 (s, 3H), 3.34 (t, 2H, J=7.1 Hz), 3.68-3.70 (m, 4H), 3.75 (q, 2H, J=7.2 Hz), 3.89-3.92 (m, 4H), 6.95 (s, 1H), 7.09 (s, 1H), 7.59-7.65 (m, 5H). Mass Spectrum (ES+) m/e=475.2 (M+H).

Example 80

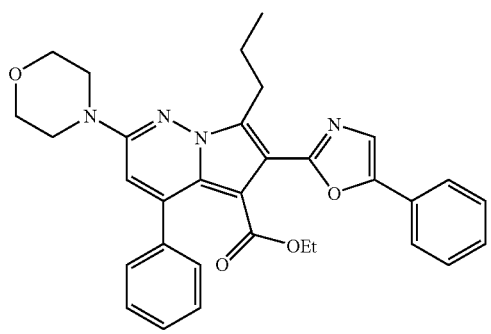

2-Morpholin-4-yl-4-phenyl-6-(5-phenyl-oxazol-2-yl)-7-propyl-pyrrolo[1,2-b]pyridazine-5-carboxylic acid ethyl ester (80). The title compound was prepared according to procedures described in Example 79. ¹H NMR (DMSO-d₆) δ 0.91 (t, 3H, J=7.0 Hz), 1.02 (t, 3H, J=7.3 Hz), 1.81-1.86 (m, 2H), 3.34-3.38 (m, 2H), 3.60-3.67 (m, 6H), 3.82 (dd, 4H, J1=4.3 Hz, J2=4.8 Hz), 6.89 (s, 1H), 7.42 (dd, 1H, J1=7.0 Hz, J2=7.2 Hz), 7.52-7.56 (m, 7H), 7.72 (d, 2H, J=7.4 Hz), 7.86 (s, 1H). Mass Spectrum (ES+) m/e 537.2 (M+H).

Example 81

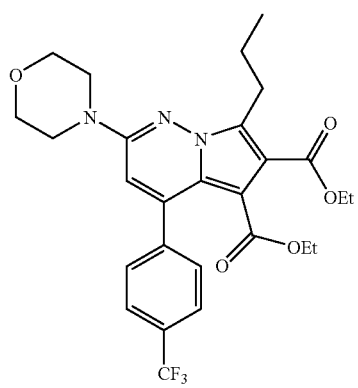

2-Morpholin-4-yl-7-propyl-4-(4-trifluoromethyl-phenyl)-pyrrolo[1,2-b]pyridazine-5,6-dicarboxylic acid diethyl ester (81)

Step A. 3-(4-Trifluoromethyl-phenyl)-furan-2,5-dione. A mixture of 4-(trifluoromethyl)phenylacetonitrile (9.26 g, 50 mmol), glyoxylic acid monohydrate (6.9 g, 75 mmol), and potassium carbonate (17 g, 125 mmol) in methanol (100 mL) was stirred at room temperature for 3-5 h. The resulting thick solid precipitate was filtered and washed with dichloromethane. This solid was suspended in 250 mL of water, stirred overnight, and filtered and air-dried to provide 3-cyano-3-(4-trifluoromethyl-phenyl)-acrylic acid potassium salt. This was dissolved in 88% formic acid (ca. 200 mL) containing concentrated sulfuric acid (15 mL). This mixture was heated at reflux for 2-3 h and cooled and poured into ice water. The resulting precipitate was collected by filtration, washed with water, and air dried to provide the title compound. $^1$H NMR (DMSO-$d_6$) δ 7.94 (s, 1H), 7.97 (d, J=8.2 Hz, 2H), 8.24 (d, J=8.2 Hz, 2H).

Step B. 4-(4-Trifluoromethyl-phenyl)-pyridazine-3,6-diol. The title compound was prepared from 3-(4-trifluoromethyl-phenyl)-furan-2,5-dione as described in Example 1, Step A. $^1$H NMR (DMSO-$d_6$) δ 7.34 (br s, 1H), 7.82 (d, J=8.4 Hz, 2H), 8.06 (br s, 2H), 11.04 (br s, 1H), 12.28 (br s, 1H).

Step C. 3,6-Dichloro-4-(4-trifluoromethyl-phenyl)-pyridazine. The title compound was prepared from 4-(4-trifluoromethyl-phenyl)-pyridazine-3,6-diol as described in Example 1, Step B. $^1$H NMR (DMSO-$d_6$) δ 7.87 (d, J=8.2 Hz, 2H), 7.97 (d, J=8.2 Hz, 2H), 8.24 (s, 1H).

Step D. 4-[6-Chloro-5-(4-trifluoromethyl-phenyl)-pyridazin-3-yl]-morpholine. The title compound was prepared from 3,6-dichloro-4-(4-trifluoromethyl-phenyl)-pyridazine as described in Example 1, Step C. $^1$H NMR (DMSO-$d_6$) δ 3.64 (t, J=5.2 Hz, 4H), 3.74 (t, J=5.2 Hz, 4H), 7.46 (s, 1H), 7.80 (d, J=8.1 Hz, 2H), 7.92 (d, J=8.1 Hz, 2H).

Step E. 4-[5-(4-Trifluoromethyl-phenyl)-pyridazin-3-yl]-morpholine. The title compound was prepared from 4-[6-chloro-5-(4-trifluoromethyl-phenyl)-pyridazin-3-yl]-morpholine as described in Example 1, Step D. $^1$H NMR (DMSO-$d_6$) δ 3.68 (t, J=4.7 Hz, 4H), 3.77 (t, J=4.7 Hz, 4H), 7.57 (d, J=1.5 Hz, 1H), 7.91 (d, J=8.5 Hz, 2H), 8.12 (d, J=8.5 Hz, 2H), 9.03 (d, J=1.5 Hz, 1H).

Step F. 2-Morpholin-4-yl-7-propyl-4-(4-trifluoromethyl-phenyl)-pyrrolo[1,2-b]pyridazine-5,6-dicarboxylic acid diethyl ester (81). n-Butyl iodide (368 mg, 2 mmol) was added to a solution of 4-[5-(4-trifluoromethyl-phenyl)-pyridazin-3-yl]-morpholine (309 mg, 1 mmol) in acetonitrile (5 mL). The resulting mixture was heated to reflux overnight, cooled and concentrated in vacuo. The residue was dissolved in THF/EtOH (85/15, 8 mL) and tetrabutylammonium fluoride (1.1 equiv., 1M THF solution) and diethyl acetylenedicarboxylate (425 mg, 2.5 mmol) were added sequentially. The mixture was stirred at 80° C. overnight, cooled to room temperature, diluted with saturated NH$_4$Cl solution, and extracted with EtOAc (2×). The combined organic layers were again washed with saturated NH$_4$Cl solution, dried over Na$_2$SO$_4$, filtered, and the filtrate was concentrated in vacuo. Column chromatography (silica gel, EtOAc/hexanes, 15/85) followed by trituration gave the title compound. $^1$H NMR (DMSO-$d_6$) δ 0.90 (t, J=7.1 Hz, 3H), 0.93 (t, J=7.3 Hz, 3H), 1.23 (t, J=7.1 Hz, 3H), 1.69 (sextet, J=7.4 Hz, 2H), 3.17 (t, J=7.0 Hz, 2H), 3.50-3.60 (m, 6H), 3.75 (t, J=5.0 Hz, 4H), 4.20 (q, J=7.1 Hz, 2H), 6.91 (s, 1H), 7.65 (d, J=8.1 Hz, 2H), 7.86 (d, J=8.1 Hz, 2H). Mass Spectrum (CI+) m/e=534.2 (M+H).

Example 82

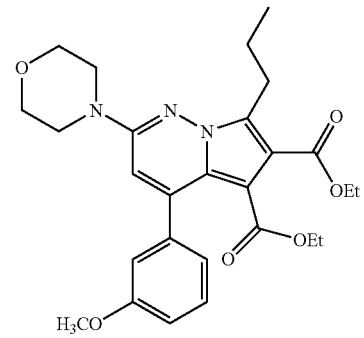

82

4-(3-Methoxy-phenyl)-2-morpholin-4-yl-7-propyl-pyrrolo[1,2-b]pyridazine-5,6-dicarboxylic acid diethyl ester (82). The title compound was prepared from the appropriate arylacetonitrile according to the procedure described in Example 81. $^1$H NMR (CDCl$_3$) δ 1.01 (m, 6H), 1.33 (t, J=7.1 Hz, 3H), 1.75 (sextet, J=7.5 Hz, 2H), 3.25 (t, J=7.5 Hz, 2H), 3.52 (t, J=5.0 Hz, 4H), 3.69 (q, J=7.1 Hz, 2H), 3.80-3.90 (m, 7H), 4.30 (q, J=7.2 Hz, 2H), 6.39 (s, 1H), 6.95-7.05 (m, 3H), 7.37 (td, J=7.5, 1.5 Hz, 1H). Mass Spectrum (CI+) m/e=450.5 (M+H).

Example 83

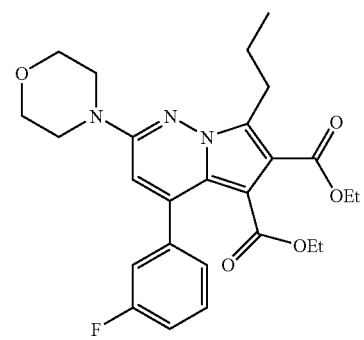

83

4-(3-Fluoro-phenyl)-2-morpholin-4-yl-7-propyl-pyrrolo[1,2-b]pyridazine-5,6-dicarboxylic acid diethyl ester (83). The title compound was prepared from the appropriate arylacetonitrile according to procedure described in Example 81. $^1$H NMR (DMSO-$d_6$) δ 0.92 (t, J=7.4Hz, 3H), 0.98 (t, J=7.2 Hz, 3H), 1.23 (t, J=7.1 Hz, 3H), 1.68 (sextet, J=7.3 Hz, 2H), 3.17 (t, J=7.0 Hz, 2H), 3.53 (t, J=4.5 Hz, 4H), 3.64 (q, J=7.1 Hz, 2H), 3.74 (t, J=4.5 Hz, 4H), 4.20 (q, J=7.1 Hz, 2H), 6.86 (s, 1H), 7.24-7.37 (m, 3H), 7.48-7.56 (m, 1H). Mass Spectrum (CI+) m/e=484.2 (M+1).

Example 84

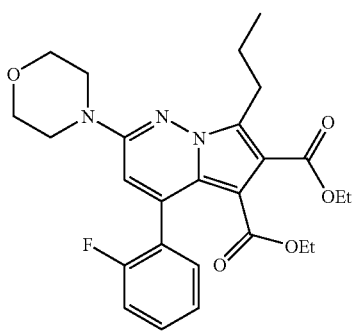

4-(2-Fluoro-phenyl)-2-morpholin-4-yl-7-propyl-pyrrolo[1,2-b]pyridazine-5,6-dicarboxylic acid diethyl ester (84). The title compound was prepared from the appropriate arylacetonitrile according to procedure described in Example 81. $^1$H NMR (DMSO-$d_6$) δ 0.93 (t, J=7.3 Hz, 3H), 0.97 (t, J=7.1 Hz, 3H), 1.22 (t, J=7.1 Hz, 3H), 1.69 (sextet, J=7.3 Hz, 2H), 3.15 (t, J=7.2 Hz, 2H), 3.45-3.61 (m, 6H), 3.74 (t, J=4.4 Hz, 4H), 4.19 (q, J=7.1 Hz, 2H), 6.91 (s, 1H), 7.27-7.35 (m, 2H), 7.41 (td, J=7.4, 1.6 Hz, 1H), 7.49-7.57 (m, 1H). Mass Spectrum (CI+) m/e=484.2 (M+H).

Example 85

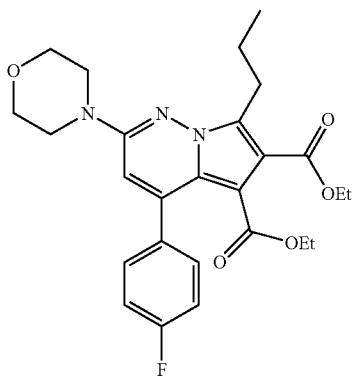

4-(4-Fluoro-phenyl)-2-morpholin-4-yl-7-propyl-pyrrolo[1,2-b]pyridazine-5,6-dicarboxylic acid diethyl ester (85). The title compound was prepared from the appropriate arylacetonitrile according to procedure described in Example 81. $^1$H NMR (DMSO-$d_6$) δ 0.93 (t, J=7.3 Hz, 3H), 0.98 (t, J=7.1 Hz, 3H), 1.23 (t, J=7.1 Hz, 3H), 1.68 (sextet, J=7.4 Hz, 2H), 3.17 (t, J=7.0 Hz, 2H), 3.53 (t, J=4.9 Hz, 4H), 3.65 (q, J=7.1 Hz, 2H), 3.74 (t, J=4.9 Hz, 4H), 4.20 (q, J=7.1 Hz, 2H), 6.80 (s, 1H), 7.30-7.37 (m, 2H), 7.45-7.50 (m, 2H). Mass Spectrum (CI+) m/e=484.2 (M+H).

Example 86

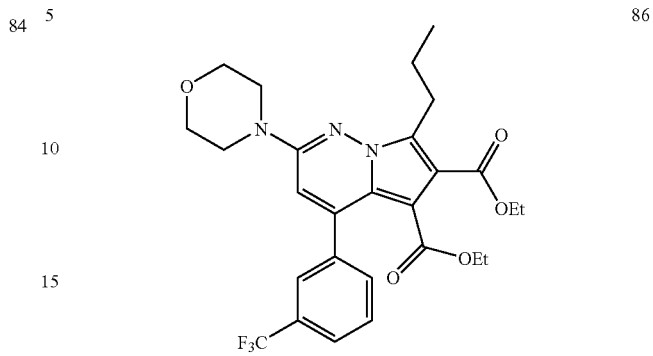

2-Morpholin-4-yl-7-propyl-4-(3-trifluoromethyl-phenyl)-pyrrolo[1,2-b]pyridazine-5,6-dicarboxylic acid diethyl ester (86). The title compound was prepared from the appropriate arylacetonitrile according to procedure described in Example 81. $^1$H NMR (DMSO-$d_6$) δ 0.91 (t, J=7.2 Hz, 3H), 0.93 (t, J=7.3 Hz, 3H), 1.23 (t, J=7.1 Hz, 3H), 1.69 (sextet, J=7.3 Hz, 2H), 3.17 (t, J=7.4 Hz, 2H), 3.50-3.60 (m, 6H), 3.74 (t, J=4.6 Hz, 4H), 4.20 (q, J=7.1 Hz, 2H), 6.92 (s, 1H), 7.70-7.78 (m, 3H), 7.83-7.90 (m, 1H). Mass Spectrum (CI+) m/e=534.2 (M+H).

Example 87

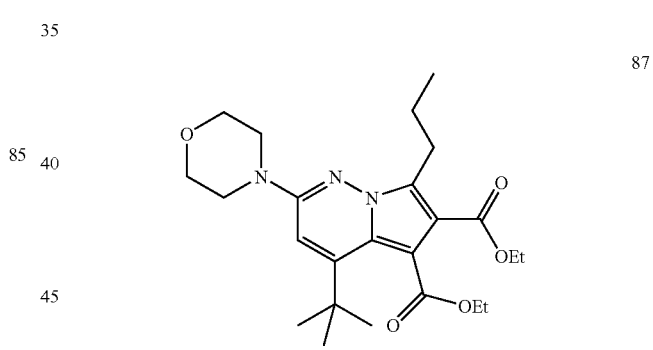

4-tert-Butyl-2-morpholin-4-yl-7-propyl-pyrrolo[1,2-b]pyridazine-5,6-dicarboxylic acid diethyl ester (87)

Step A. 4-tert-Butyl-3,6-dichloro-pyridazine. A mixture of 3,6-dichloropyridazine (1.49 g, 10.0 mmol), trimethylacetic acid (2.3 g, 22.5 mmol), concentrated sulfuric acid (0.8 mL, 15.0 mmol), and silver nitrate (0.17 g, 1.0 mmol) in 30 mL of water was heated to 65-70° C. To this was added dropwise a solution of ammonium persulfate (3.4 g, 15.0 mmol) in 10 mL of water over a 10-15 min period. The mixture was stirred at 72° C. for an additional 30 min and poured onto ice. The pH was adjusted to 9-10 with concentrated ammonium hydroxide and the contents were extracted with dichloromethane. The combined organics were washed with 1.0N sodium hydroxide and brine, dried over Na$_2$SO$_4$, filtered and the filtrate concentrated in vacuo. Column chromatography (silica gel, EtOAc/hexanes, 10/90) gave the title compound, which was elaborated without further purification. ¹H NMR (DMSO-d₆) δ 1.44 (s, 9H), 7.84 (s, 1H).

Step B. 4-tert-Butyl-2-morpholin-4-yl-7-propyl-pyrrolo[1,2-b]pyridazine-5,6-dicarboxylic acid diethyl ester (87). The title compound was prepared from 4-tert-butyl-3,6-dichloro-pyridazine as described in Example 1, Steps D, E, and F. ¹H NMR (CDCl₃) δ 1.00 (t, J=7.4 Hz, 3H), 1.37 (t, J=7.2 Hz, 3H), 1.38 (t, J=7.1 Hz, 3H), 1.44 (s, 9H), 1.62-1.75 (m, 2H), 3.18-3.27 (m, 2H), 3.47 (t, J=4.9 Hz, 4H), 3.87 (t, J=4.9 Hz, 4H), 4.29-4.41 (m, 4H), 6.46 (s, 1H). Mass Spectrum (CI+) m/e=446.3 (M+1).

Example 88

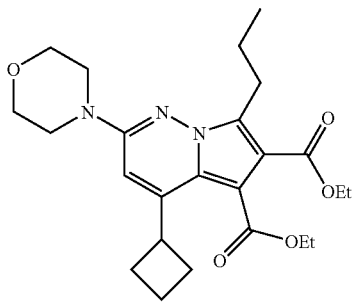

88

4-Cyclobutyl-2-morpholin-4-yl-7-propyl-pyrrolo[1,2-b]pyridazine-5,6-dicarboxylic acid diethyl ester (88). The title compound was prepared according to the procedure described in Example 87. ¹H NMR (CDCl₃) δ 0.98 (t, J=7.4 Hz, 3H), 1.37 (t, J=7.1 Hz, 3H), 1.41 (t, J=7.2 Hz, 3H), 1.70 (sextet, J=7.5 Hz, 2H), 1.80-1.90 (m, 1H) 2.00-2.18 (m, 3H), 2.25-2.35 (M, 2H), 3.17 (t, J=8.2 Hz, 2H), 3.50 (t, J=5.0 Hz, 4H), 3.88 (t, J=5.0 Hz, 4H), 3.95 (quintet, J=8.1 Hz, 1H), 4.33 (q, J=7.1 Hz, 2H), 4.42 (q, J=7.2 Hz, 2H), 6.42 (d, J=1.0Hz, 1H). Mass Spectrum (CI+) m/e=444.1 (M+1).

Example 89

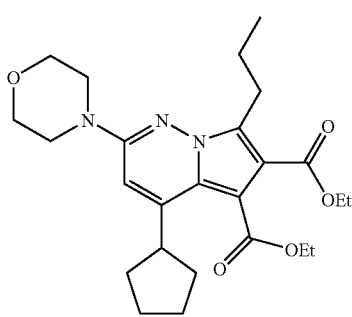

89

4-Cyclopentyl-2-morpholin-4-yl-7-propyl-pyrrolo[1,2-b]pyridazine-5,6-dicarboxylic acid diethyl ester (89). The title compound was prepared according to the procedure described in Example 87. ¹H NMR (CDCl₃) δ 0.98 (t, J=7.4 Hz, 3H), 1.37 (t, J=7.1 Hz, 3H), 1.40 (t, J=7.2 Hz, 3H), 1.56-1.84 (m, 8H), 2.02-2.11 (m, 2H), 3.20 (t, J=7.4 Hz, 2H), 3.42-3.52 (m, 5H), 3.87 (t, J=4.7 Hz, 4H), 4.34 (q, J=7.1 Hz, 2H), 4.38 (q, J=7.2 Hz, 2H), 6.39 (s, 1H). Mass Spectrum (CI+) m/e=458.2 (M+1).

Example 90

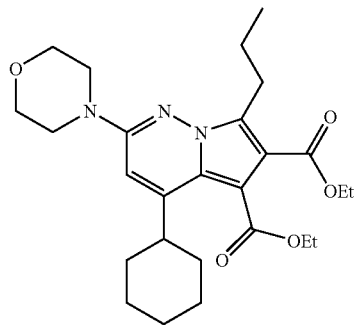

90

4-Cyclohexyl-2-morpholin-4-yl-7-propyl-pyrrolo[1,2-b]pyridazine-5,6-dicarboxylic acid diethyl ester (90). The title compound was prepared according to the procedure described in Example 87. ¹H NMR (DMSO-d₆) δ 0.89 (t, J=7.3 Hz, 3H), 1.22-1.35 (m, 9H), 1.40-1.55 (m, 2H), 1.64 (sextet, J=7.3 Hz, 2H), 1.69-1.87 (m, 5H), 2.78-2.90 (m, 1H), 3.12 (t, J=7.0 Hz, 2H), 3.47 (t, J=4.9 Hz, 4H), 3.74 (t, J=4.9 Hz, 4H), 4.18-4.30 (m, 4H), 6.71 (s, 1H). Mass Spectrum (CI+) m/e=472.3 (M+1).

Example 91

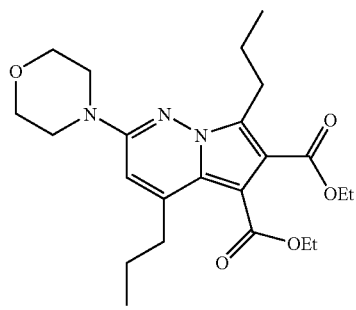

91

2-Morpholin-4-yl-4,7-dipropyl-pyrrolo[1,2-b]pyridazine-5,6-dicarboxylic acid diethyl ester (91). The title compound was prepared according to the procedure described in Example 87. ¹H NMR (DMSO-d₆) δ 0.86-0.97 (m, 6H), 1.24-1.32 (m, 6H), 1.51-1.70 (m, 4H), 2.71 (t, J=7.7 Hz, 2H), 3.10 (t, J=7.3 Hz, 2H), 3.47 (t, J=4.9 Hz, 4H), 3.74 (t, J=4.9 Hz, 4H), 4.20-4.30 (m, 4H), 6.80 (s, 1H). Mass Spectrum (CI+) m/e=432.2 (M+1).

Example 92

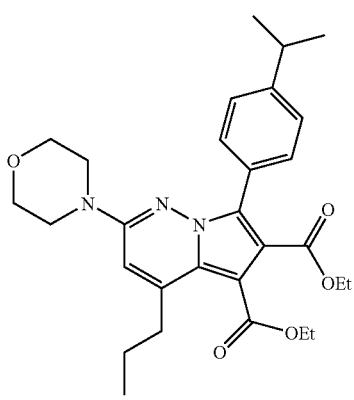

7-(4-Isopropyl-phenyl)-2-morpholin-4-yl-4-propyl-pyrrolo[1,2-b]pyridazine-5,6-dicarboxylic acid diethyl ester (92). The title compound was prepared according to procedure described in Example 87. $^1$H NMR (DMSO-d$_6$) δ 0.95 (t, J=7.2 Hz, 3H), 1.13 (t, J=7.1 Hz, 3H), 1.23-1.32 (m, 9H), 1.54-1.63 (m, 2H), 2.88 (t, J=7.7 Hz, 2H), 2.96 (septet, J=6.9 Hz, 1H), 3.37 (t, J=4.4 Hz, 4H), 3.69 (t, J=4.4 Hz, 4H), 4.13 (q, J=7.1 Hz, 2H), 4.25 (q, J=7.1 Hz, 2H), 6.93 (s, 1H), 7.33 (d, J=8.2 Hz, 2H), 7.52 (d, J=8.2 Hz, 2H). Mass Spectrum (CI+) m/e=508.5 (M+1).

Example 93

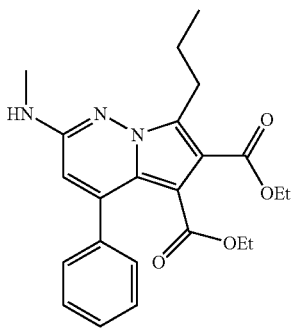

2-Methylamino-4-phenyl-7-propyl-pyrrolo[1,2-b]pyridazine-5,6-dicarboxylic acid diethyl ester (93). The title compound was prepared according to the procedure described in Example 1, replacing morpholine with the appropriate amine in Step C. $^1$H NMR (DMSO-d$_6$) δ 1.05-1.10 (m, 6H), 1.37 (t, 3H, J=7.2 Hz), 1.82-1.85 (m, 2H), 3.01 (d, 3H, J=4.4 Hz), 3.32 (t, 2H, J=7.4 Hz), 3.68 (q, 2H, J=7.1 Hz), 4.33 (q, 2H, J=7.1 Hz), 6.39 (s, 1H), 7.14 (q, J=4.4 Hz), 7.50-7.54 (m, 2H), 7.60-7.63 (m, 3H). Mass Spectrum (ES+) m/e=410.1 (M+1).

Example 94

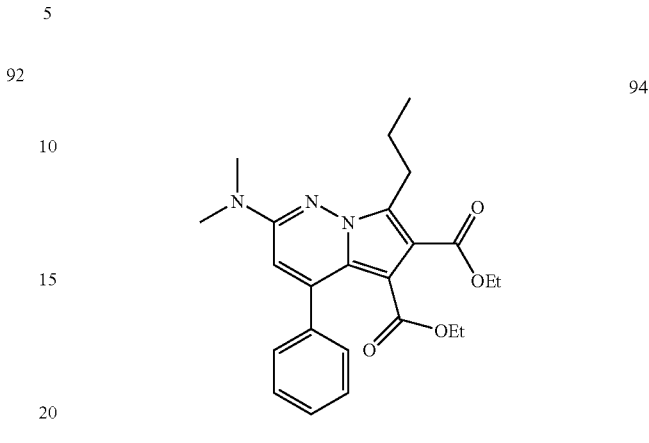

2-Dimethylamino-4-phenyl-7-propyl-pyrrolo[1,2-b]pyridazine-5,6-dicarboxylic acid diethyl ester (94). The title compound was prepared according to the procedure described in Example 1, replacing morpholine with the appropriate amine in Step C. $^1$H NMR (DMSO-d$_6$) δ 1.05-1.11 (m, 6H), 1.38 (t, 3H, J=7.1 Hz), 1.84-1.88 (m, 2H), 3.26 (s, 6H), 3.33 (t, 2H, J=7.2 Hz), 3.70 (q, 2H, J=7.0 Hz), 4.34 (q, 2H, J=7.1 Hz), 6.80 (s, 1H), 7.57-7.65 (m, 5H). Mass Spectrum (ES+) m/e=424.2 (M+1).

Example 95

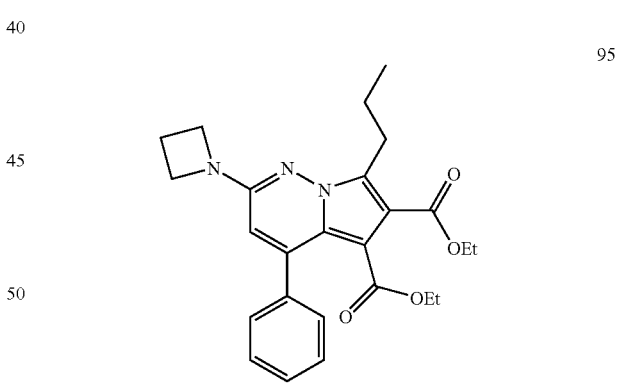

2-Azetidin-1-yl-4-phenyl-7-propyl-pyrrolo[1,2-b]pyridazine-5,6-dicarboxylic acid diethyl ester (95). The title compound was prepared according to the procedure described in Example 1, replacing morpholine with the appropriate amine in Step C. $^1$H NMR (DMSO-d$_6$) δ 1.05-1.10 (m, 6H), 1.38 (t, 3H, J=7.1 Hz), 1.81-1.87 (m, 2H), 2.50-2.54 (m, 2H), 3.31 (t, 2H, J=7.7 Hz), 3.70 (q, 2H, J=7.1 Hz), 4.23 (t, 2H, J=7.4 Hz), 4.34 (q, 2H, J=7.1 Hz), 6.40 (s, 1H), 7.54-7.64 (m, 5H). Mass Spectrum (ES+) m/e=436.2 (M+1).

Example 96

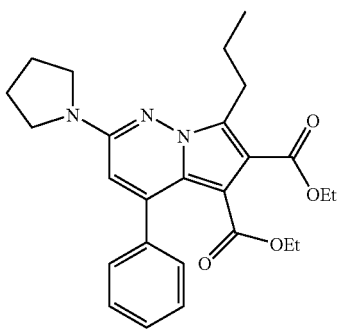

4-Phenyl-7-propyl-2-pyrrolidin-1-yl-pyrrolo[1,2-b]pyridazine-5,6-dicarboxylic acid diethyl ester (96). The title compound was prepared according to the procedure described in Example 1, replacing morpholine with the appropriate amine in Step C. $^1$H NMR (DMSO-$d_6$) δ 1.05-1.11 (m, 6H), 1.38 (t, 3H, J=7.0 Hz), 1.84-1.88 (m, 2H), 2.11-2.15 (m, 4H), 3.32 (t, 2H, J=7.6 Hz), 3.64-3.71 (m, 6H), 4.33 (q, 2H, J=7.0 Hz), 6.59 (s, 1H), 7.56-7.65 (m, 5H). Mass Spectrum (ES+) m/e=450.1 (M+1).

Example 97

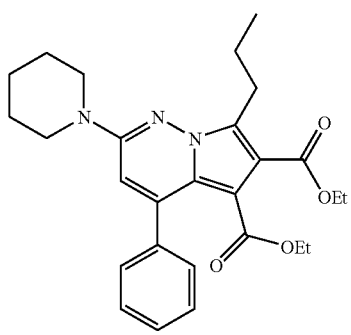

4-Phenyl-2-piperidin-1-yl-7-propyl-pyrrolo[1,2-b]pyridazine-5,6-dicarboxylic acid diethyl ester (97). The title compound was prepared according to the procedure described in Example 1, replacing morpholine with the appropriate amine in Step C. $^1$H NMR (DMSO-$d_6$) δ 1.05-1.11 (m, 6H), 1.38 (t, 3H, J=7.3 Hz), 1.78-1.87 (m, 6H), 3.32 (t, 2H, J=8.2 Hz), 3.67-3.73 (m, 6H), 4.34 (q, 2H, J=7.1 Hz), 6.91 (s, 1H), 7.56-7.64 (m, 5H). Mass Spectrum (ES+) m/e=464.2 (M+1).

Example 98

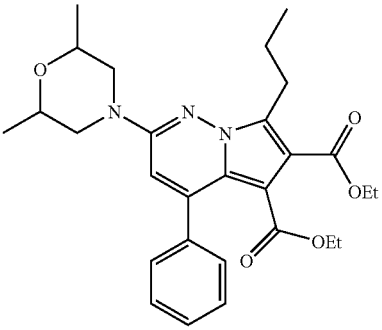

2-(2,6-Dimethylmorpholin-4-yl)-4-phenyl-7-propyl-pyrrolo[1,2-b]pyridazine-5,6-dicarboxylic acid diethyl ester (98). The title compound was prepared according to the procedure described in Example 1, replacing morpholine with the appropriate amine in Step C. $^1$H NMR (DMSO-$d_6$) δ 1.05-1.11 (m, 6H), 1.32 (d, 6H, J=6.2 Hz), 1.38 (t, 3H, J=7.0 Hz), 1.82-1.88 (m, 2H), 2.70-2.73 (m, 2H), 3.33 (t, 2H, J=7.3 Hz), 3.71 (q, 2H, J=7.2 Hz), 3.81-3.83 (m, 2H), 4.29 (d, 2H, J=11.7 Hz), 4.34 (q, 2H, J=7.0 Hz), 6.97 (s, 1H), 7.56-7.59 (m, 2H), 7.59-7.65 (m, 3H). Mass Spectrum (ES+) m/e=494.2 (M+1).

Example 99

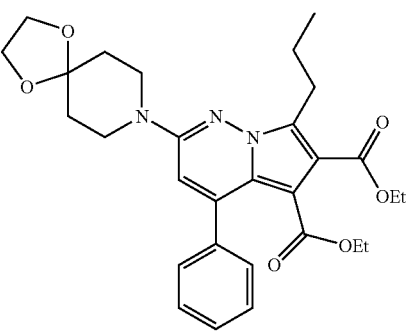

2-(1,4-Dioxa-8-aza-spiro[4.5]dec-8-yl)-4-phenyl-7-propyl-pyrrolo[1,2-b]pyridazine-5,6-dicarboxylic acid diethyl ester (99). The title compound was prepared according to the procedure described in Example 1, replacing morpholine with the appropriate amine in Step C. $^1$H NMR (DMSO-$d_6$) δ 1.05-1.11 (m, 6H), 1.38 (t, 3H, J=7.0 Hz), 1.83-1.90 (m, 6H), 3.32 (t, 2H, J=7.8 Hz), 3.70 (q, 2H, J=7.2 Hz), 3.80-3.83 (m, 4H), 4.10 (s, 4H), 4.34 (q, 2H, J=7.2 Hz), 6.97 (s, 1H), 7.58-7.64 (m, 5H). Mass Spectrum (ES+) m/e=522.2 (M+1).

Example 100

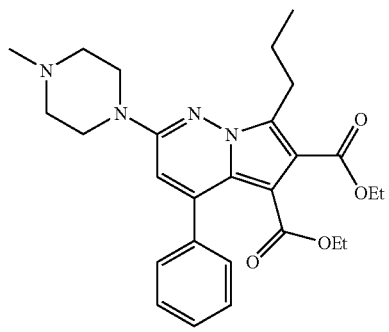

2-(4-Methyl-piperazin-1-yl)-4-phenyl-7-propyl-pyrrolo[1,2-b]pyridazine-5,6-dicarboxylic acid diethyl ester (100). The title compound was prepared according to the procedure described in Example 1, replacing morpholine with the appropriate amine in Step C. $^1$H NMR (DMSO-$d_6$) δ 1.05-1.11 (m, 6H), 1.38 (t, 3H, J=7.1 Hz), 1.80-1.90 (m, 2H), 2.38 (s, 3H), 2.58-2.61 (m, 4H), 3.40-3.45 (m, 2H), 3.69-3.71 (m, 4H), 4.34 (q, 2H, J=7.1 Hz), 6.93 (s, 1H), 7.58-7.64 (m, 5H). Mass Spectrum (ES+) m/e=479.2 (M+1).

Example 101

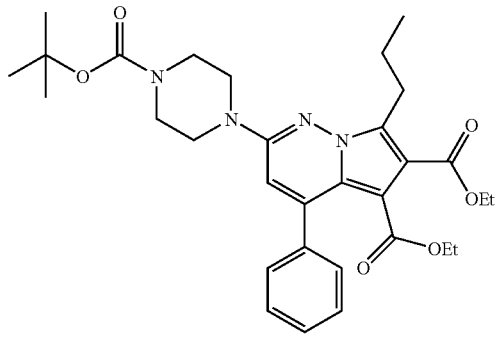

2-(4-t-Butoxycarbonyl-piperazin-1-yl)-4-phenyl-7-propyl-pyrrolo[1,2-b]pyridazine-5,6-dicarboxylic acid diethyl ester (101). The title compound was prepared according to the procedure described in Example 1, replacing morpholine with the appropriate amine in Step C. $^1$H NMR (DMSO-$d_6$) δ 1.05-1.11 (m, 6H), 1.38 (t, 3H, J=7.1 Hz), 1.51 (s, 9H), 3.32-3.34 (m, 2H), 3.62-3.72 (m, 10H), 4.34 (q, 2H, J=7.0 Hz), 6.94 (s, 1H), 7.57-7.65 (m, 5H). Mass Spectrum (ES+) m/e=565.2 (M+1).

Example 102

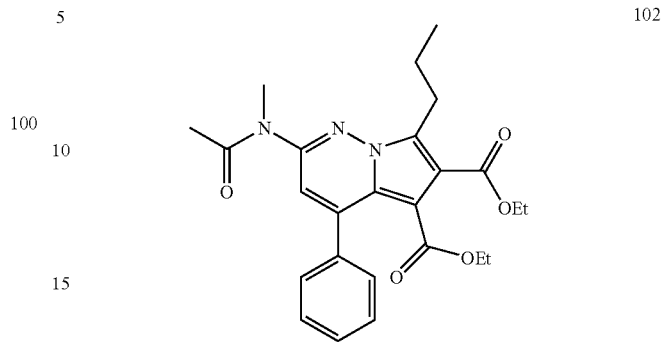

2-(Acetyl-methylamino-4-phenyl-7-propyl-pyrrolo[1,2-b]pyridazine-5,6-dicarboxylic acid diethyl ester (102). Acetic anhydride (1 mL) was added to a solution of 2-methylamino-4-phenyl-7-propyl-pyrrolo[1,2-b]pyridazine-5,6-dicarboxylic acid diethyl ester (93) (26 mg, 0.063 mmol) in pyridine (1 mL). The reaction mixture was heated to 50° C. for 16 h, quenched with water, and the layers were separated. The organic layer was washed with saturated aqueous NaHCO$_3$, brine, dried (MgSO$_4$), filtered, concentrated in vacuo. Purification by flash chromatography (silica gel, 35% EtOAc/hexane) provided the title compound. $^1$H NMR (DMSO-$d_6$) δ 1.05-1.14 (m, 6H), 1.41 (t, 3H, J=7.2 Hz), 1.82-1.87 (m, 2H), 2.35 (s, 3H), 3.37 (t, 2H, J=7.8 Hz), 3.51 (s, 3H), 3.77 (q, 2H, J=7.2 Hz), 4.40 (q, 2H, J=7.0 Hz), 7.19 (s, 1H), 7.62-7.69 (m, 5H).

Example 103

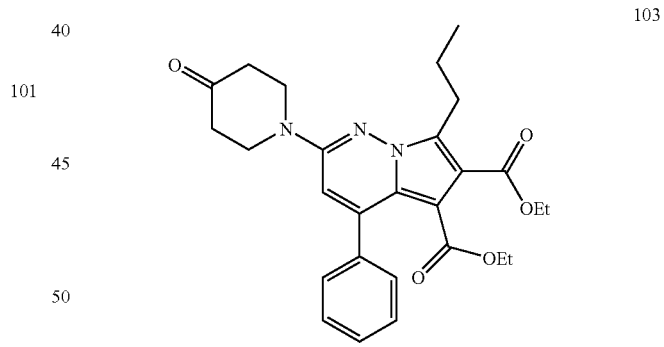

2-(4-Oxo-piperidin-1-yl) 4-phenyl-7-propyl-pyrrolo[1,2-b]pyridazine-5,6-dicarboxylic acid diethyl ester (103). Trifluoroacetic acid (2.5 mL) was added to a solution of 2-(1,4-dioxa-8-aza-spiro[4.5]dec-8-yl)-4-phenyl-7-propyl-pyrrolo[1,2-b]pyridazine-5,6-dicarboxylic acid diethyl ester (99) (245 mg, 0.47 mmol) in THF (10 mL) and water (1 mL). The reaction mixture was heated to 50° C. for 4 h, poured into aqueous NaHCO$_3$ solution. The mixture was extracted with EtOAc and the organic layer was washed with saturated aqueous NaHCO$_3$, brine, dried (MgSO$_4$), filtered and concentrated in vacuo. Purification by flash chromatography (silica gel, 35% EtOAc/hexane) provided the title compound. $^1$H NMR (DMSO-$d_6$) δ 1.05-1.11 (m, 6H), 1.38 (t, 2H, J=7.0 Hz), 1.83-1.89 (m, 2H), 2.63-2.67 (m, 4H), 3.34 (t, 2H, J=7.8 Hz), 3.71 (q, 2H, J=7.2 Hz), 4.08-4.11 (m, 4H), 4.35 (q, 2H, J=7.2 Hz), 7.05 (s, 1H), 7.60-7.66 (m, 5H). Mass Spectrum (ES+) m/e=478.2 (M+1).

Example 104

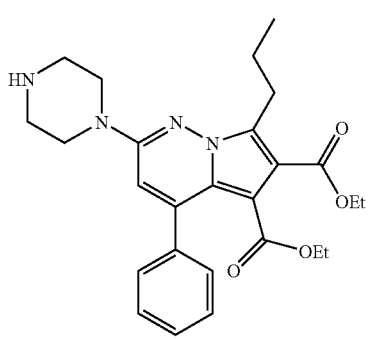

104

4-Phenyl-2-piperazin-1-yl-7-propyl-pyrrolo[1,2-b]pyridazine-5,6-dicarboxylic acid diethyl ester (104). Trifluoroacetic acid (2 mL) was added to a solution of 2-(4-t-butoxycarbonyl-piperazin-1-yl)-4-phenyl-7-propyl-pyrrolo[1,2-b]pyridazine-5,6-dicarboxylic acid diethyl ester (101) (105 mg, 0.186 mmol) in $CH_2Cl_2$ (5 mL). The reaction mixture was stirred for 1 h at ambient temperature and concentrated. Purification by flash chromatography (silica gel, 10% methanol/$CHCl_3$) provided the title compound. $^1$H NMR (DMSO-$d_6$) δ 1.05-1.11 (m, 6H), 1.39 (t, 3H, J=7.2 Hz), 3.34 (t, 2H, J=7.4 Hz), 3.40-3.42 (m, 4H), 3.72 (q, 2H, J=7.0 Hz), 3.92-3.95 (m, 4H), 4.35 (q, 2H, J=7.1 Hz), 6.99 (s, 1H), 7.57-7.67 (m, 5H), 8.94 (brs, 2H). Mass Spectrum (ES+) m/e=465.1 (M+1-114 ($CF_3CO_2H$)).

Example 105

This example describes assays that may be used to identify compounds having DGAT activity.

Numerous in vitro assay systems may be used to determine the modulation of DGAT activity. Examples of such assay systems utilize insect cell over-expression systems, tissue microsome preparations and cell culture. In the insect cell over-expression and tissue microsome preparation assay systems, the system itself provides the enzyme source for activity measurements. Such measurements are generally conducted using radiolabeled substrate, wherein the radiolabeled product that is generated is subsequently resolved by thin layer chromatography (TLC) (see, e.g., Cases, et al., Proc. Natl. Acad. Sci. (1998) 95:13018 and Cases, et al., J. Biol. Chem. (2001) 276:38870).

By comparison, cell culture-based assay systems measure intracellular synthesis of triglyceride by incubating living cells with radiolabeled fatty acid. The radiolabeled fatty acid is utilized in triglyceride biosynthesis. Triglycerides can then be extracted from the cells using organic solvent and resolved by thin layer chromatography to determine the level of radiolabel incorporation as a measure of enzyme activity (see e.g., Cases, et al., J. Biol. Chem. (2001) 276:38870).

Cell-Based Assays

In a preferred cellular assay, human colon tumor CaCO2, human hepatoma HepG2, or mouse adipocyte 3T3-L1 cells (undifferentiated or differentiated as described below) are cultured to confluency in 24 well plates. The medium is replaced with serum-free medium and the cells incubated for a further 24-48 h. Next, medium is replaced with serum-free medium containing 400 μM oleic acid (complexed with BSA, 2:1 mole:mole) and compound at varying doses in a final volume of 200 μL per well. Cells are incubated for 30 min. before adding 0.1 μCi of $^{14}$C oleic acid directly to the cells and the incubation continued for 10-30 min. depending on the cell type. Cells are washed two times with 1 mL PBS and air dried at 37° C. for 10 min. Cell lipids are extracted with 0.5 mL hexane:isopropyl alcohol (3:2 v/v) for 5 min. twice. Lipid extracts are evaporated to dryness and used for TLC using hexane:ethyl ether:acetic acid (80:20:1 v/v) as solvent. The radioactive bands are visualized and quantified by exposure to X-ray film or phosphorimager screen.

3T3-L1 cell differentiation into adipocytes is induced by incubating confluent cells in medium containing 10% serum, insulin (10 μg/mL), dexamethasone (1 μM), isobutylmethyl xanthine (IBMX, 0.5 mM), and tri-iodothyronine (T3, 10 nM). After 2 days, cells are maintained in serum, insulin, T3, and BRL49653 (1 μM) containing medium for 4-10 days.

Biochemical Assays

A preferred assay that may be used for identifying DGAT inhibitors involves a high throughput screening Scintillation Proximity Assay (SPA). In such an assay human DGAT1 is cloned from a human liver cDNA library. PCR is used to add a restriction site and flag epitope at the most 5' end and a restriction site at the 3' end of the sequence. Thereafter, human flagtag (FT) DGAT1 baculovirus may be generated using a Bac-to-Bac Baculovirus Expression System® (Invitrogen). Insect cells (e.g., sf9, sf21, or High Five) are infected for 24 to 72 h and collected by centrifugation. Cell pellets are resuspended in homogenization buffer and lysed using a homogenization device, such as a Microfluidizer. Total cell membranes are collected by ultracentrifugation at 45,000 rpm for 1 h.

A small aliquot (0.2 μg/well) of membrane is incubated with 10 μM compound or mercuric chloride (as positive control for inhibition) in the presence of enzyme substrate, dioleoyl glycerol (200 μM) in 384 well plates, final volume 50 μL per well. The reaction is started by the addition of radioactive substrate, $^{14}$C acyl coenzyme A (25 μM, such as decanoyl CoA, palmitoyl CoA, oleoyl CoA), and incubated at room temperature for 2 h. The reaction is stopped by adding Wheat Germ Agglutinin (WGA) SPA beads (0.2 mg) in mercuric chloride. Cell membranes are allowed to couple to the beads overnight. The signal can be measured using, for example, a Chemiluminescence Image Plate Reader (CLIPR) or TopCount device.

Compounds of the present invention assessed by the above-described assay were found to have DGAT-inhibiting activity. See Table 1 below.

TABLE 1

| Example | $IC_{50}$ (μM) [1] |
|---------|--------------------|
| 8       | +                  |
| 10      | +                  |
| 24      | +                  |
| 27      | ++                 |
| 64      | ++                 |
| 74      | ++                 |
| 77      | ++                 |
| 78      | +                  |
| 80      | +                  |
| 90      | ++                 |
| 94      | +                  |

TABLE 1-continued

| Example | IC$_{50}$ (μM) [1] |
|---|---|
| 95 | + |
| 96 | ++ |

[1] + represents an IC$_{50}$ value of greater than or equal to 0.5 μM   ++ represents an IC$_{50}$ value of less than 0.5 μM All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula (I):

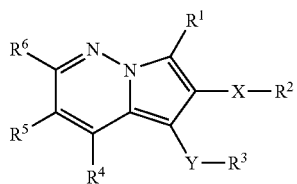

I or a pharmaceutically acceptable salt thereof, wherein

X and Y are divalent linkages independently selected from the group consisting of a single bond, (C$_1$-C$_4$) alkylene, hetero(C$_2$-C$_4$)alkylene, —O—, —CO$_2$—, —S(O)$_k$—, —C(O)—, —NR$^7$—, —C(O)NR$^7$—, —N(R$^8$)C(O)NR$^7$—, —N(R$^7$)CO$_2$—, —SO$_2$NR$^7$— and —N(R$^8$)SO$_2$NR$^7$—;

R$^1$ is selected from the group consisting of H, halogen, (C$_1$-C$_8$)alkyl, (C$_2$-C$_8$)alkenyl, (C$_2$-C$_8$)alkynyl, fluoro(C$_1$-C$_8$)alkyl, cyclo(C$_3$-C$_8$)alkyl, hetero(C$_2$-C$_8$)alkyl, heterocyclo(C$_3$-C$_8$)alkyl, aryl, aryl(C$_1$-C$_4$)alkyl, heteroaryl, OR$^a$, SR$^a$, C(O)R$^a$, CO$_2$R$^a$, C(O)NR$^a$R$^b$, SO$_2$R$^a$, SO$_2$NR$^a$R$^b$, NO$_2$ and CN;

R$^2$ is selected from the group consisting of (C$_1$-C$_8$)alkyl, aryl(C$_1$-C$_4$)alkyl, OR$^a$, halogen, NO$_2$, NR$^a$R$^b$, CN and W$^1$, wherein W$^1$ is selected from the group consisting of

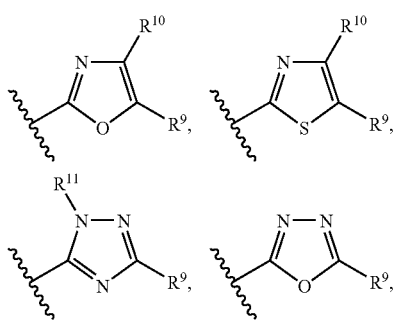

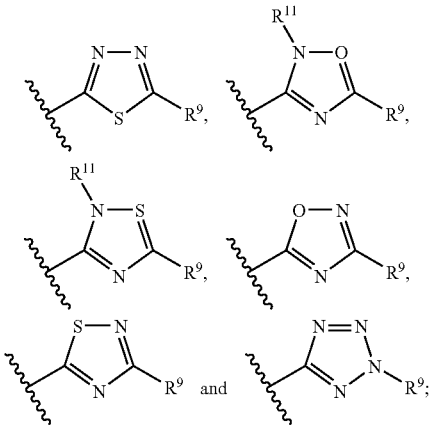

optionally, R$^1$ and R$^2$ may be combined to form a 5-, 6- or 7-membered fused ring having 0 heteroatoms or 1 heteroatom selected from the group consisting of N, O and S;

R$^3$ is selected from the group consisting of H, (C$_1$-C$_8$)alkyl, aryl(C$_1$-C$_4$)alkyl, OR$^a$, halogen, NO$_2$, NR$^a$R$^b$, CN and W$^2$, wherein W$^2$ is selected from the group consisting of

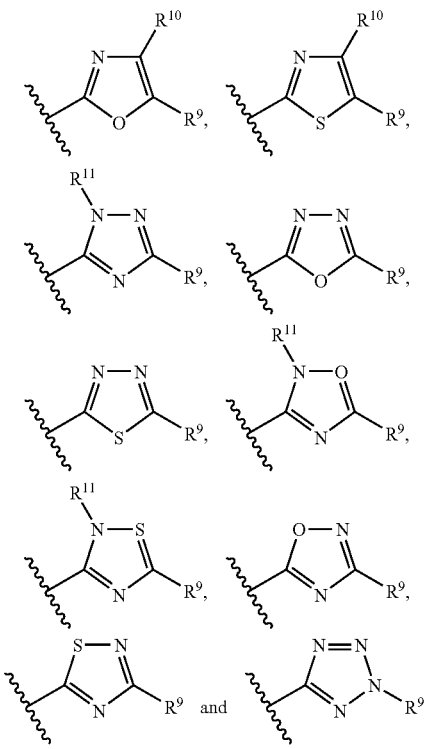

optionally, R$^2$ and R$^3$ may be combined to form a 5-, 6- or 7-membered fused ring having 0 heteroatoms or 1 heteroatom selected from the group consisting of N, O and S;

R$^4$ is selected from the group consisting of (C$_1$-C$_8$)alkyl, (C$_2$-C$_8$)alkenyl, (C$_2$-C$_8$)alkynyl, fluoro(C$_1$-C$_4$)alkyl, hetero(C$_2$-C$_8$)alkyl, cyclo(C$_3$-C$_8$)alkyl, heterocyclo (C$_3$-C$_8$)alkyl, aryl, aryl(C$_1$-C$_4$)alkyl, heteroaryl, OR$^a$, SR$^a$, NR$^a$R$^b$, C(O)R$^a$, CO$_2$R$^a$, C(O)NR$^a$R$^b$, SO$_2$R$^a$ and SO$_2$NR$^a$R$^b$;

R$^5$ is selected from the group consisting of H, (C$_1$-C$_8$) alkyl, fluoro(C$_1$-C$_8$)alkyl, cyclo(C$_3$-C$_8$)alkyl, hetero (C$_2$-C$_8$)alkyl, heterocyclo(C$_3$-C$_8$)alkyl, aryl, aryl(C$_1$-C$_4$)alkyl, heteroaryl, halogen, OR$^a$, NR$^a$R$^b$, CN, C(O)R$^a$, CO$_2$R$^a$, C(O)NR$^a$R$^b$, OC(O)R$^a$, OCO$_2$R$^c$, OC(O)NR$^a$R$^b$, NR$^a$C(O)R$^b$, NR$^a$CO$_2$R$^c$ and NR$^a$C(O)NR$^b$R$^a$, R$^6$ is NR$^d$R$^e$;

R$^7$ and R$^8$ are independently selected from the group consisting of H, (C$_1$-C$_8$)alkyl, aryl and aryl(C$_1$-C$_4$)alkyl;

each R$^9$ and R$^{10}$ is independently selected from the group consisting of H, (C$_1$-C$_8$)alkyl, (C$_2$-C$_8$)alkenyl, (C$_2$-C$_8$)alkynyl, fluoro(C$_1$-C$_8$)alkyl, aryl and aryl(C$_1$-C$_4$)alkyl; or optionally, R$^9$ and R$^{10}$ may be combined to form a 5-, 6- or 7-membered fused ring having 0, 1, 2 or 3 heteroatoms independently selected from the group consisting of N, O and S;

each R$^{11}$ is independently selected from the group consisting of H, (C$_1$-C$_8$)alkyl, aryl and aryl(C$_1$-C$_4$)alkyl;

each R$^a$ and R$^b$ is independently selected from the group consisting of H, (C$_1$-C$_8$)alkyl, cyclo(C$_3$-C$_8$)alkyl, aryl and aryl(C$_1$-C$_4$)alkyl;

each R$^c$ is independently selected from the group consisting of (C$_1$-C$_8$)alkyl, cyclo(C$_3$-C$_8$)alkyl, aryl and aryl (C$_1$-C$_4$)alkyl;

R$^d$ and R$^e$ are independently selected from the group consisting of H, (C$_1$-C$_8$)alkyl, (C$_2$-C$_8$)alkenyl, (C$_2$-C$_8$) alkynyl, fluoro(C$_1$-C$_8$)alkyl, C(O)R$^f$, aryl and aryl(C$_1$-C$_4$)alkyl;

optionally, R$^d$ and R$^e$ may be combined to form a 4-, 5-, 6- or 7-membered ring with the nitrogen atom to which they are attached and 0, 1 or 2 additional heteroatoms independently selected from the group consisting of N, O and S;

R$^f$ is selected from the group consisting of H, (C$_1$-C$_8$) alkyl, amino, (C$_1$-C$_4$)alkylamino, (C$_1$-C$_4$)dialkylamino, aryl(C$_1$-C$_4$)alkyl and (C$_1$-C$_8$)alkoxy; and the subscript k is independently 0, 1 or 2.

2. A compound of claim 1 or a pharmaceutically acceptable salt thereof, wherein R$^4$ is substituted or unsubstituted phenyl.

3. A compound of claim 2 or a pharmaceutically acceptable salt thereof, having the formula (II):

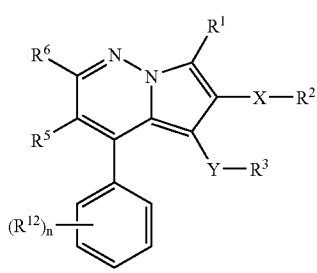

II wherein
each R$^{12}$ is selected from the group consisting of (C$_1$-C$_4$) alkyl, fluoro(C$_1$-C$_8$)alkyl, halogen and aryl; and
the subscript n is 0, 1, 2 or 3.

4. A compound of claim 2 or a pharmaceutically acceptable salt thereof, wherein R$^6$ is selected from the group consisting of azetidinyl, pyrrolyl, pyrrolidinyl, imidazolyl, triazolyl, piperidinyl, morpholinyl, piperazinyl and indolyl.

5. A compound of claim 4 or a pharmaceutically acceptable salt thereof, having the formula (III):

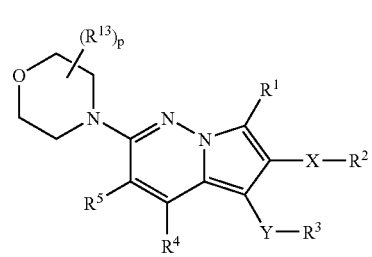

III wherein
each R$^{13}$ is selected from the group consisting of (C$_1$-C$_4$) alkyl, fluoro(C$_1$-C$_8$)alkyl, halogen and aryl; and
the subscript p is 0, 1, 2 or 3.

6. A compound of claim 2 or a pharmaceutically acceptable salt thereof, having the formula (IV):

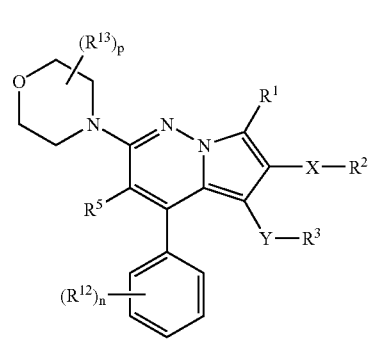

IV wherein
each R$^{12}$ and R$^{13}$ is selected from the group consisting of(C$_1$-C$_4$)alkyl, fluoro(C$_1$-C$_8$)alkyl, halogen and aryl; and
the subscripts n and p are independently 0, 1, 2 or 3.

7. A compound of claim 6 or a pharmaceutically acceptable salt thereof, wherein R$^5$ is H or halogen.

8. A compound of claim 6 or a pharmaceutically acceptable salt thereof, wherein X and Y are independently selected from the group consisting of a single bond, (C$_1$-C$_4$)alkylene, —C(O)—, —CO$_2$—, —N(R$^7$)C(O)— and —N(R$^7$)CO$_2$—.

9. A compound of claim 8 or a pharmaceutically acceptable salt thereof, wherein X and Y are independently selected from the group consisting of a single bond, (C$_1$-C$_4$)alkylene and —CO$_2$—; R$^2$ is selected from the group consisting of(C$_1$-C$_8$)alkyl, aryl(C$_1$-C$_4$)alkyl, OR$^a$ and W$^1$; and R$^3$ is selected from the group consisting of(C$_1$-C$_8$)alkyl, aryl(C$_1$-C$_4$)alkyl, OR$^a$ and W$^2$.

10. A compound of claim 9 or a pharmaceutically acceptable salt thereof, wherein X and Y are —CO$_2$— and R$^2$ and R$^3$ are independently (C$_1$-C$_8$)alkyl or aryl(C$_1$-C$_4$)alkyl.

11. A compound of claim 9 or a pharmaceutically acceptable salt thereof, wherein X is a single bond and R$^2$ is W$^1$.

12. A compound of claim 7 or a pharmaceutically acceptable salt thereof, wherein R$^1$ is selected from the group consisting of H, $(C_1$-$C_8)$alkyl, $(C_2$-$C_8)$alkenyl, fluoro$(C_1$-$C_8)$alkyl, cyclopropyl, cyclobutyl, cyclopentyl, cyclohexyl, phenyl, pyridyl and benzyl.

13. A compound of claim 7 or a pharmaceutically acceptable salt thereof, wherein $R^1$ and $R^2$ are combined to form a 5- or 6-membered fused ring having N or O as a ring member.

14. A pharmaceutical composition comprising a pharmaceutically acceptable carrier or excipient and a compound of claim 1 or a pharmaceutically acceptable salt thereof.

15. A method of treating a disease or condition selected from the group consisting of obesity, type II diabetes, syndrome X, insulin resistance, hyperglycemia, hyperinsulinemia, hypercholesterolemia, hyperlipidemia, hypertriglyceridemia, nonalcoholic fatty liver disease, atherosclerosis, arteriosclerosis, coronary artery disease, and myocardial infarction, comprising administering to a subject in need thereof a therapeutically effective amount of a compound of claim 1 or a pharmaceutically acceptable salt thereof.

16. A method in accordance with claim 15, wherein said compound or a pharmaceutically acceptable salt thereof is administered orally, parenterally or topically.

17. A method in accordance with claim 15, wherein said compound or a pharmaceutically acceptable salt thereof is administered in combination with a second therapeutic agent.

* * * * *